US011525470B2

(12) United States Patent
Richter et al.

(10) Patent No.: US 11,525,470 B2
(45) Date of Patent: Dec. 13, 2022

(54) CLOSURE DEVICE WITH AN ADJUSTING DEVICE FOR AUTOMATICALLY ROTATING A CONNECTION ELEMENT OF A CLOSURE PART INTO A CLOSED POSITION

(71) Applicant: Fidlock GmbH, Hannover (DE)

(72) Inventors: Friedemann Richter, Hannover (DE); Breido Botkus, Hannover (DE); Joachim Fiedler, Hannover (DE)

(73) Assignee: Fidlock GmbH, Hannover (DE)

( * ) Notice: Subject to any disclaimer, the term of this patent is extended or adjusted under 35 U.S.C. 154(b) by 1214 days.

(21) Appl. No.: 16/061,798

(22) PCT Filed: Dec. 14, 2016

(86) PCT No.: PCT/EP2016/081060
§ 371 (c)(1),
(2) Date: Jul. 16, 2018

(87) PCT Pub. No.: WO2017/102878
PCT Pub. Date: Jun. 22, 2017

(65) Prior Publication Data
US 2018/0363689 A1 Dec. 20, 2018

(30) Foreign Application Priority Data

Dec. 16, 2015 (DE) ...................... 10 2015 225 438.0

(51) Int. Cl.
*F16B 7/20* (2006.01)
*F16M 13/02* (2006.01)
(Continued)

(52) U.S. Cl.
CPC ................ *F16B 7/20* (2013.01); *A61F 2/76* (2013.01); *A61F 2/78* (2013.01); *B60R 11/00* (2013.01);
(Continued)

(58) Field of Classification Search
CPC ...... F16M 11/041; F16M 11/08; F16M 11/06; A61F 2/76; A61F 2/78; F16B 7/20
See application file for complete search history.

(56) References Cited

U.S. PATENT DOCUMENTS 4,982,581 A 1/1991 Furuyama
4,993,575 A 2/1991 Maes
(Continued)

FOREIGN PATENT DOCUMENTS

DE     20004567 U1    7/2000
DE   102008006135 A1  7/2009
(Continued)

*Primary Examiner* — Daniel J Wiley
(74) *Attorney, Agent, or Firm* — The Webb Law Firm

(57) ABSTRACT

The invention relates to a closure device (V) comprising at least one first and second closure part (1, 2). In particular, a first connection element (12) of the first closure part (1) has at least one guide portion (121), and a second connection element (22) of the second closure part (2) has at least one closure portion (221), wherein—the guide portion (121) has a guide surface (1210) which is inclined relative to the connection axis (A), with which the closure portion (221) comes into contact when the second closure part (2) is placed on the first closure part (1), and which forces the second connection element (22) to rotate about the connection axis (A) relative to the first connection element (12) along a first rotational direction (D1) when the two closure parts (1, 2) further approach each other under the effect of at least two magnet elements (M1, M2; M3, M4) of the closure device (V), —the closure device (V) has an adjusting device (M3, M4; 24) by means of which a force is applied to the second connection element (22), which has now assumed an intermediate position, in a second rotational direction (D2) opposite the first rotational direction (D1) such that the second connection element (22) is automatically rotated out of the intermediate position into a closed position relative to (Continued)

the first connection element (12) along the second rotational direction (D2), and —in the closed position (a), the closure portion (221) at least partly engages behind the guide portion (121) in order to hold the connection elements (12, 22), and thus the closure parts (1, 2), against each other, and (b) the second connection element (22) can be rotated in the first rotational direction (D1) in order to release the two closure parts (1, 2) from each other in order to open the closure device (V).

20 Claims, 67 Drawing Sheets

(51) Int. Cl.
| | | |
|---|---|---|
| | *F16M 11/04* | (2006.01) |
| | *A61F 2/78* | (2006.01) |
| | *B60R 11/00* | (2006.01) |
| | *A61F 2/76* | (2006.01) |
| | *A43C 11/14* | (2006.01) |
| | *F16B 1/00* | (2006.01) |
| | *A61F 2/50* | (2006.01) |
| | *A61F 2/68* | (2006.01) |
| | *A43B 1/00* | (2006.01) |
| | *A45C 13/10* | (2006.01) |

(52) U.S. Cl.
CPC .......... *F16M 11/041* (2013.01); *F16M 13/02* (2013.01); *A43B 1/0054* (2013.01); *A43C 11/14* (2013.01); *A45C 13/1069* (2013.01); *A61F 2002/5083* (2013.01); *A61F 2002/6854* (2013.01); *A61F 2002/7862* (2013.01); *F16B 2001/0035* (2013.01)

(56) References Cited

U.S. PATENT DOCUMENTS

| | | | |
|---|---|---|---|
| 5,092,019 | A | 3/1992 | Levy |
| 8,317,048 | B2 | 11/2012 | Hajichristou et al. |
| 10,578,241 | B2 * | 3/2020 | Fiedler ................ F16M 11/041 |
| 2009/0067921 | A1 | 3/2009 | Ito et al. |
| 2010/0308605 | A1 | 12/2010 | Fiedler |
| 2011/0030174 | A1 | 2/2011 | Fiedler |
| 2013/0000084 | A1 | 1/2013 | Nassar |
| 2013/0017014 | A1 | 1/2013 | Wandelt |
| 2013/0327912 | A1 | 12/2013 | Yoshida et al. |
| 2016/0010371 | A1 | 1/2016 | Fiedler |
| 2016/0183642 | A1 | 6/2016 | Fiedler |

FOREIGN PATENT DOCUMENTS

| | | |
|---|---|---|
| DE | 102015216242 A1 | 3/2017 |
| EP | 0170042 B1 | 2/1986 |
| EP | 1970574 A2 | 9/2008 |
| EP | 2334571 B1 | 10/2012 |
| JP | 200444619 A | 2/2004 |
| WO | 9218028 A1 | 10/1992 |
| WO | 2009127196 A2 | 10/2009 |
| WO | 2013160607 A1 | 10/2013 |
| WO | 2014086874 A1 | 6/2014 |
| WO | 2015004278 A1 | 1/2015 |

* cited by examiner

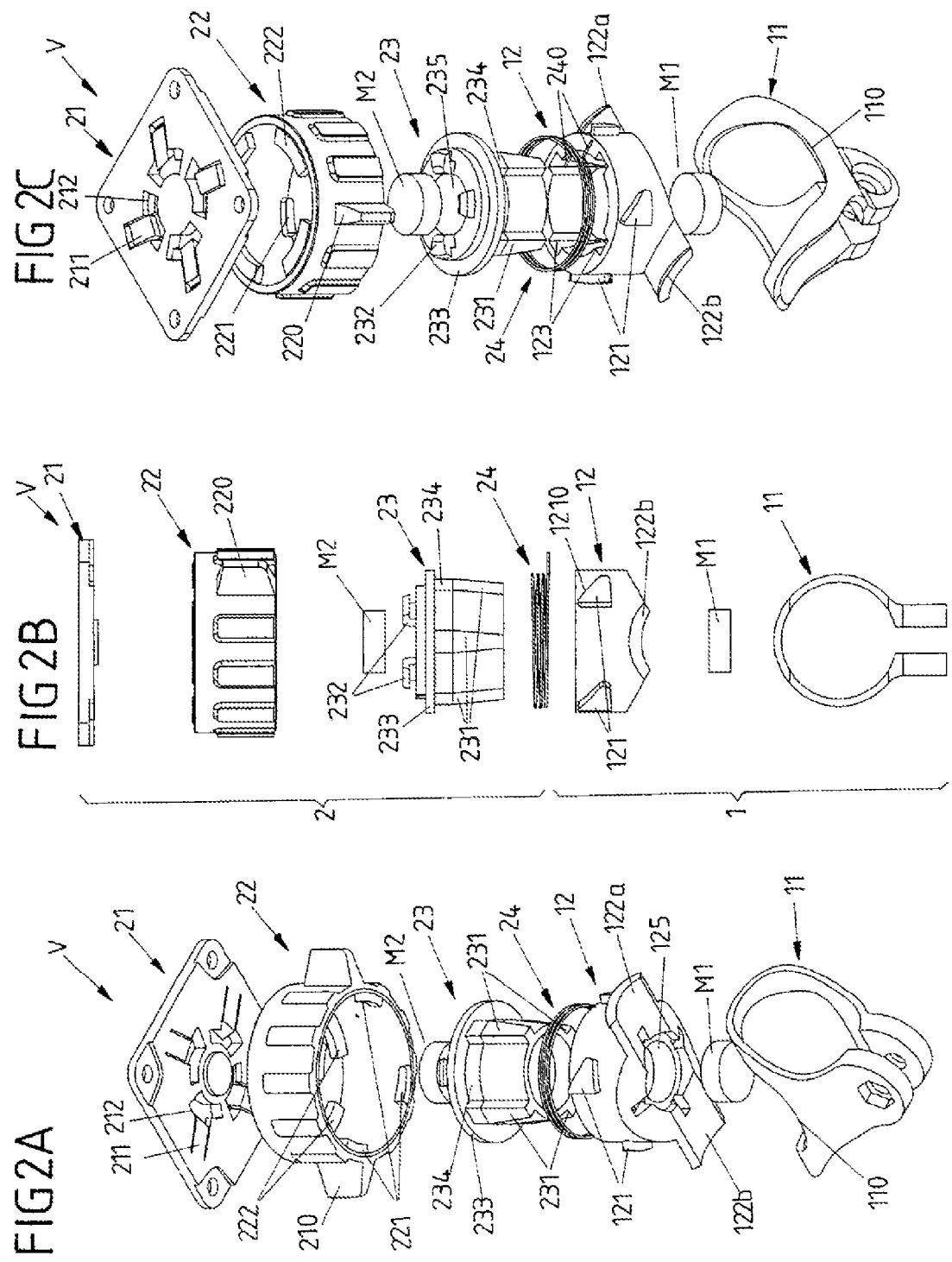

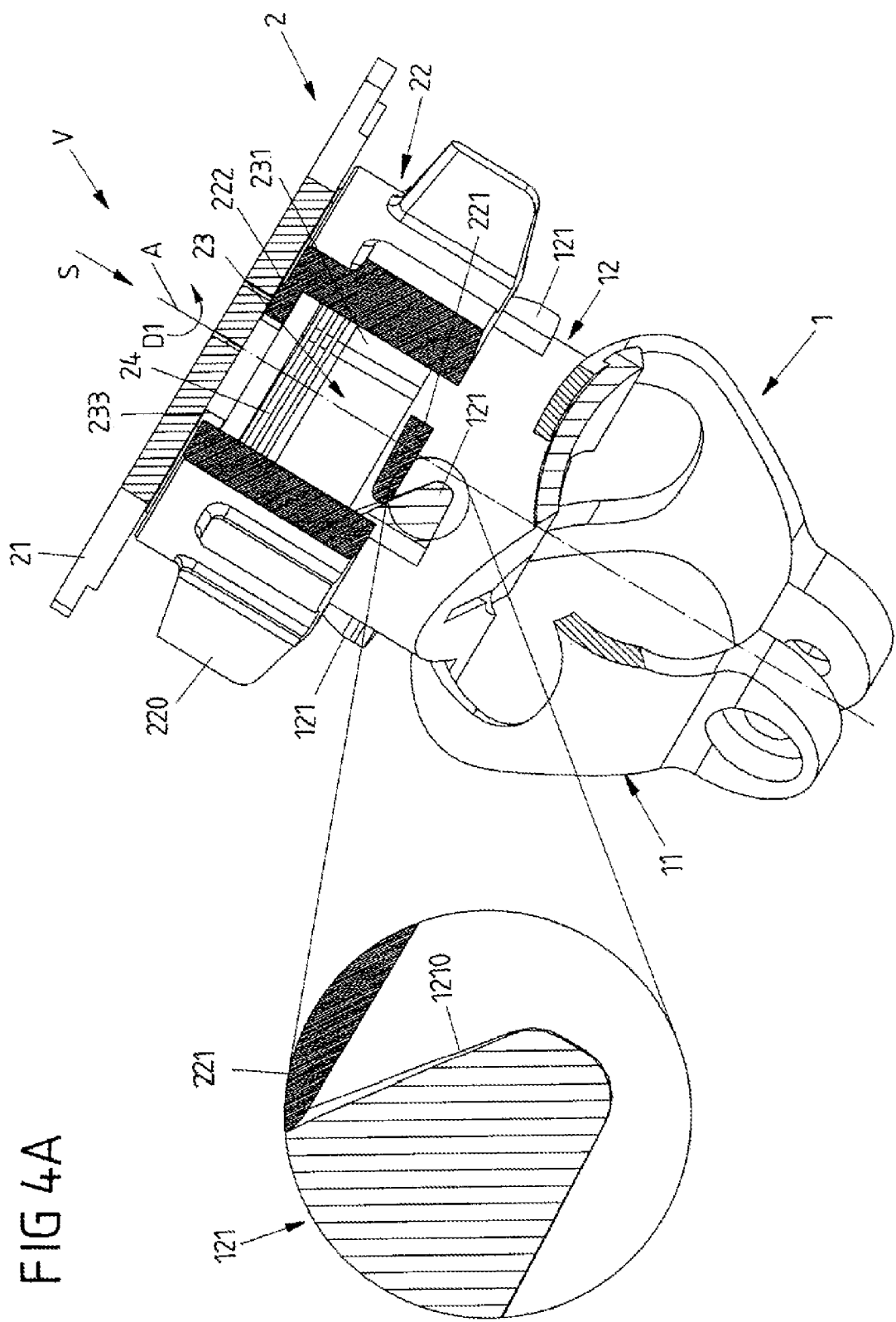

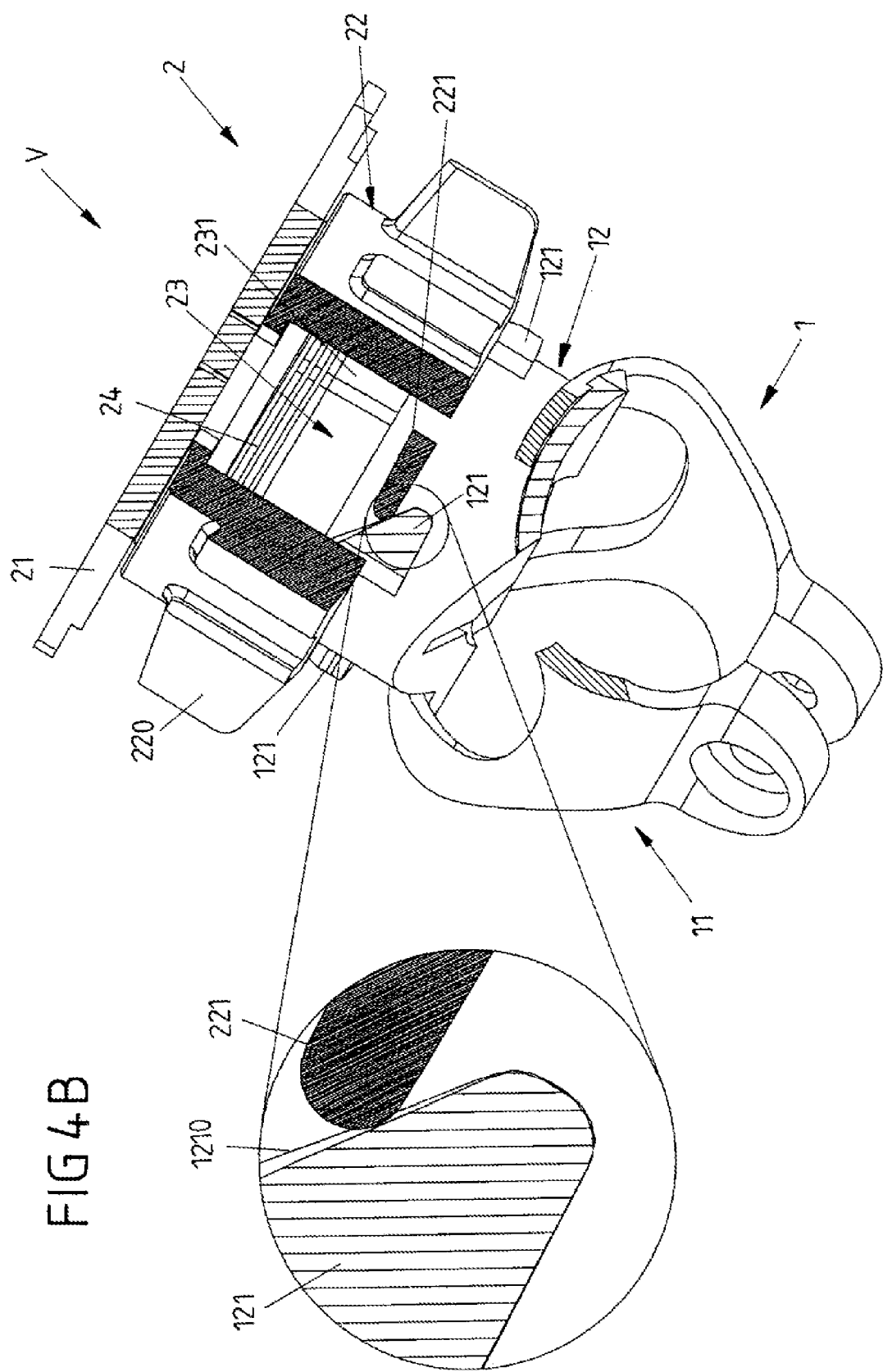

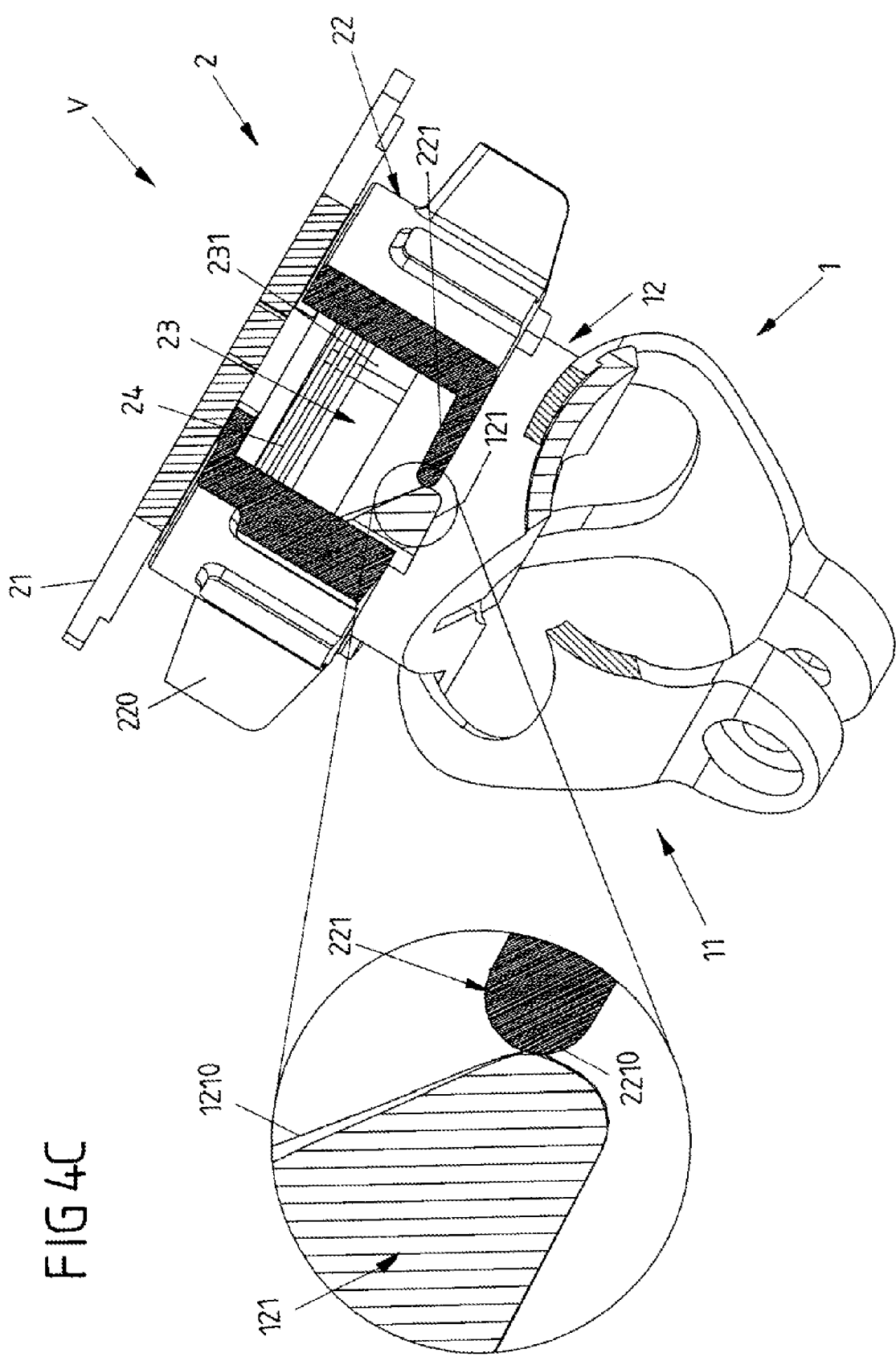

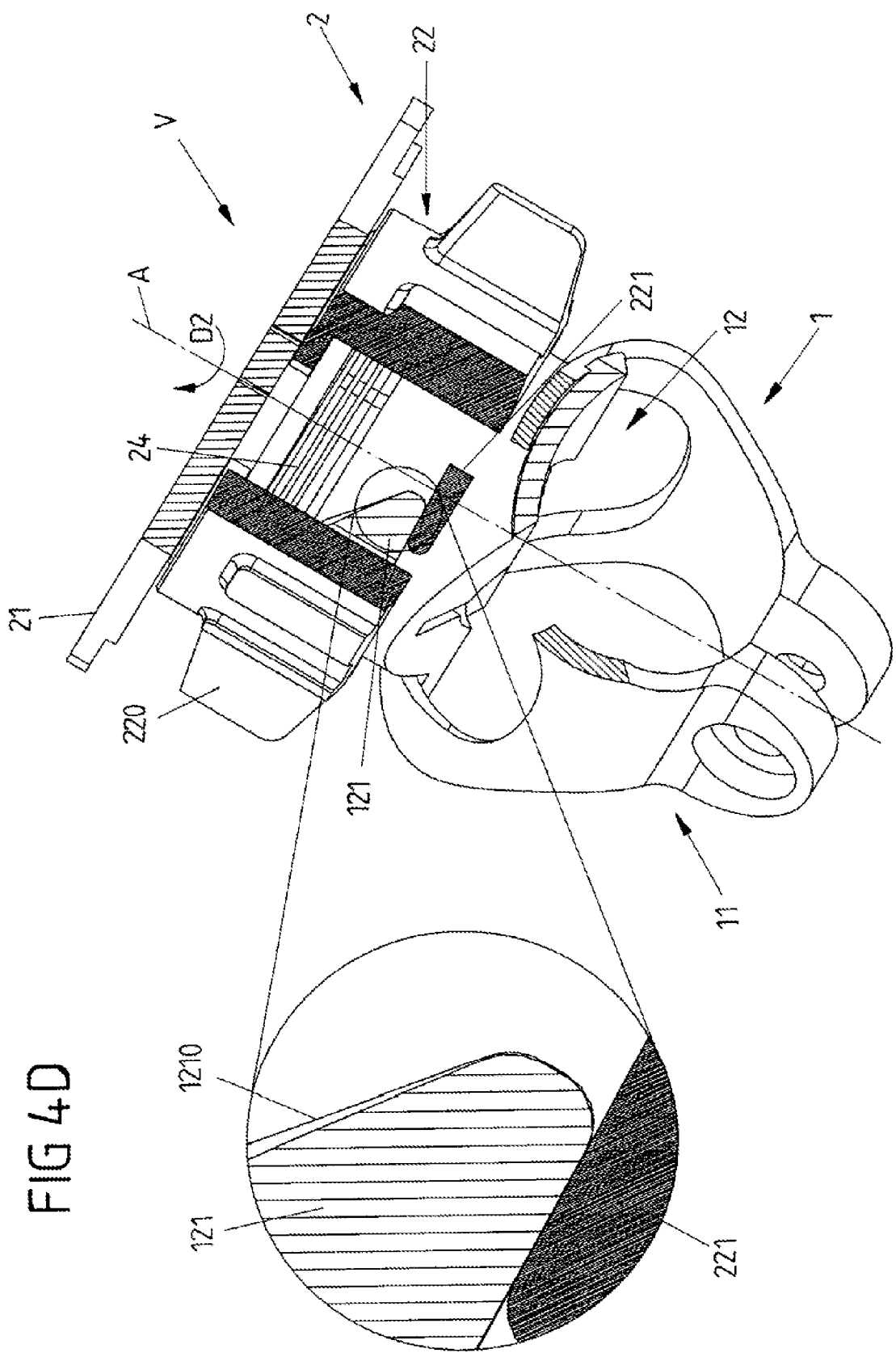

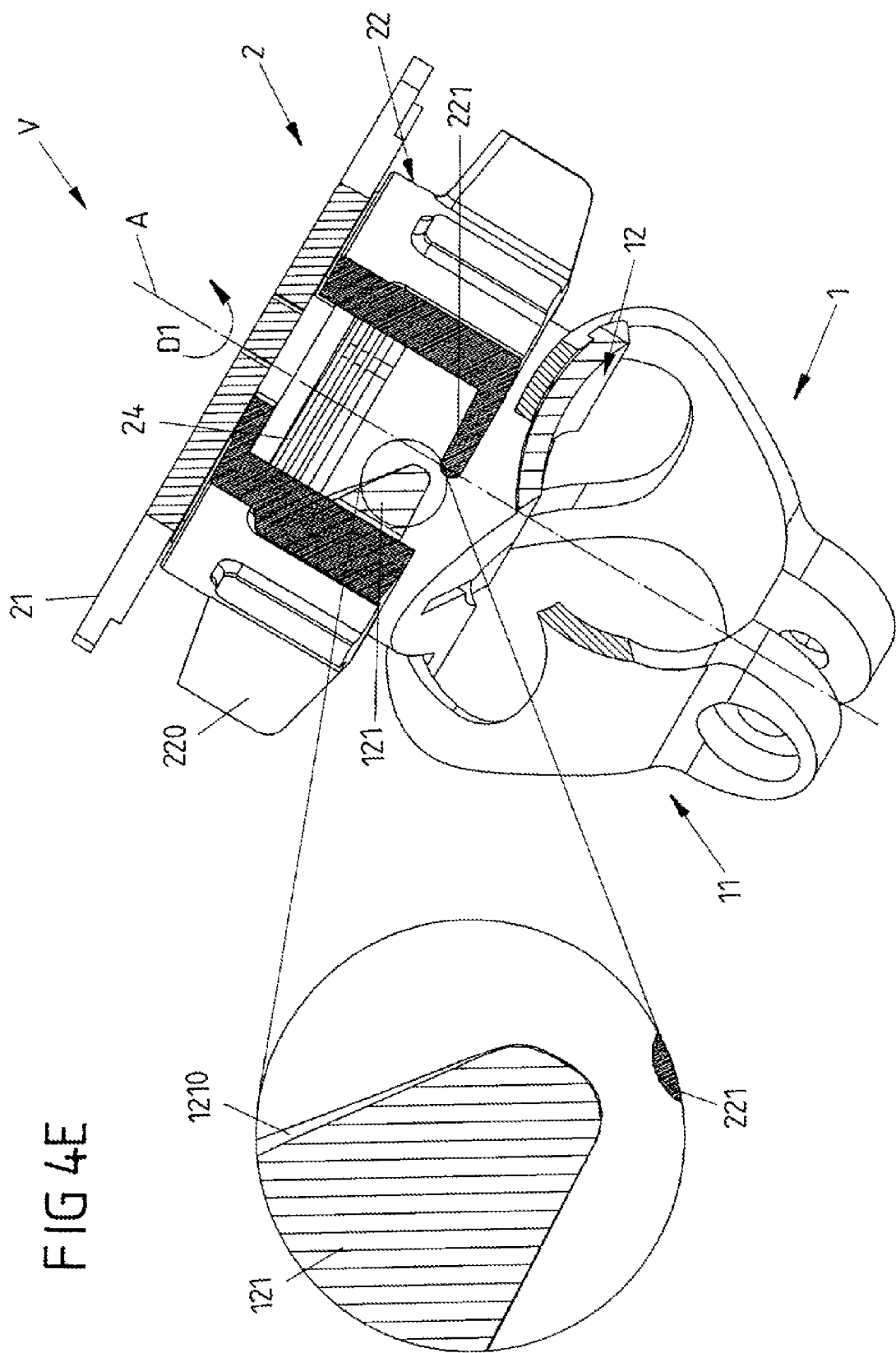

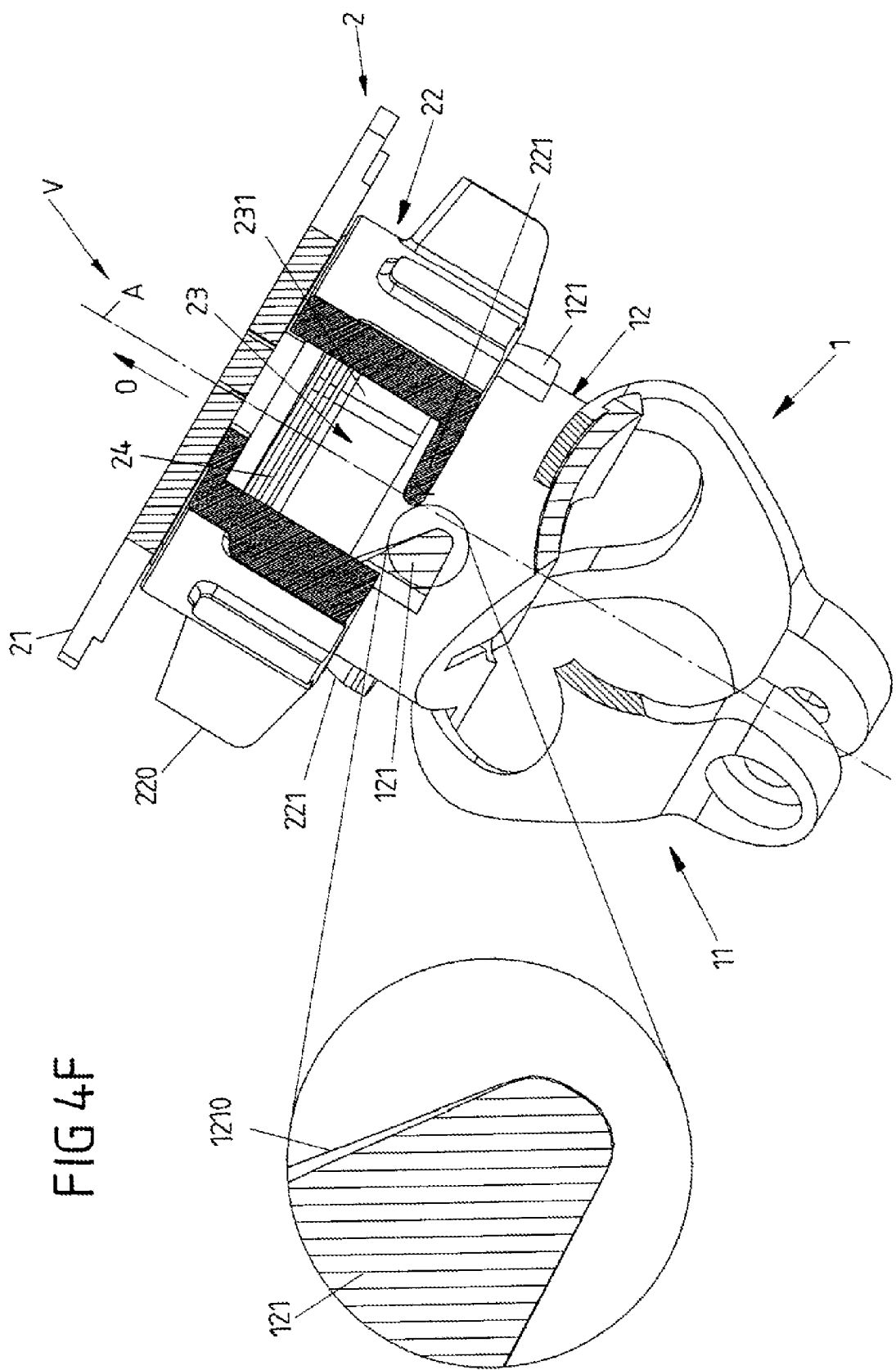

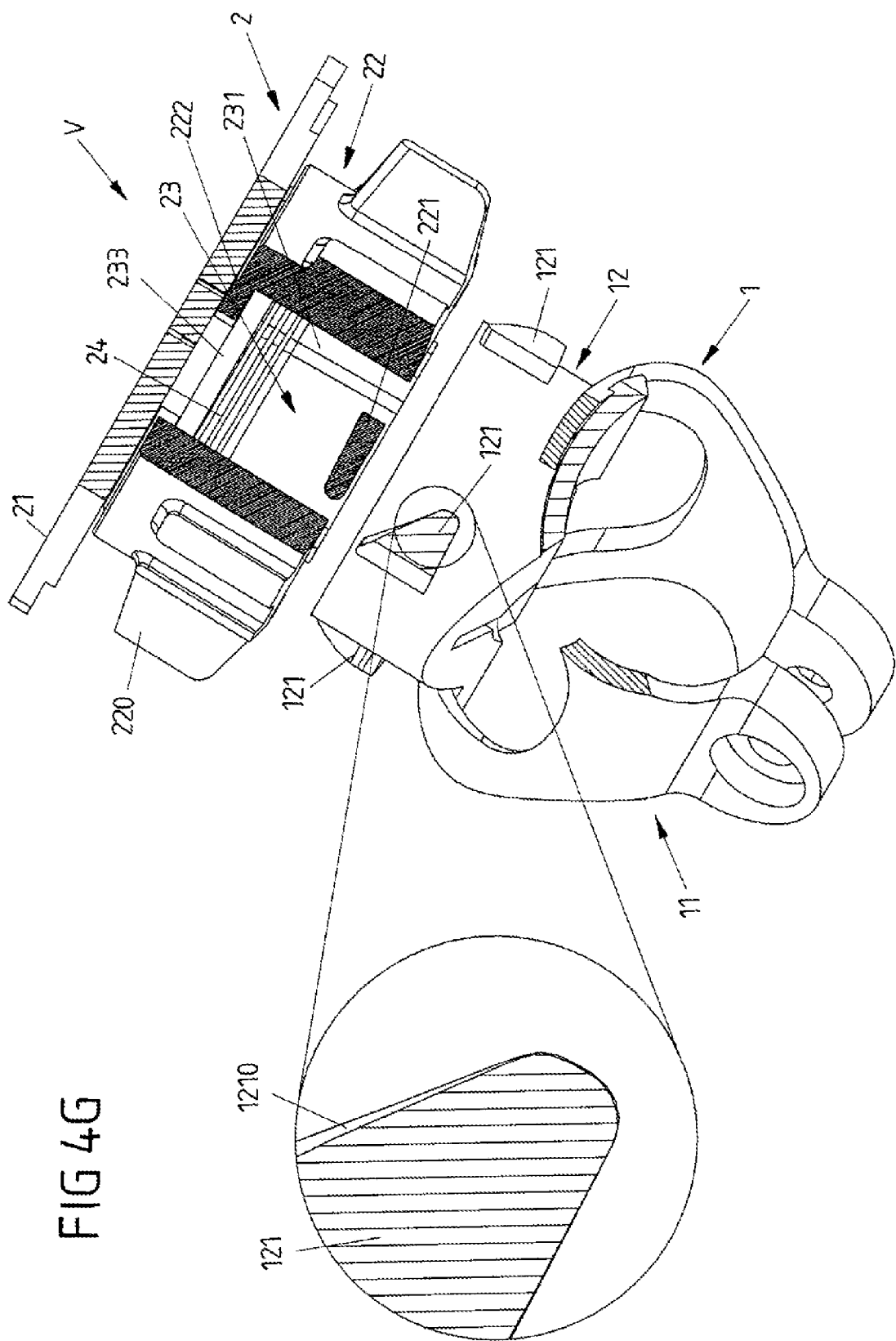

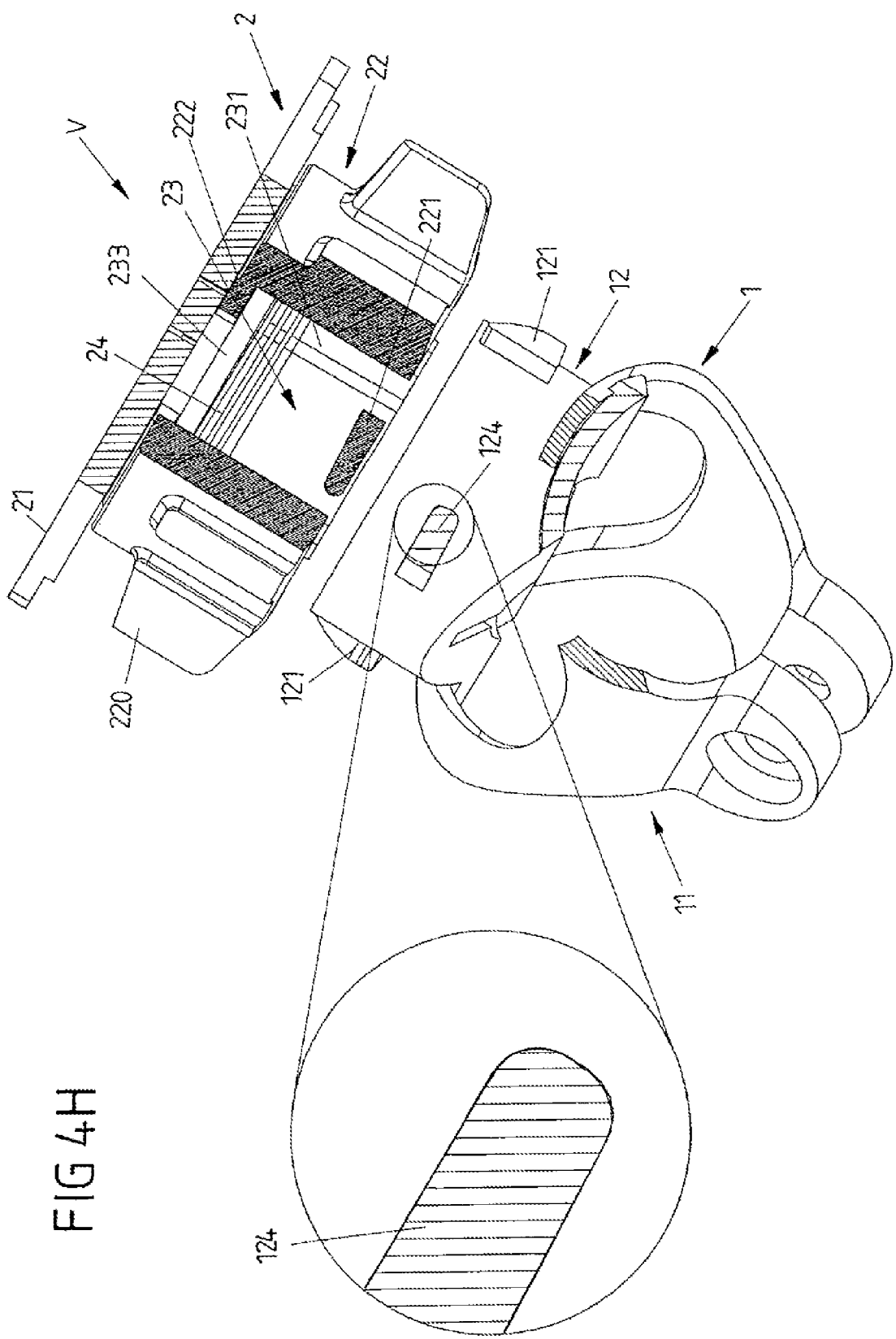

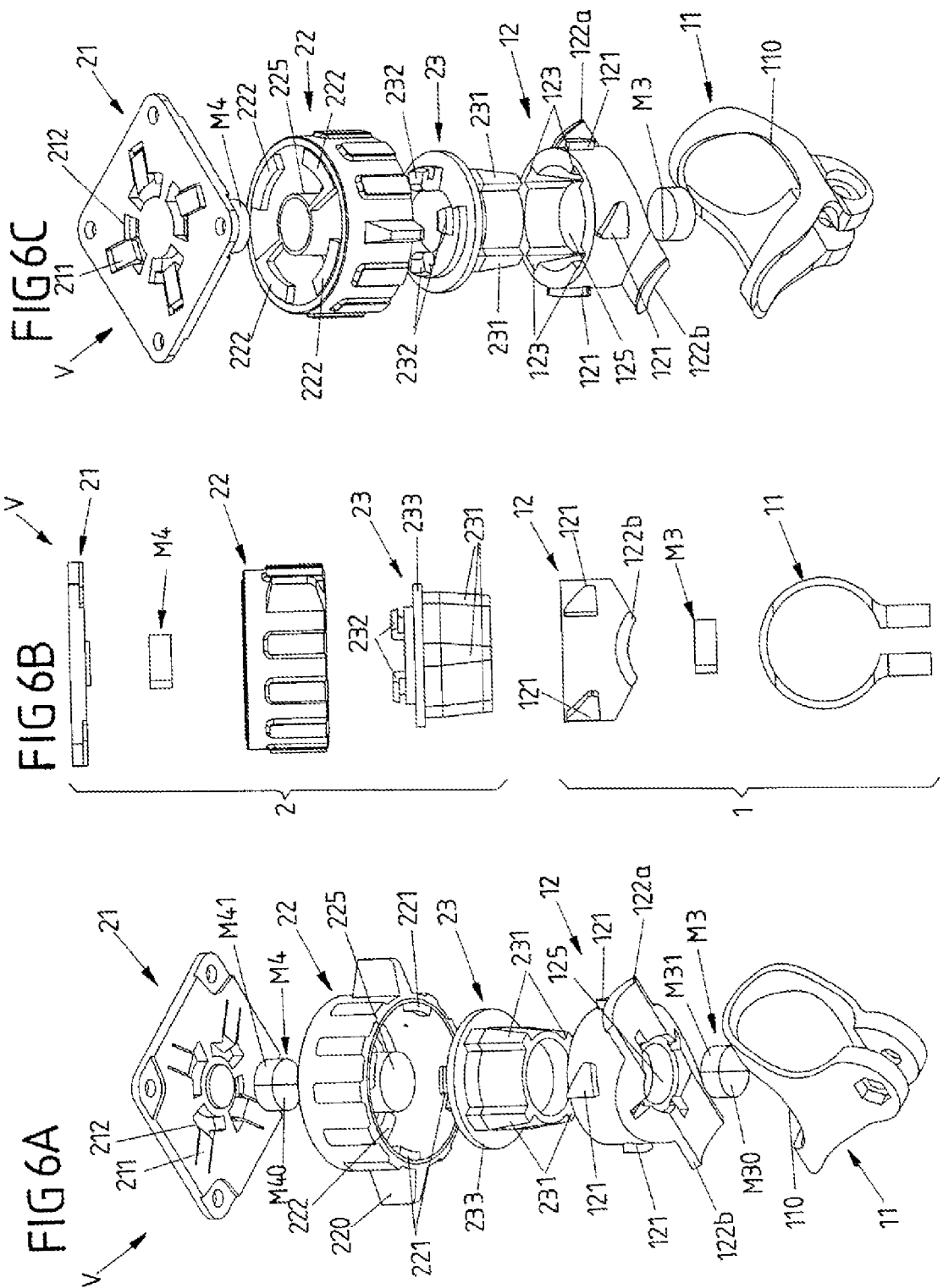

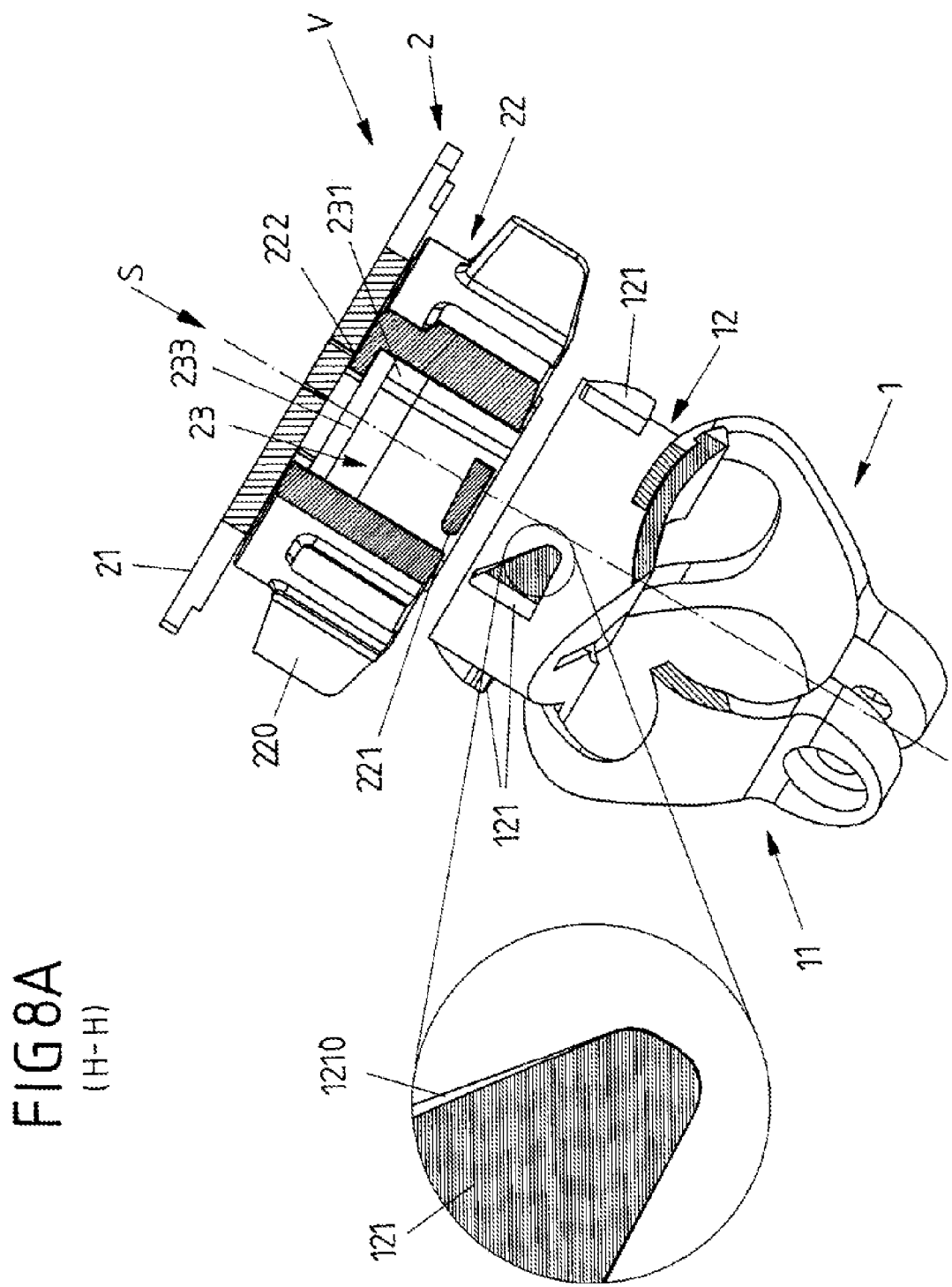

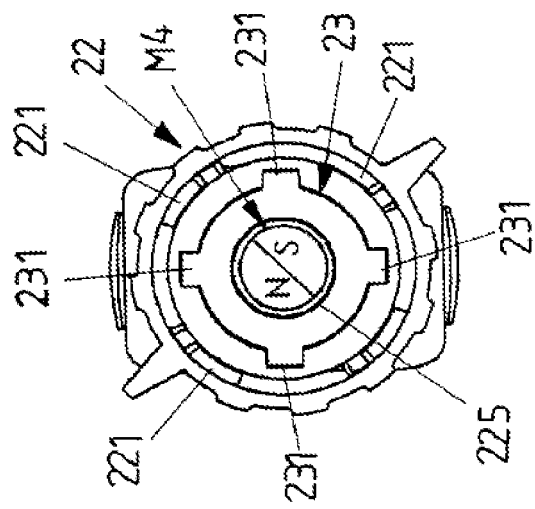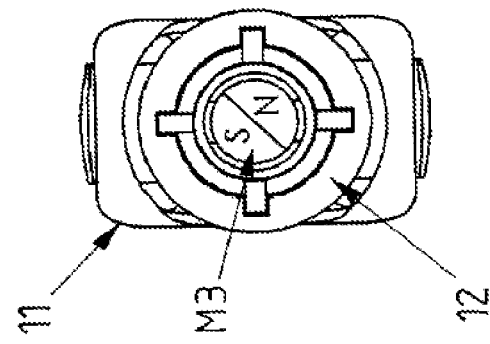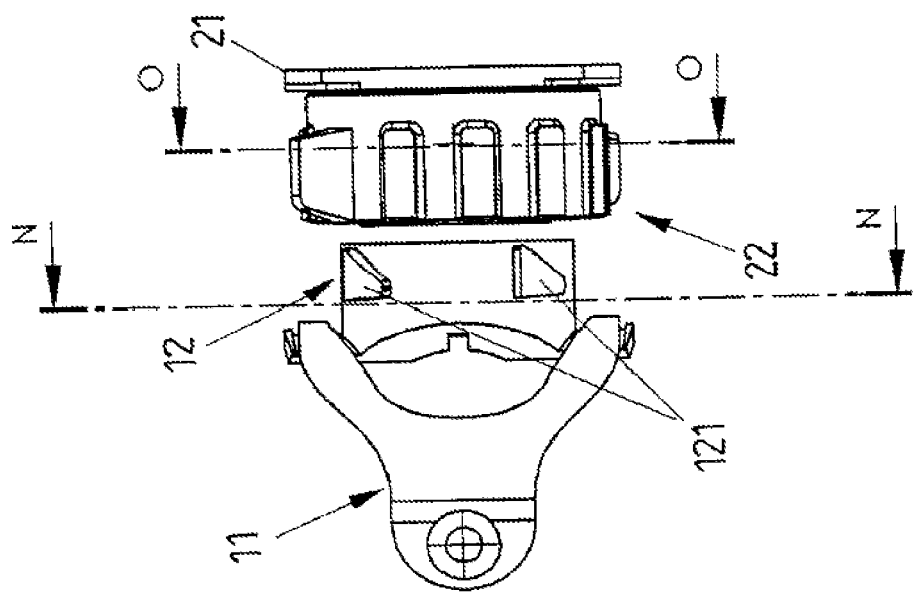

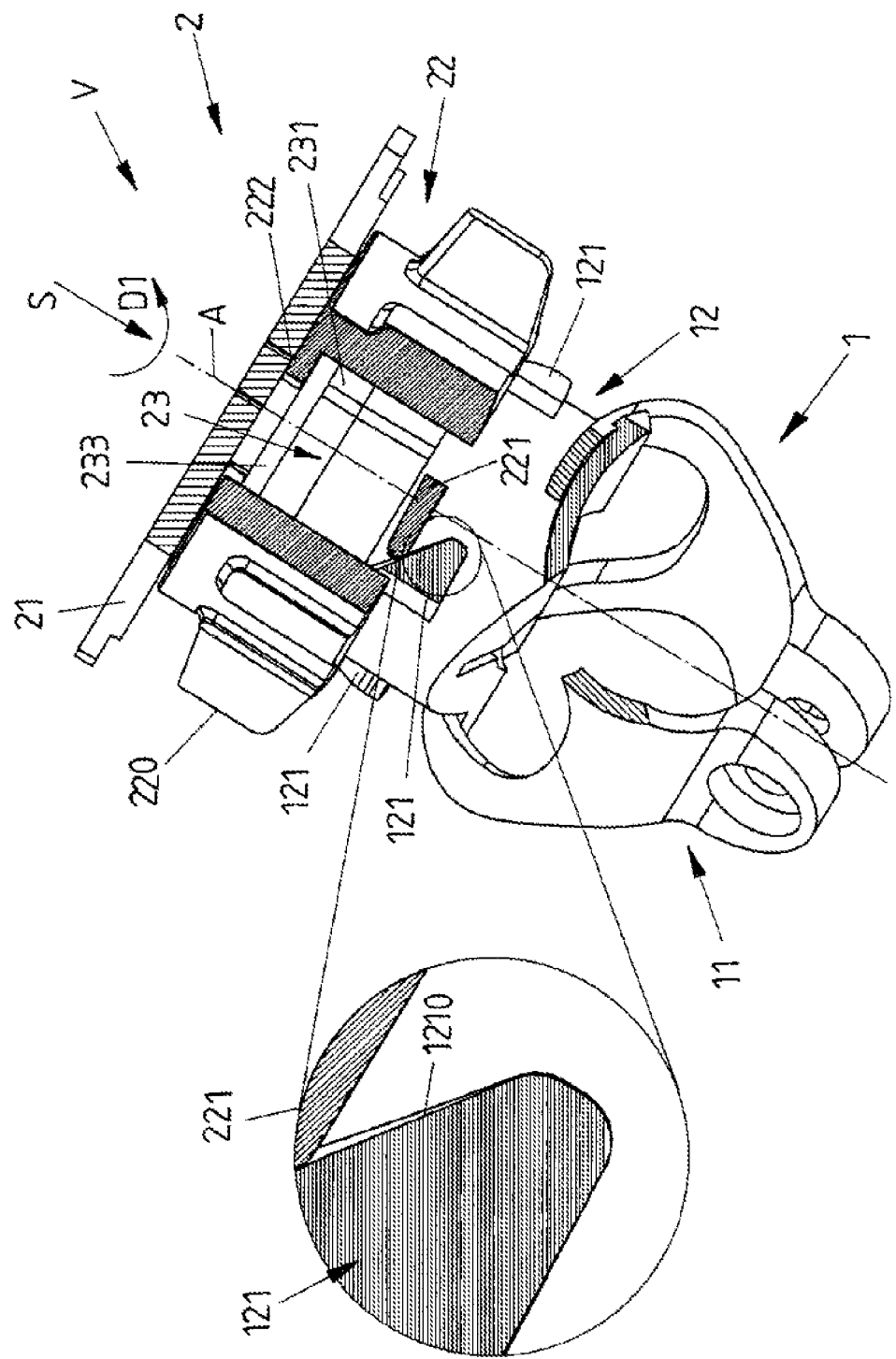

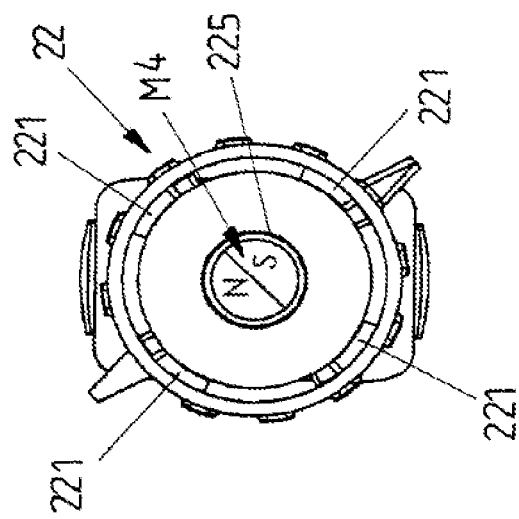
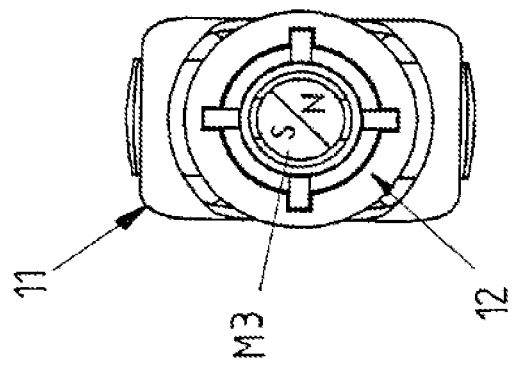
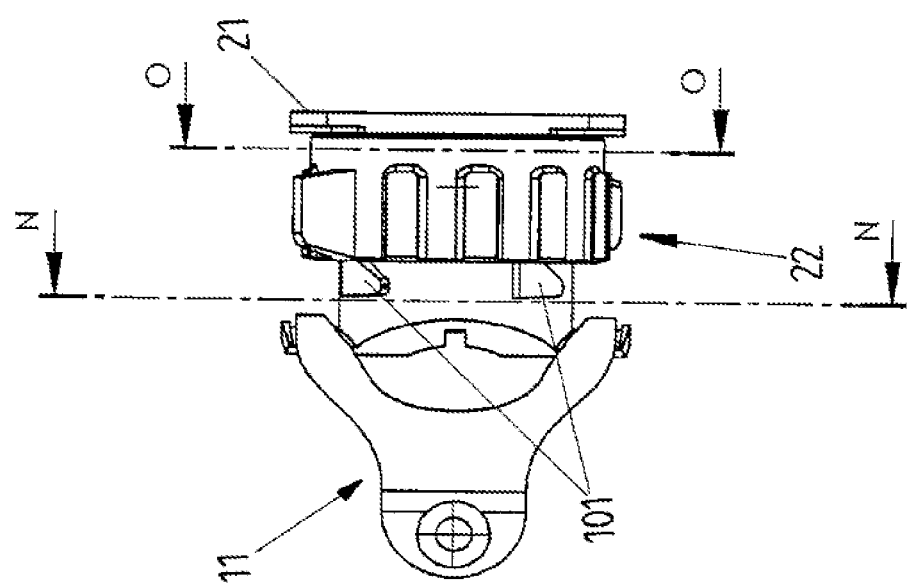

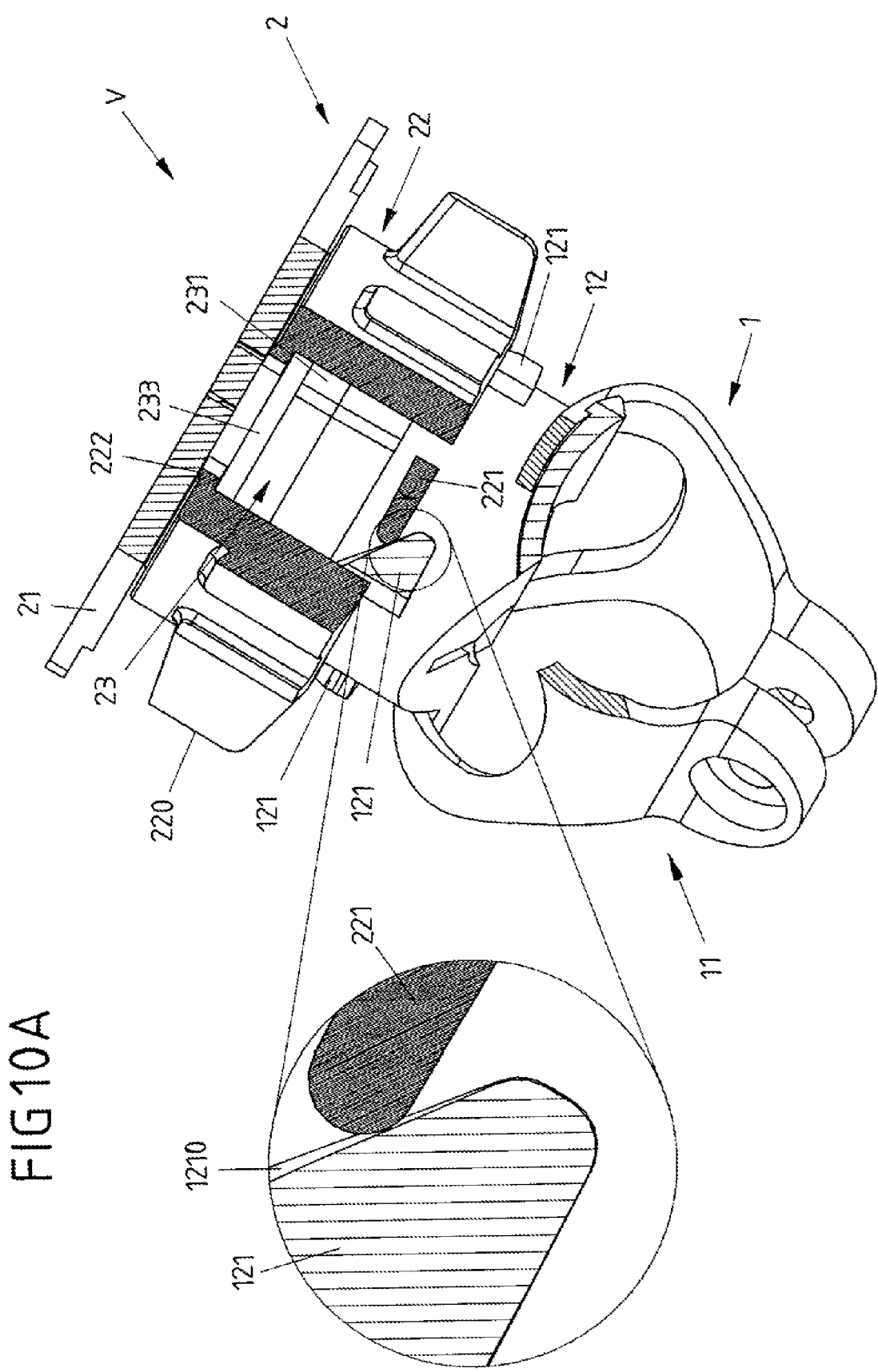

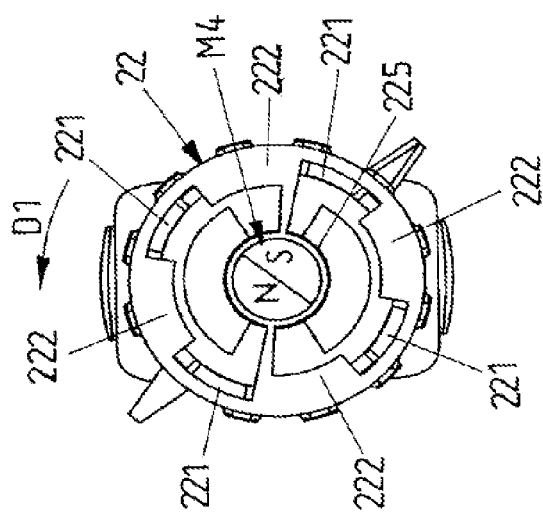
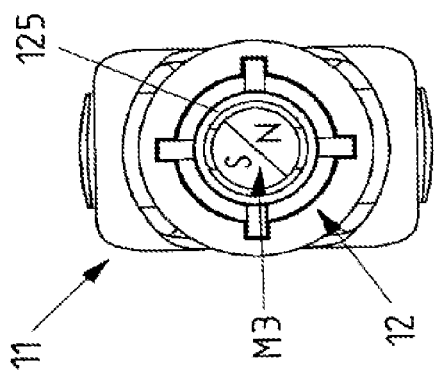
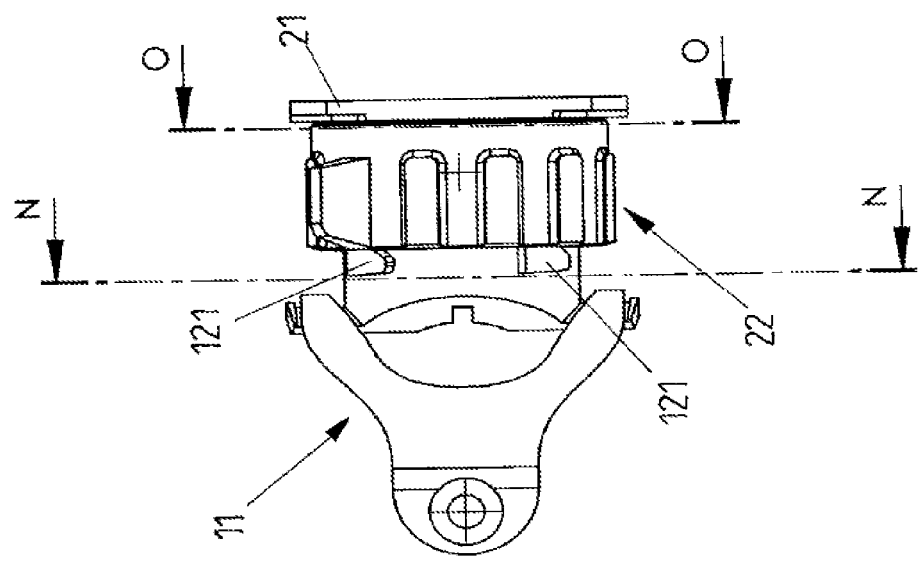

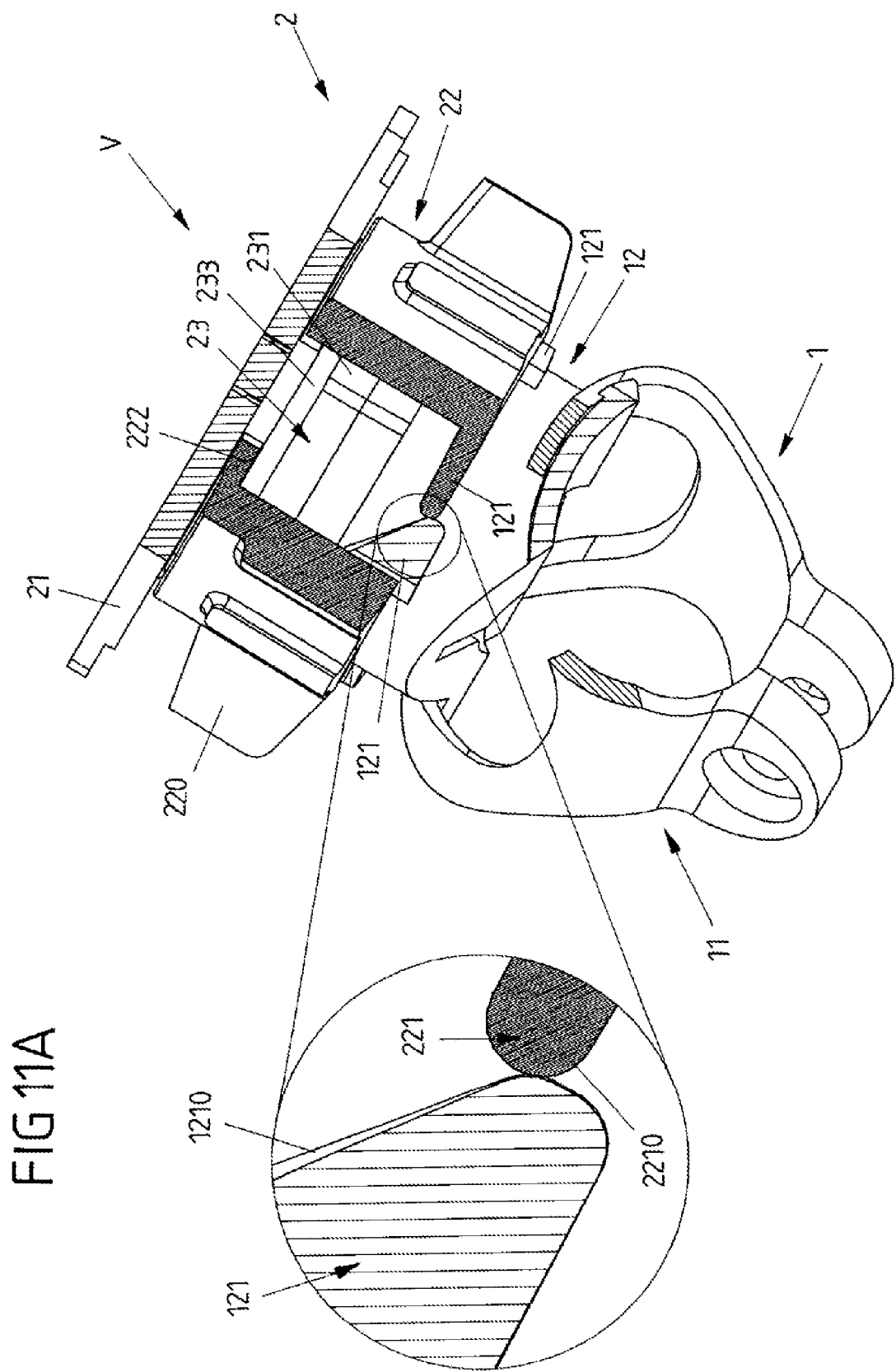

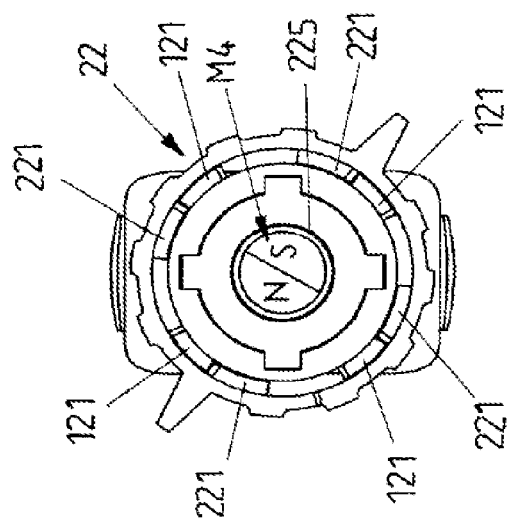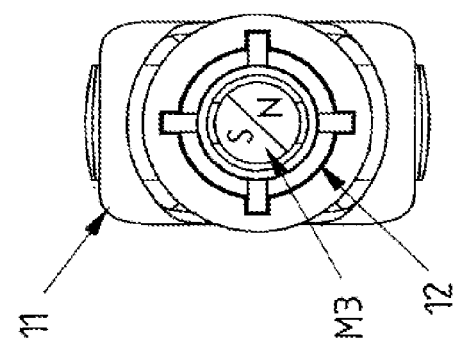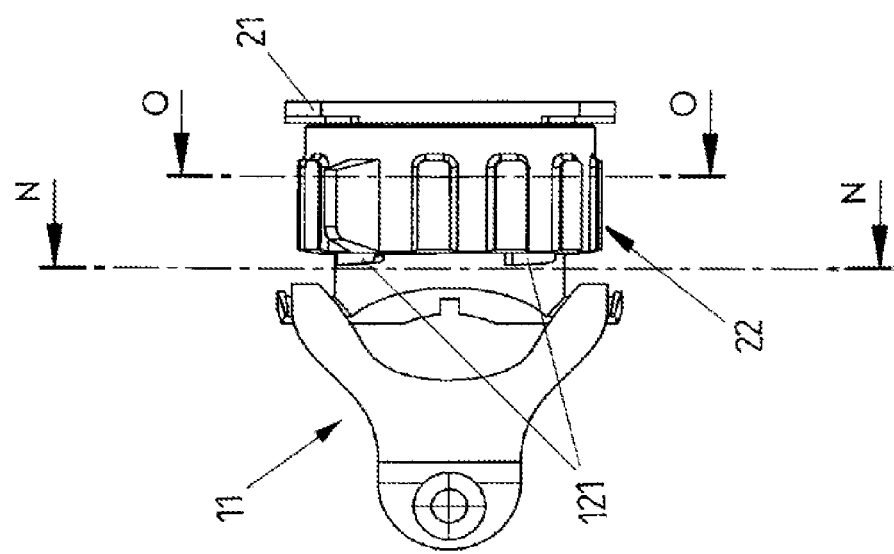

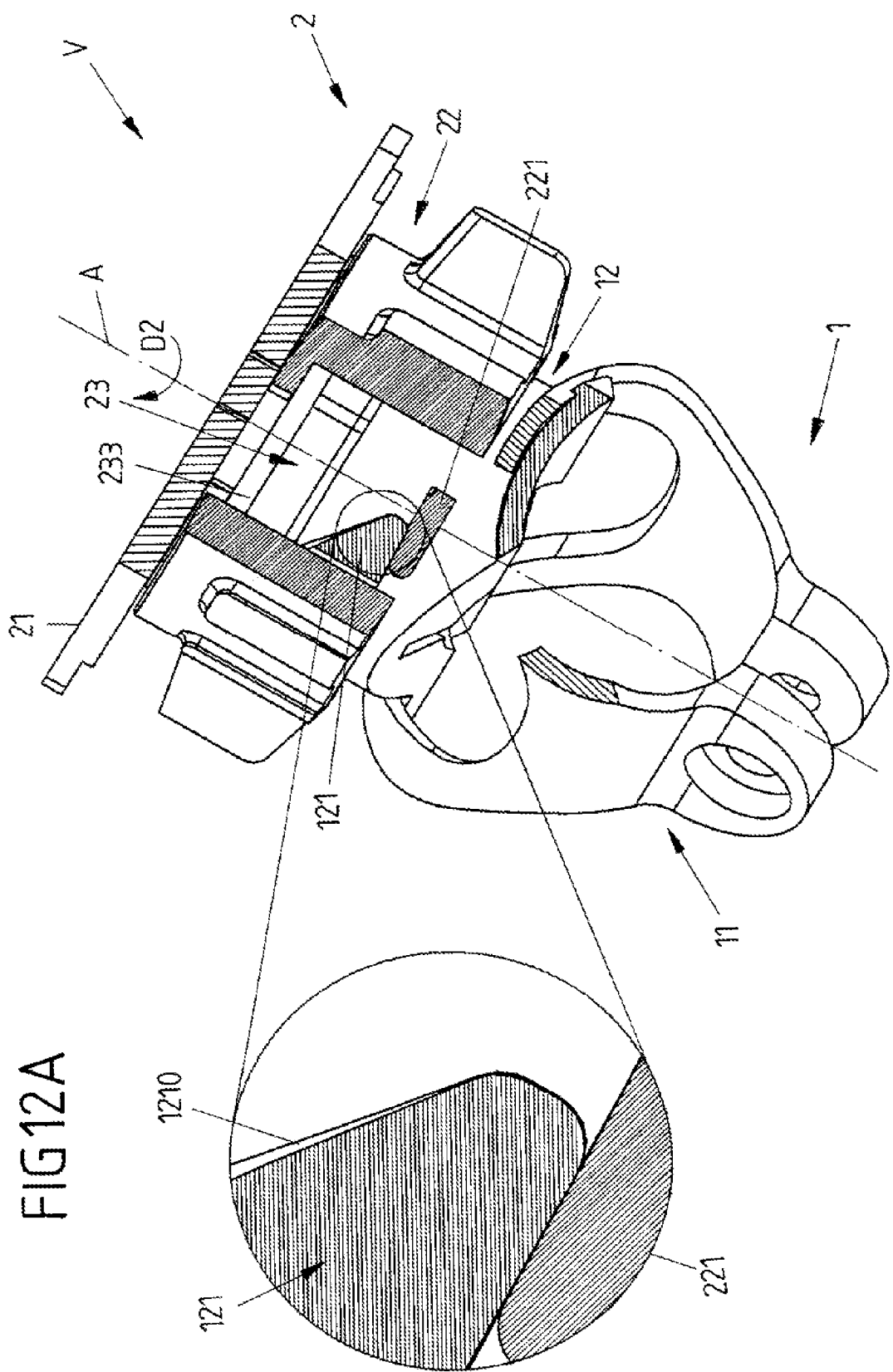

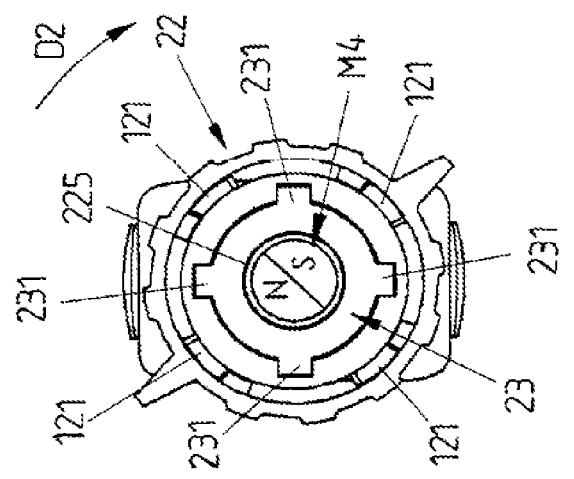
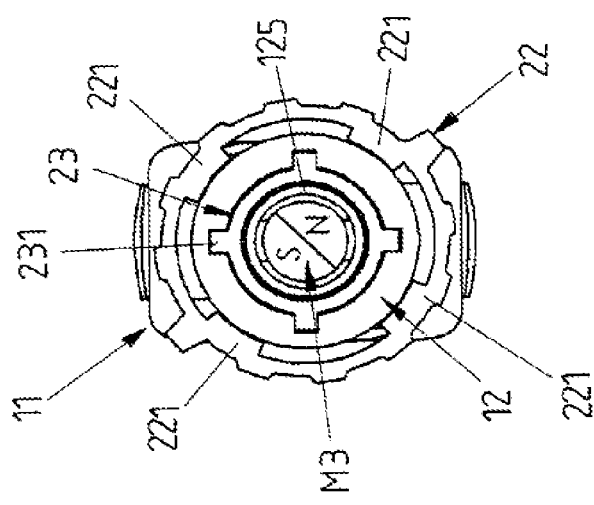
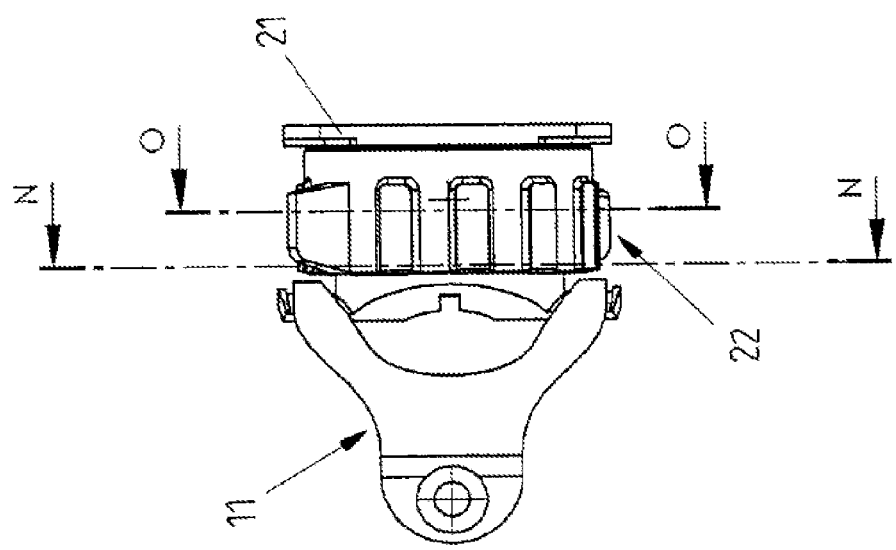

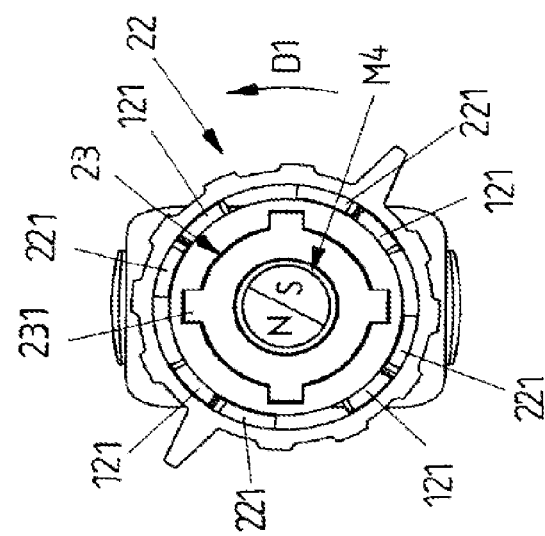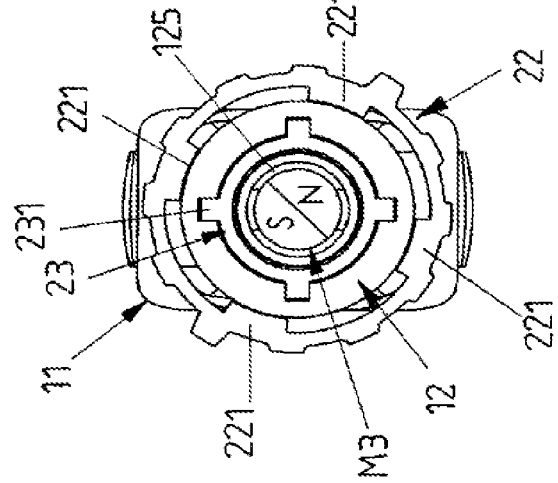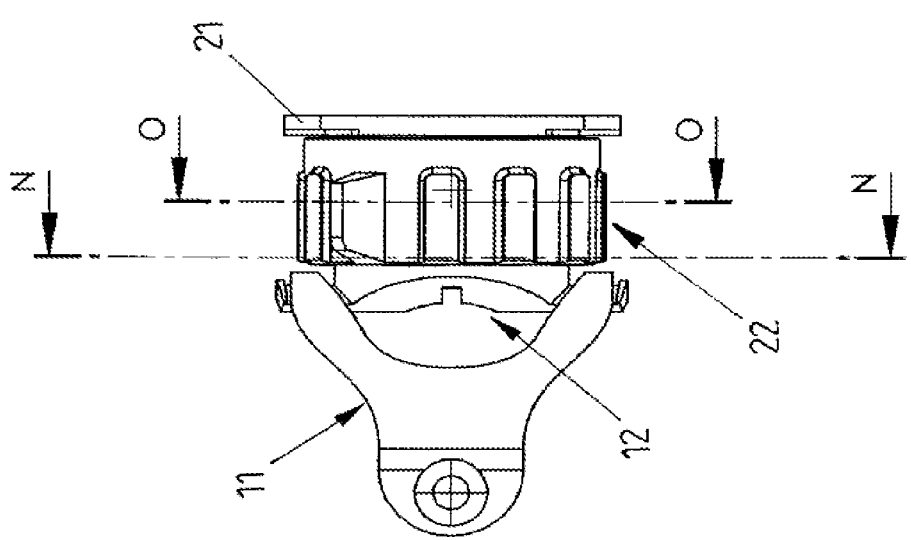

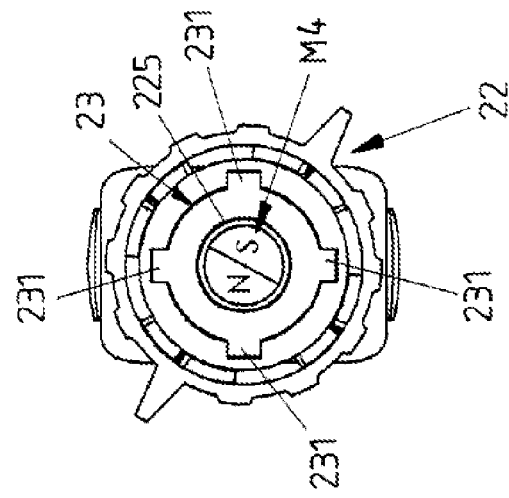
FIG 14D (O-O)
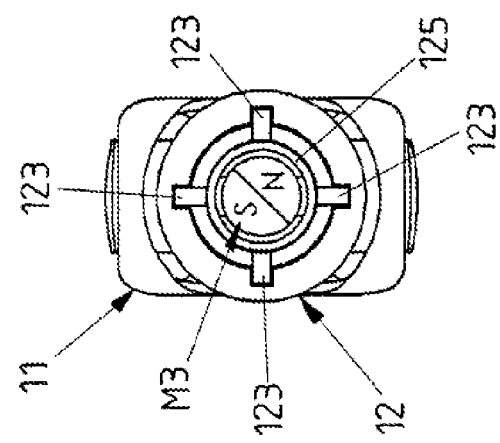
FIG 14C (N-N)
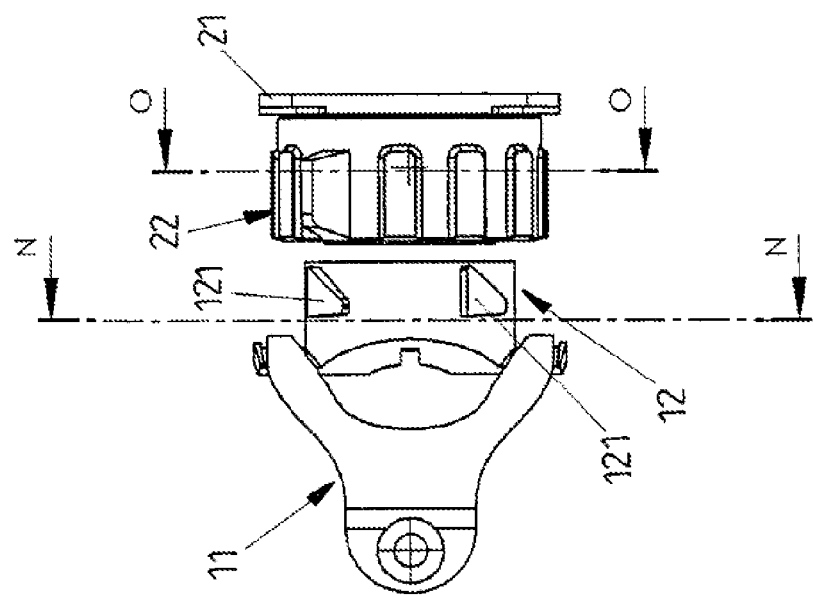
FIG 14B

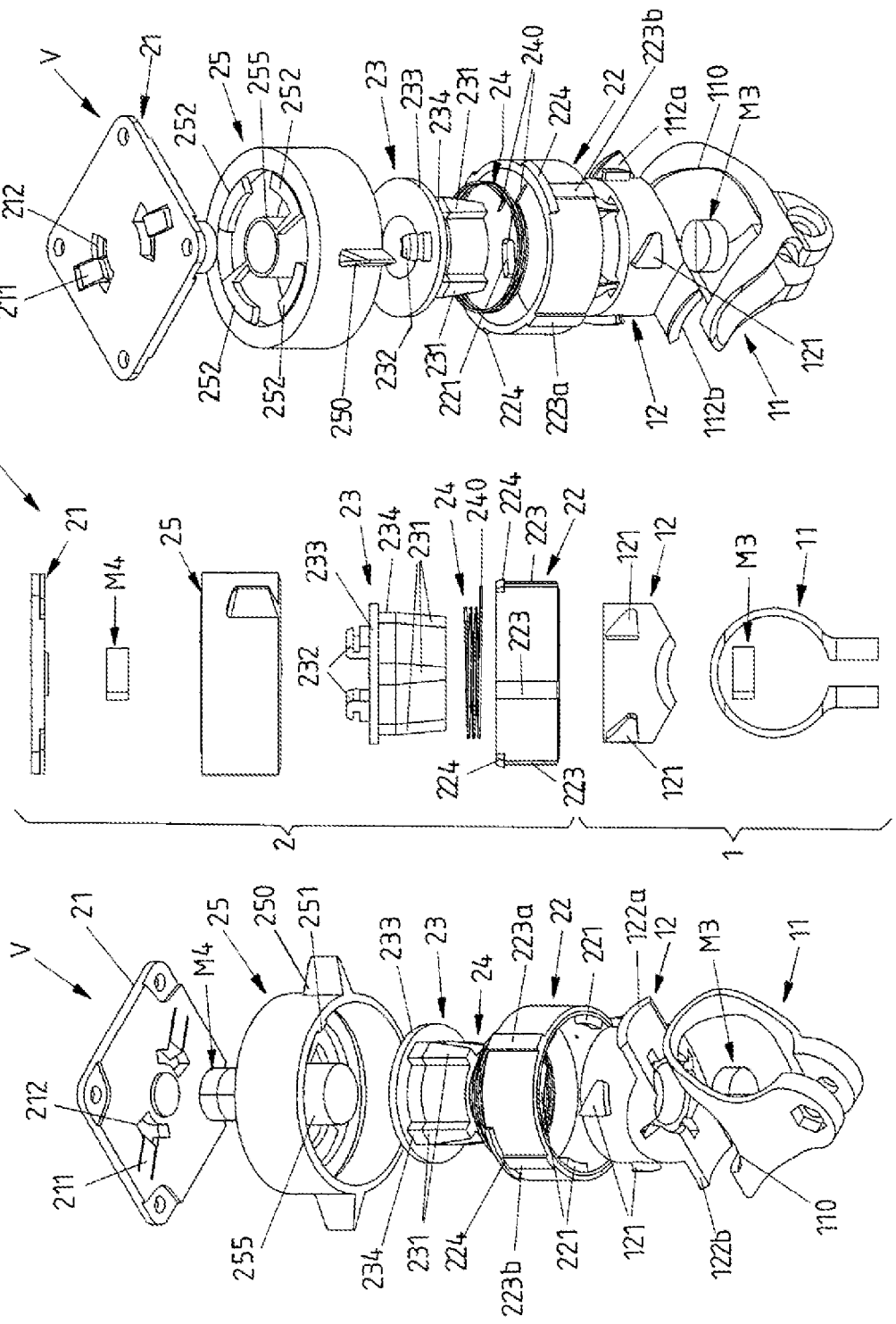

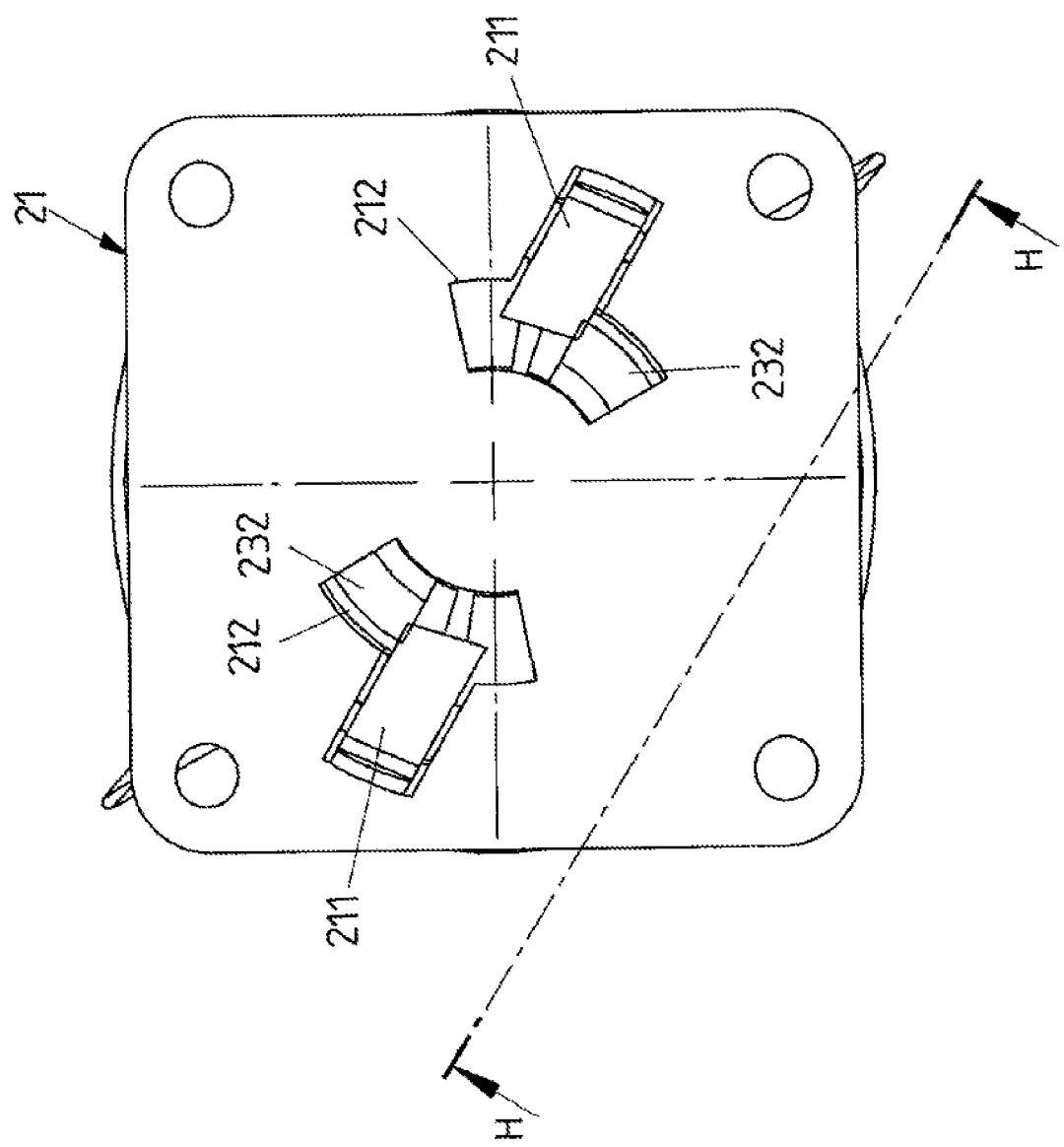

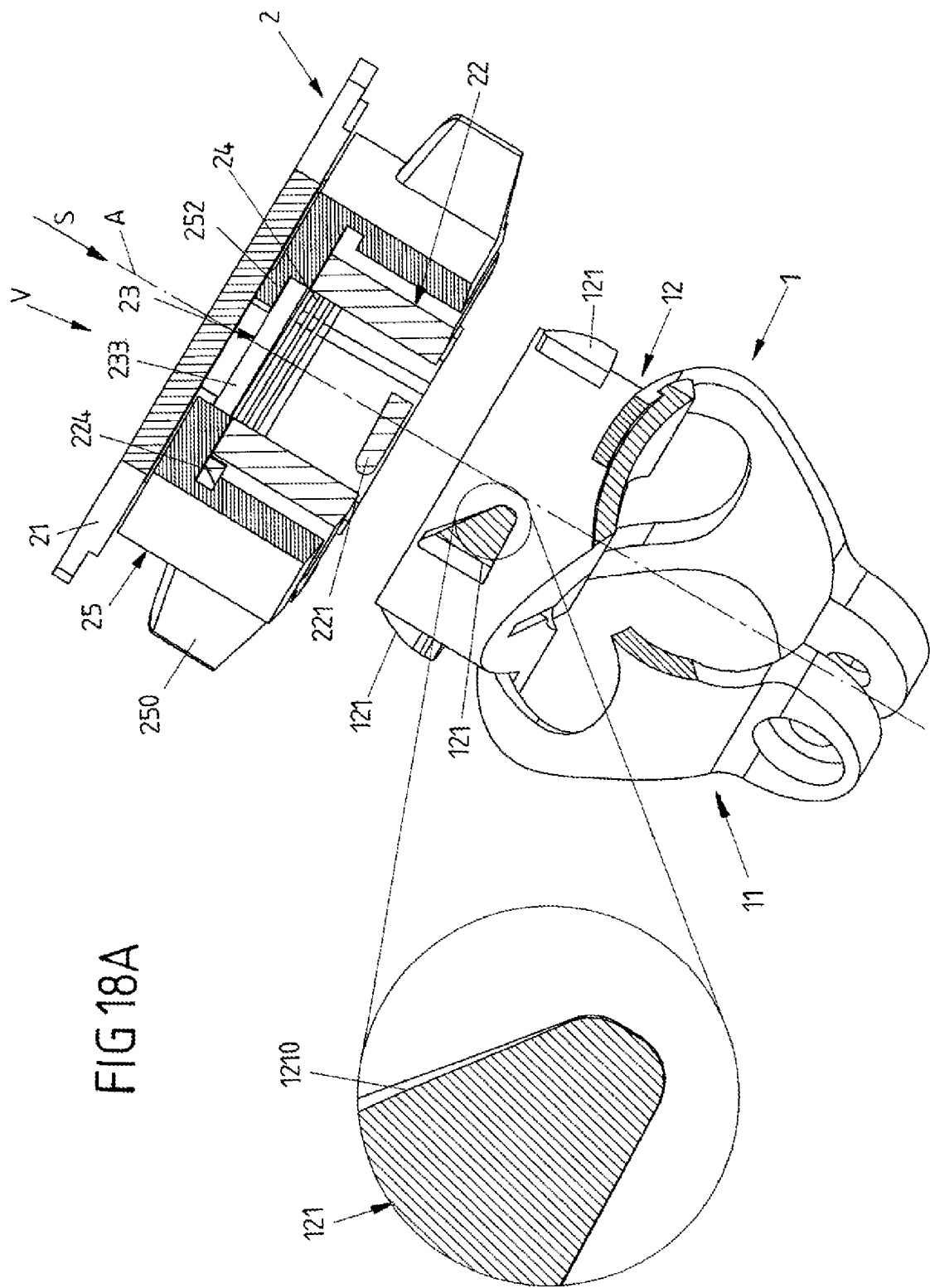

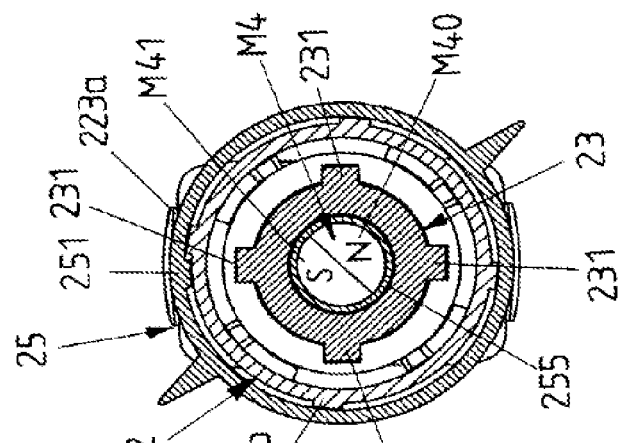
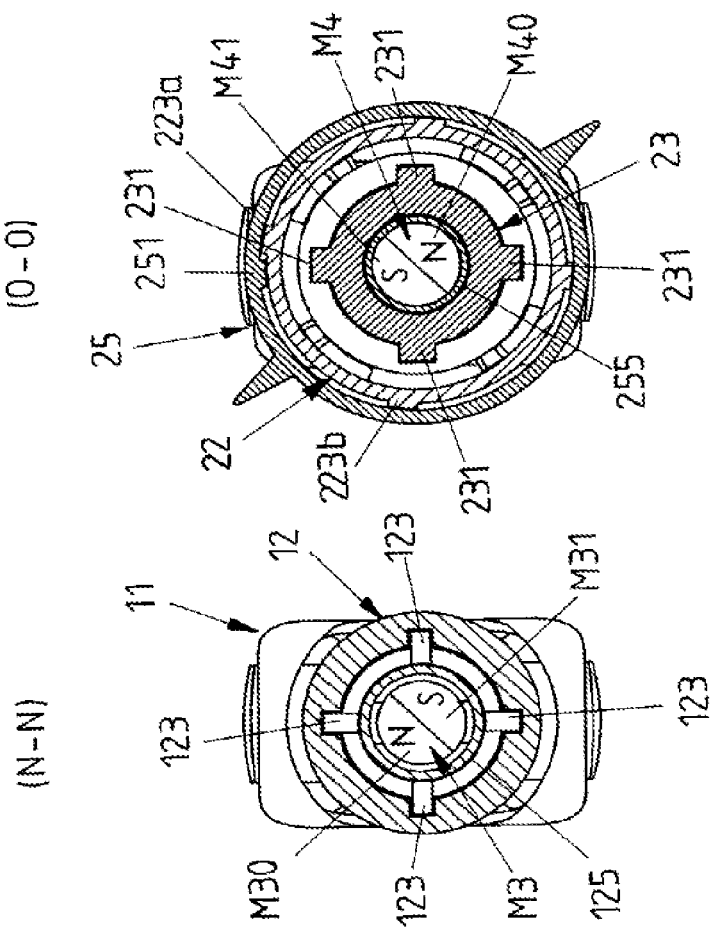
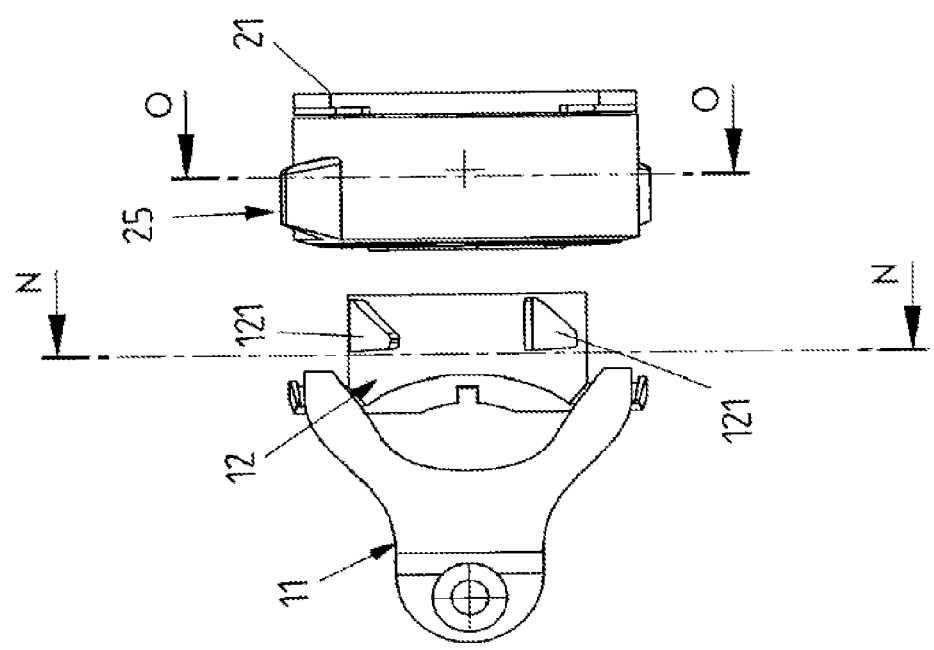

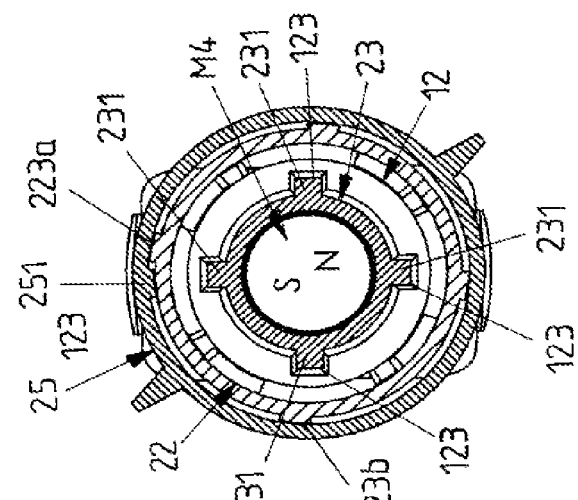
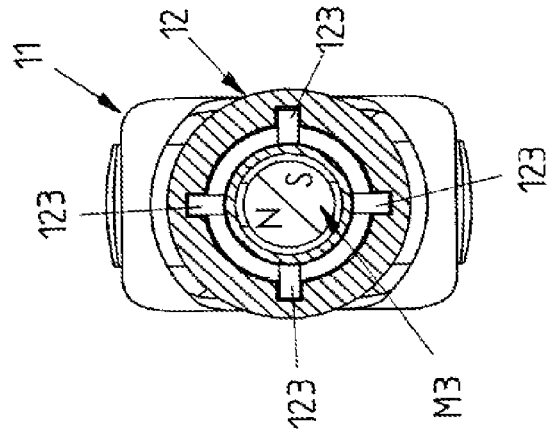
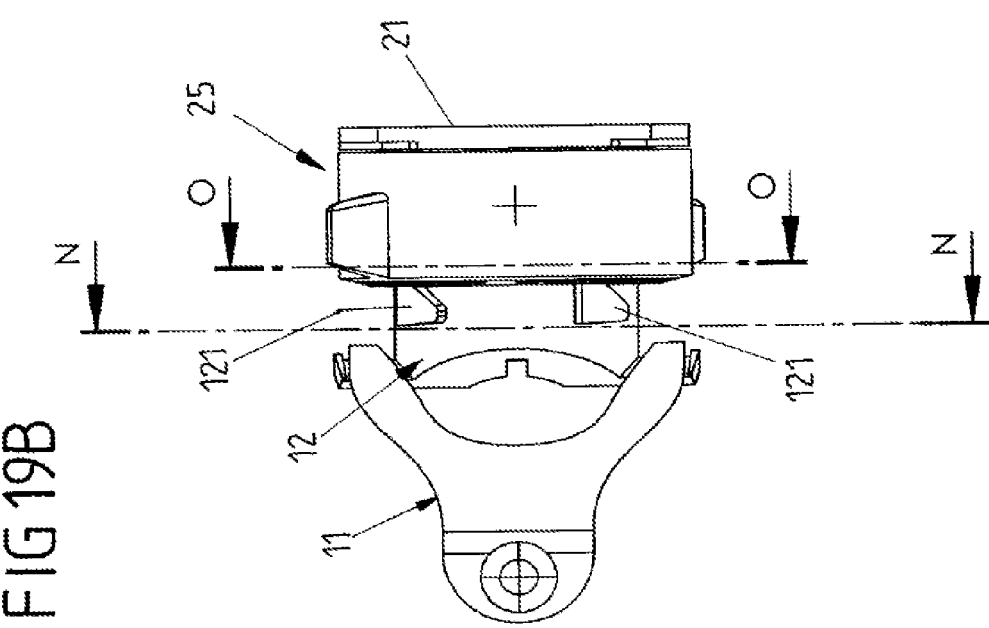

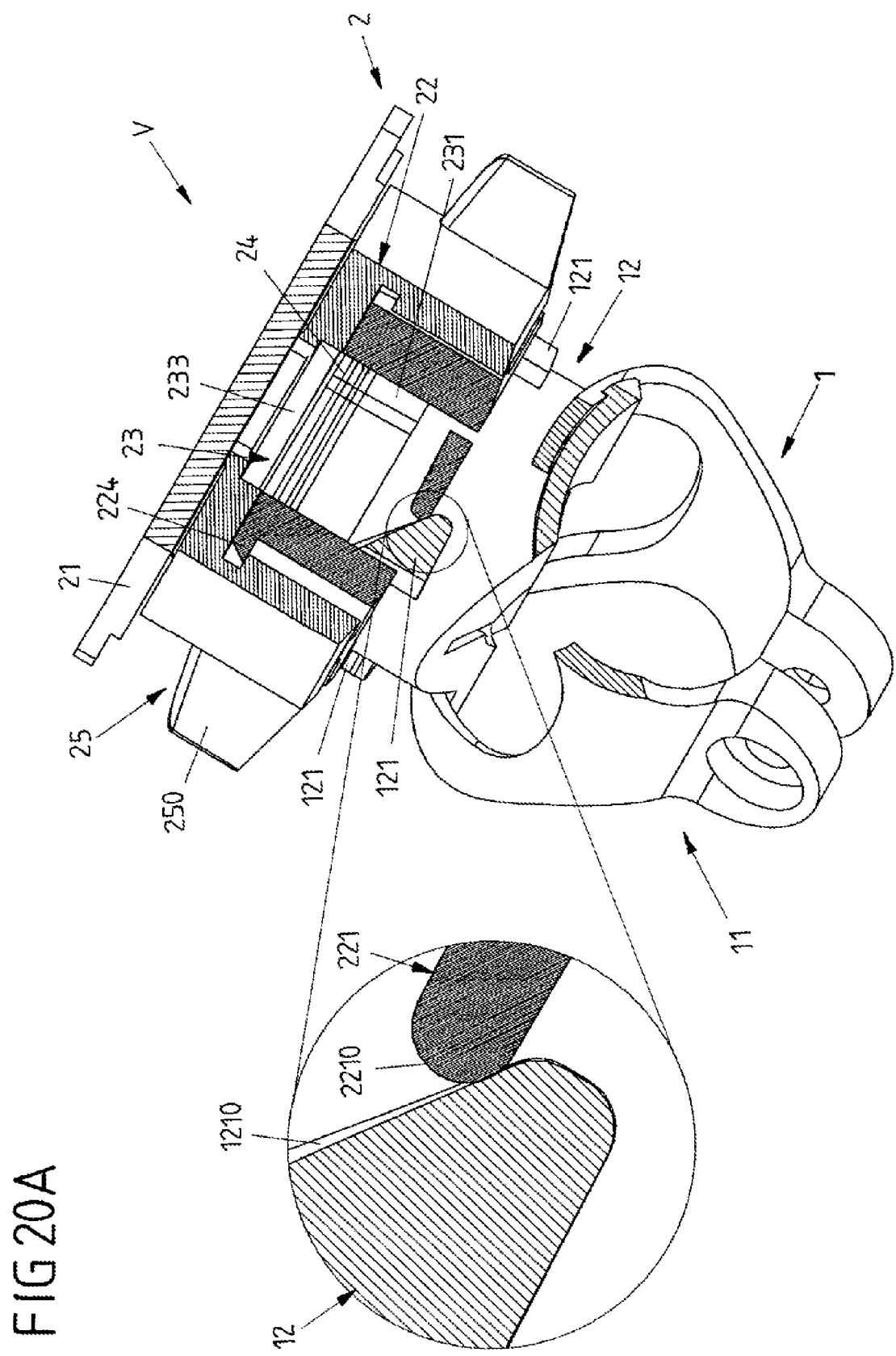

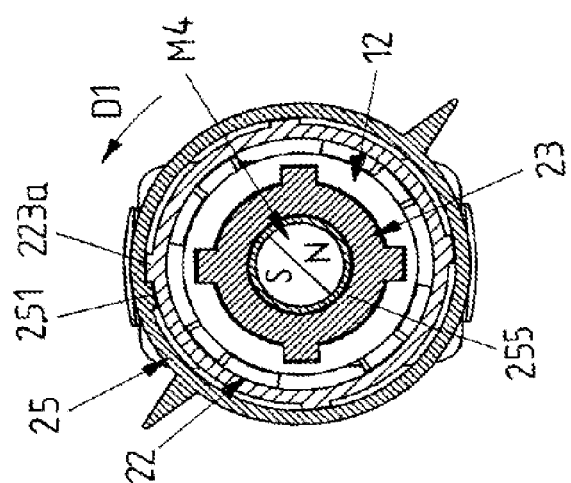
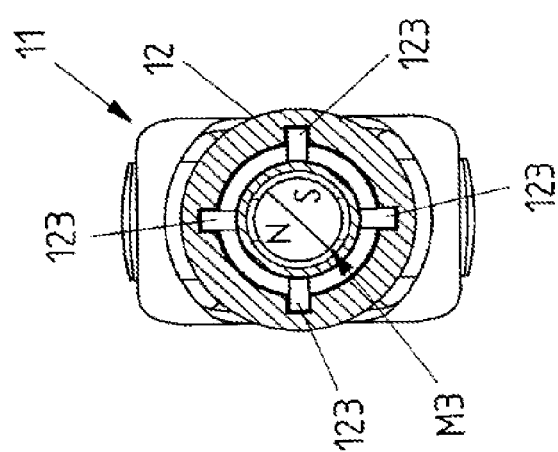
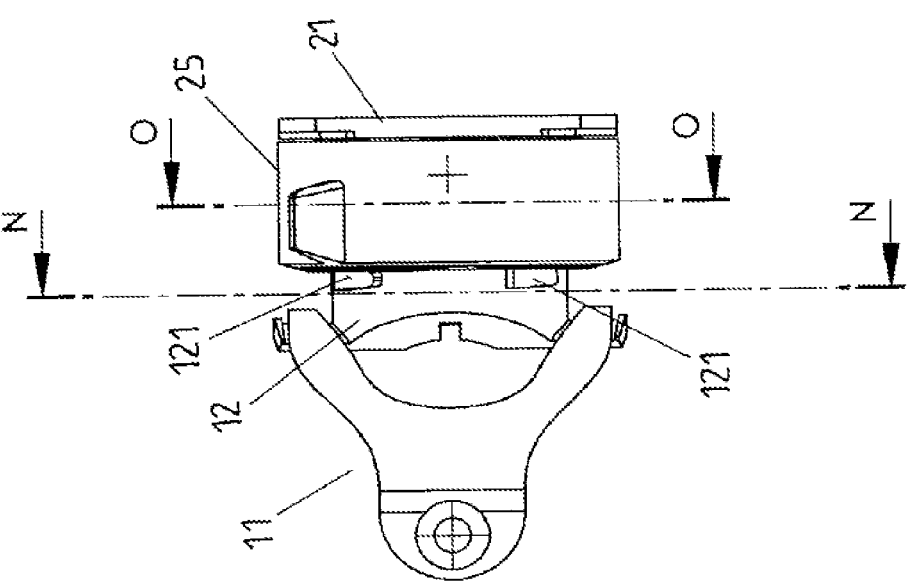

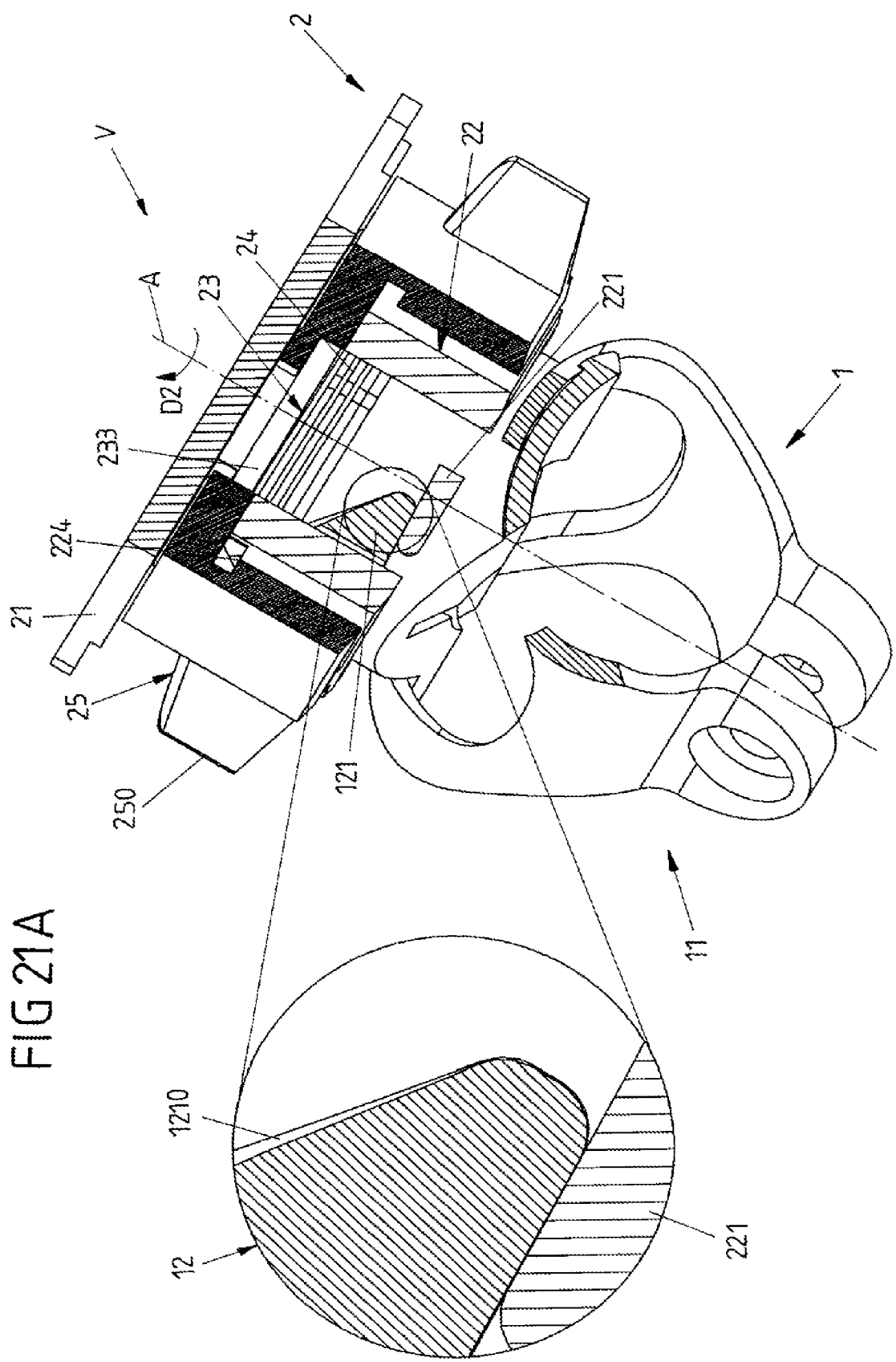

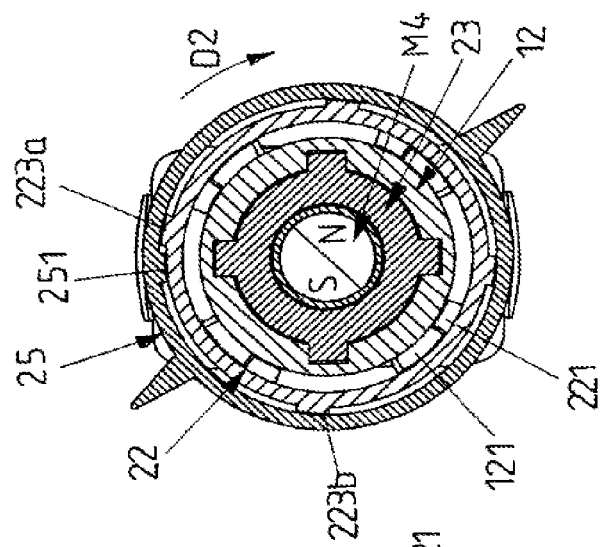
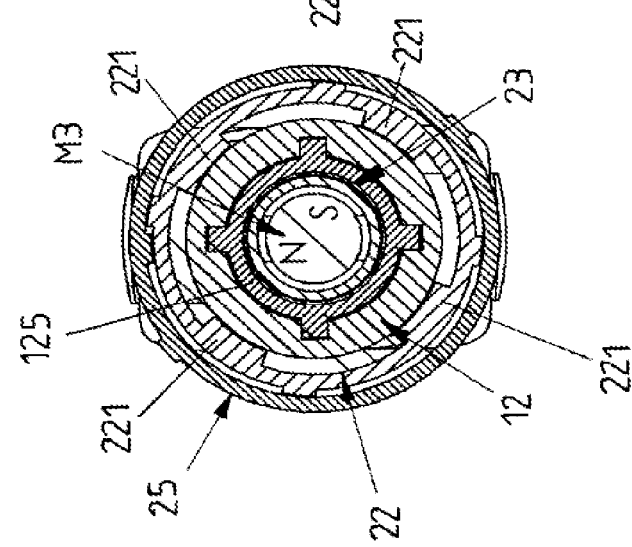
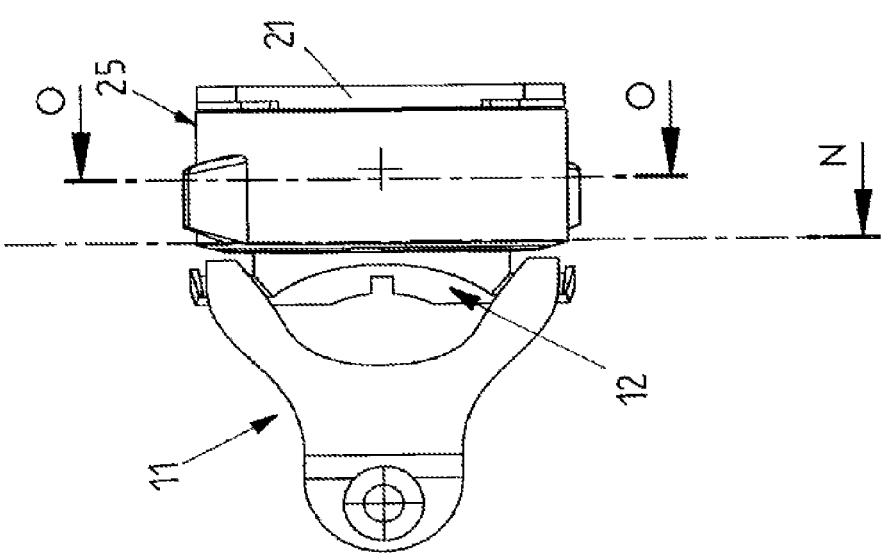

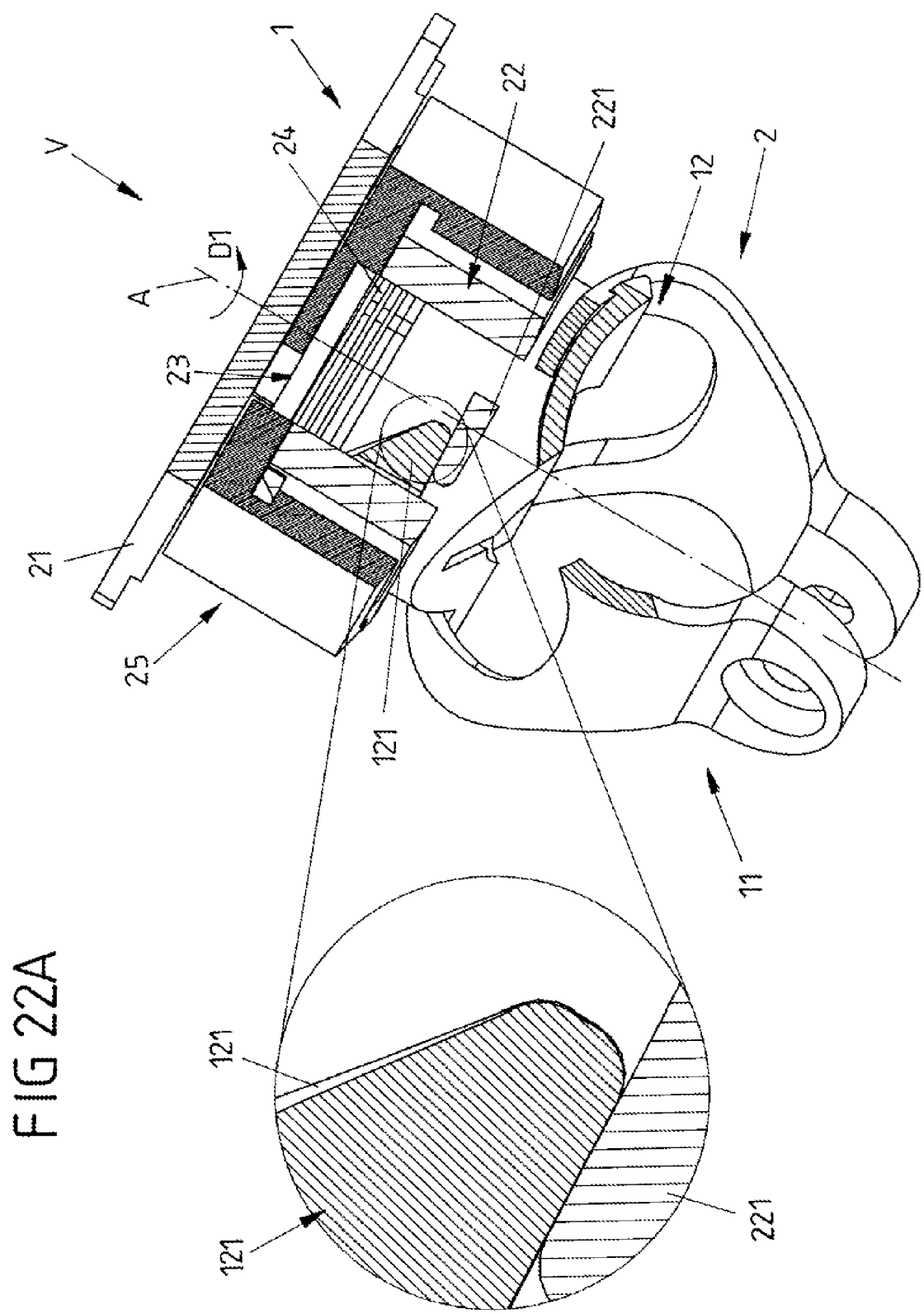

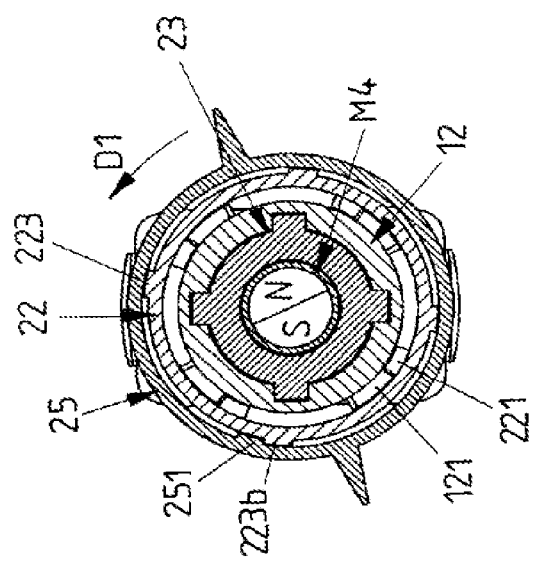
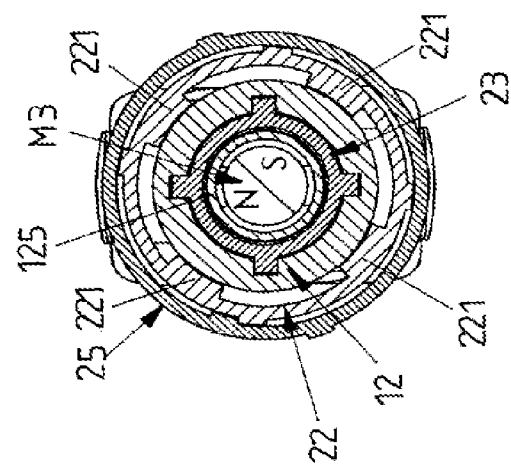
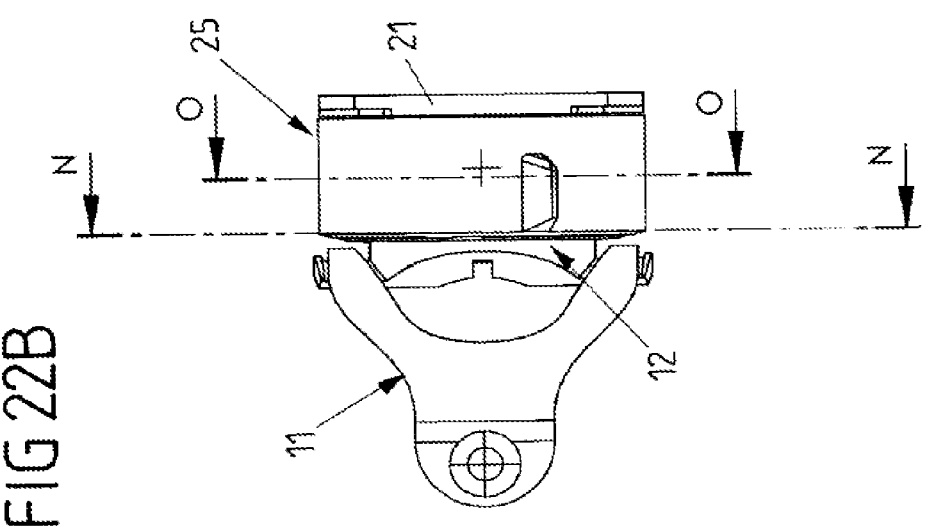

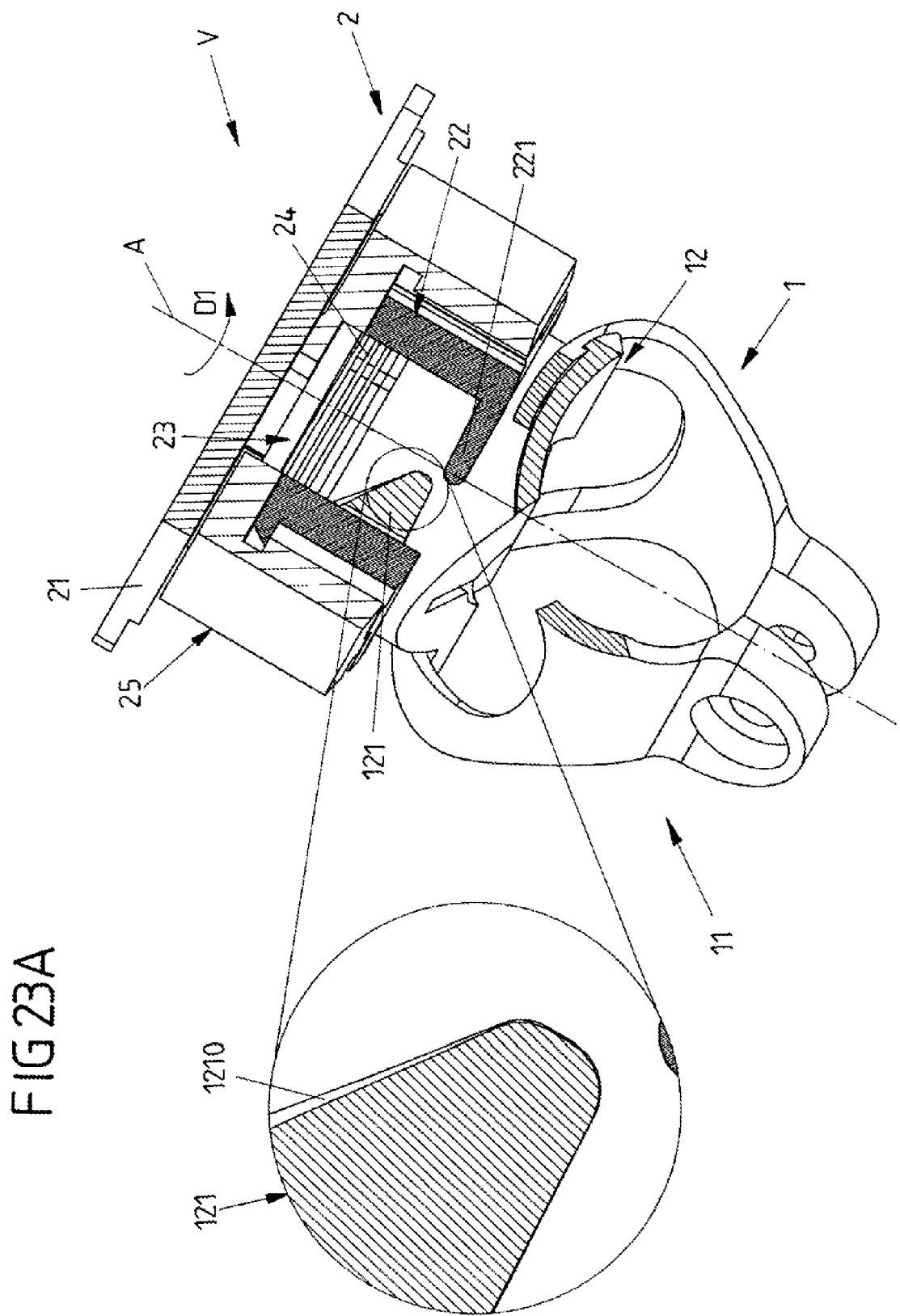

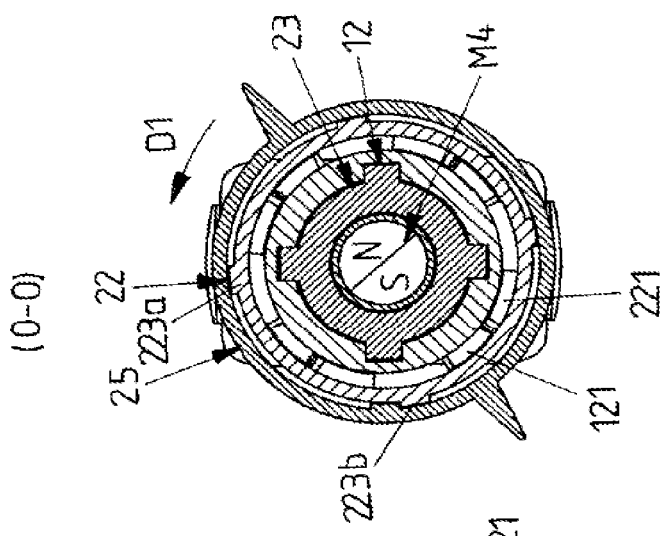
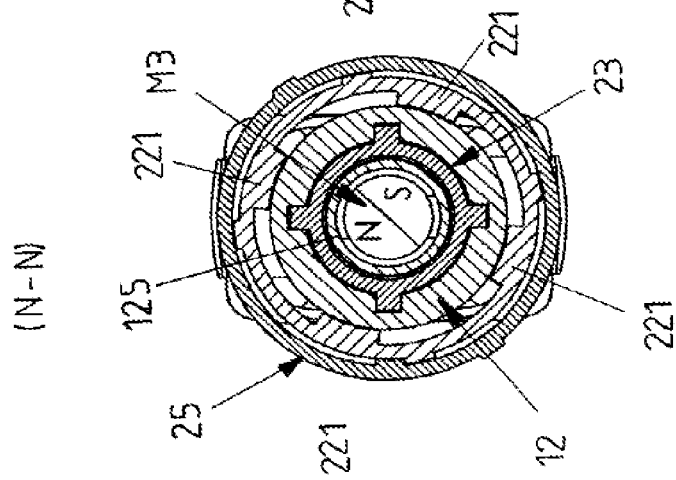
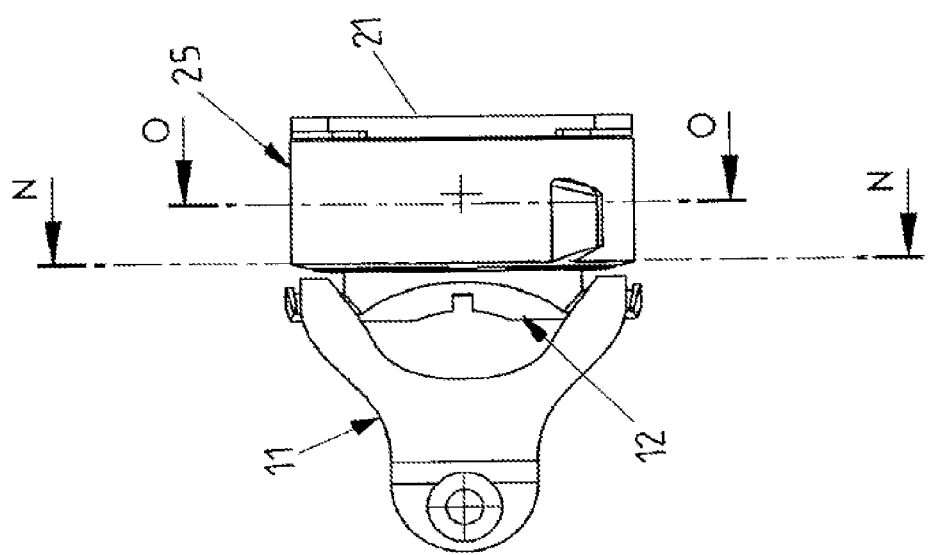

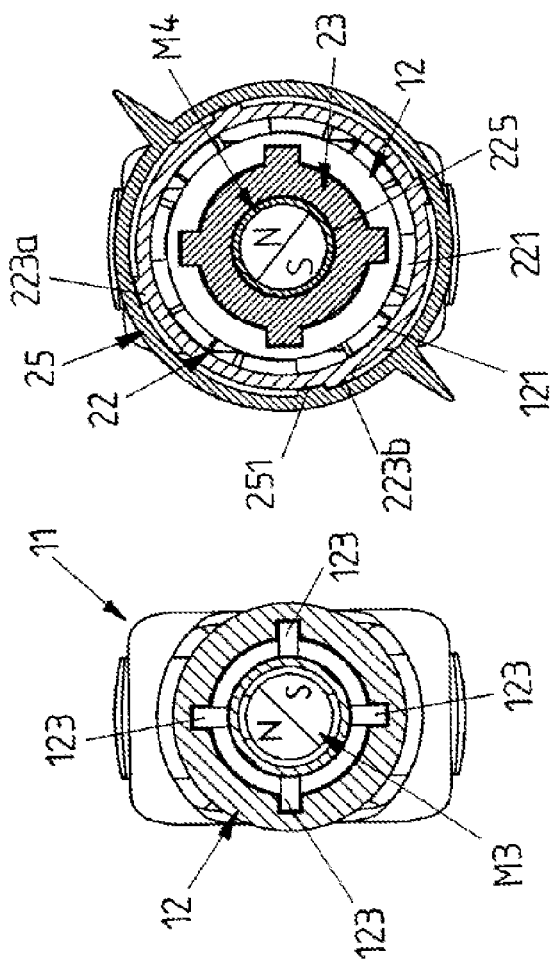
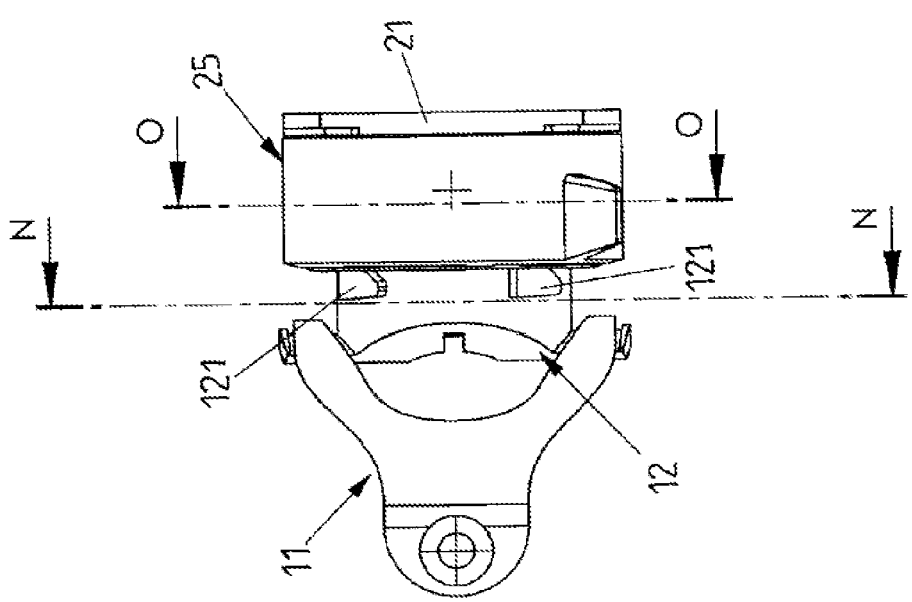

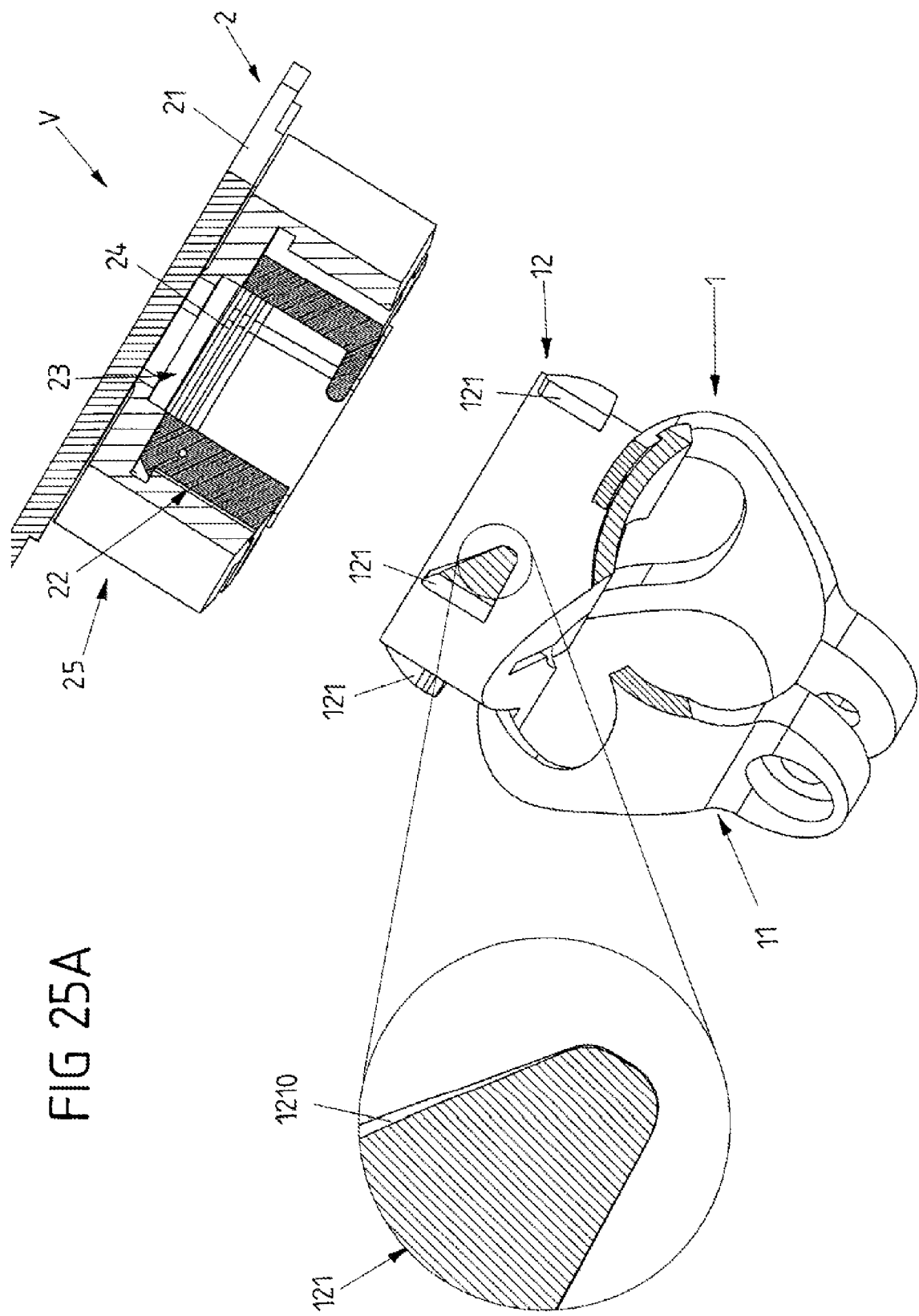

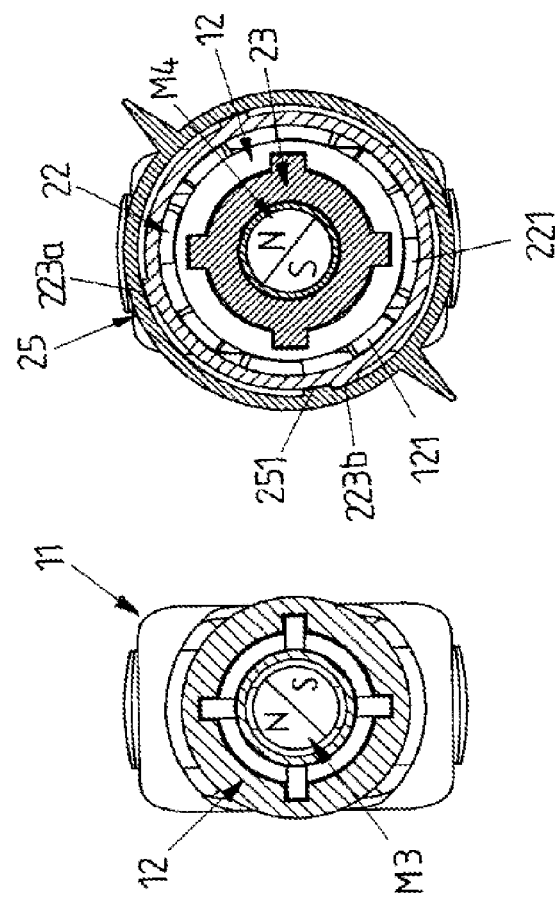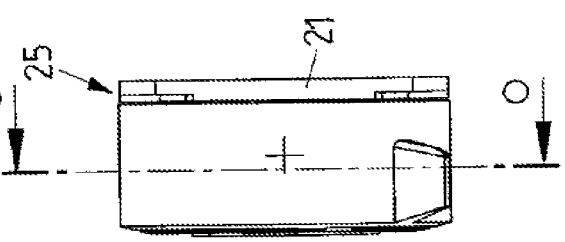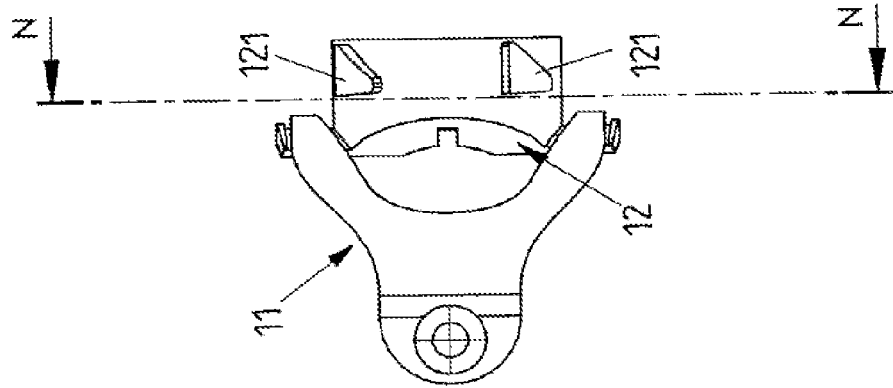

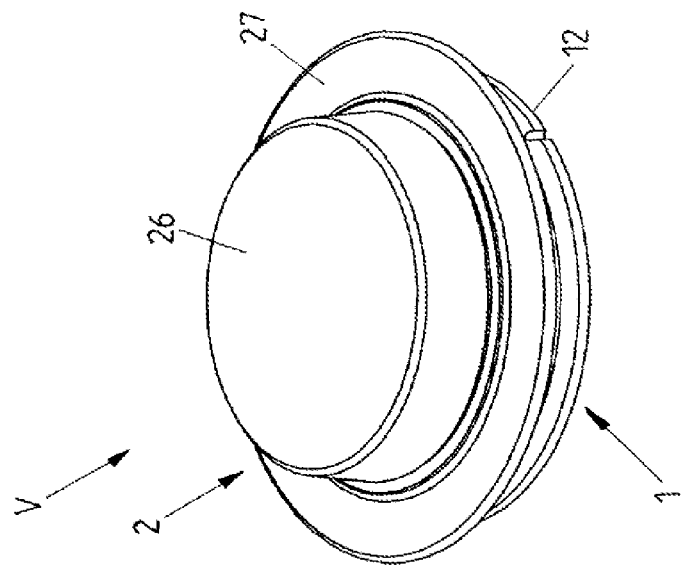
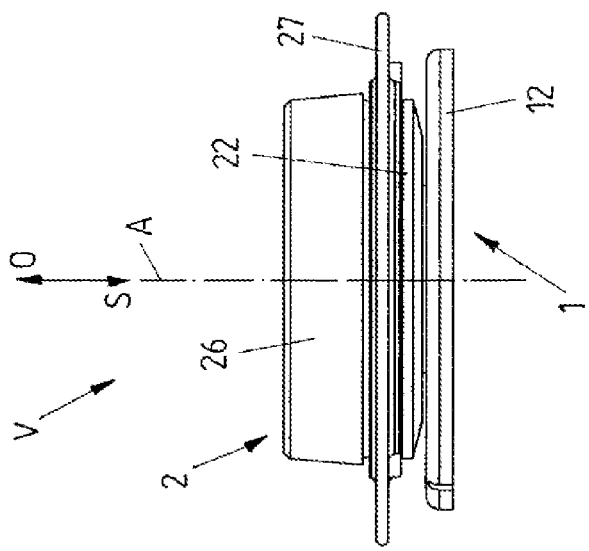
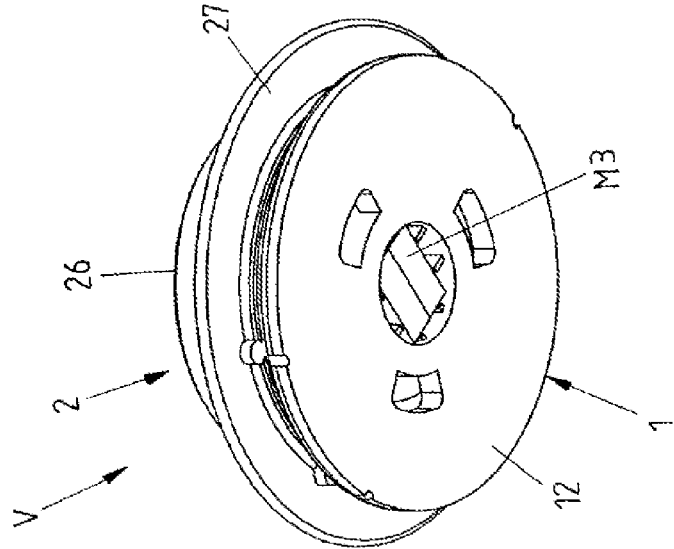

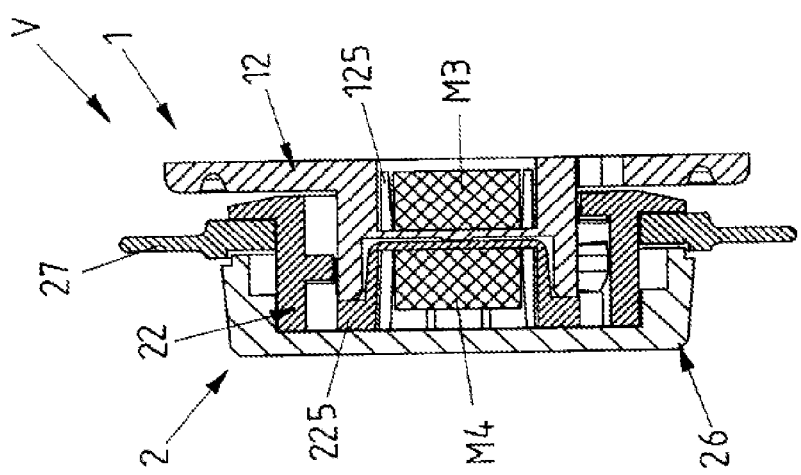
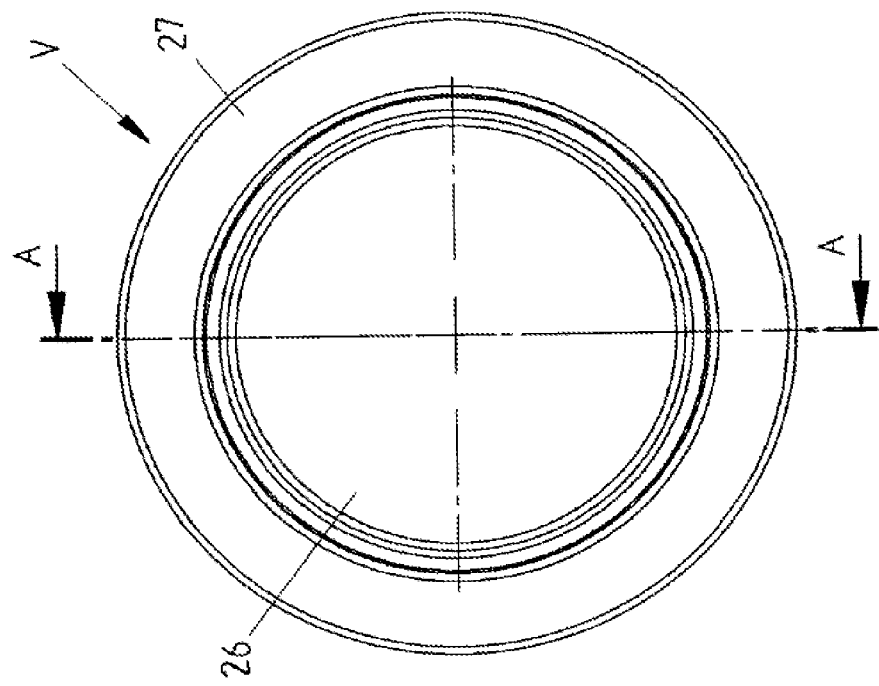

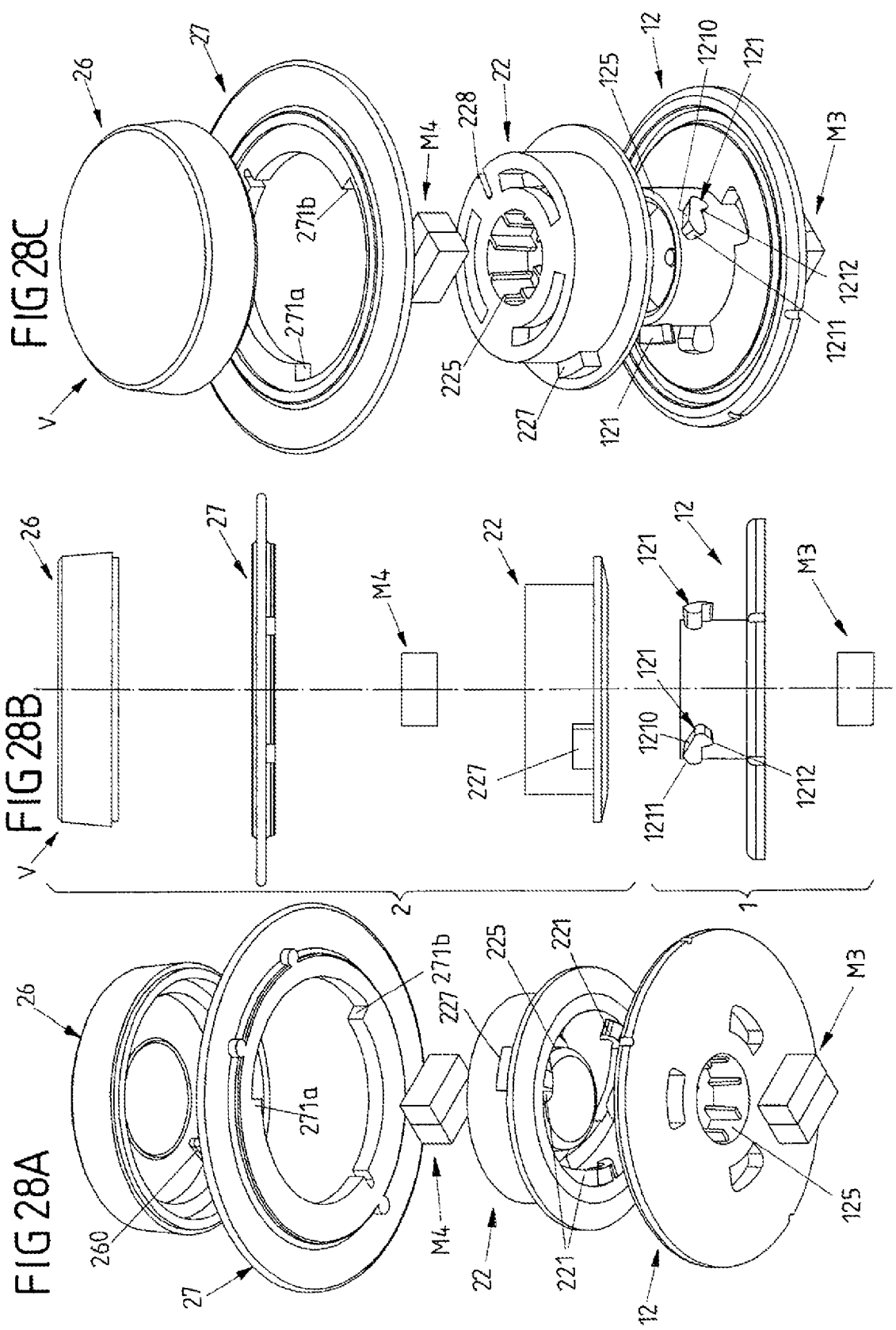

(B-B)

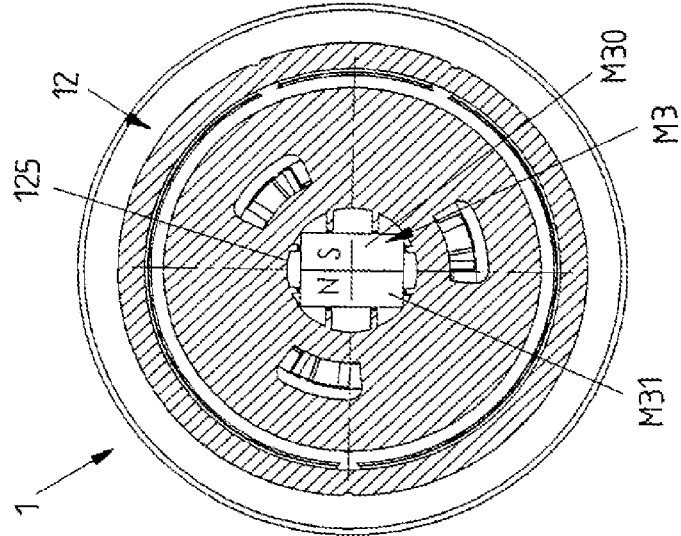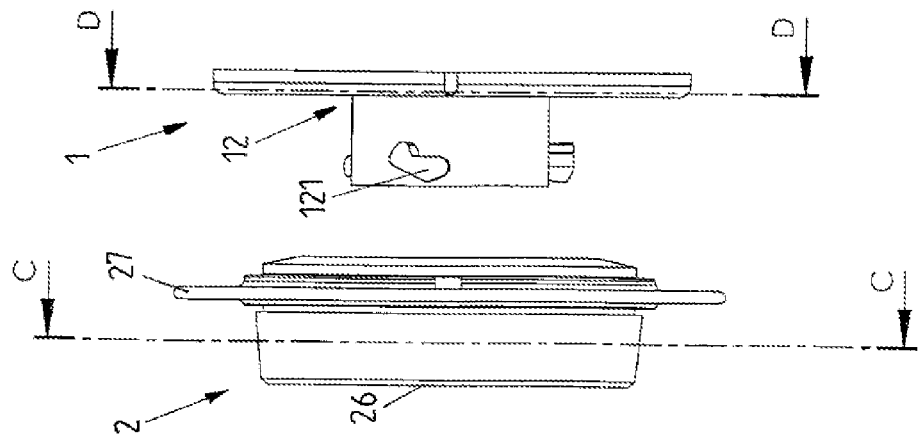

(B-B)

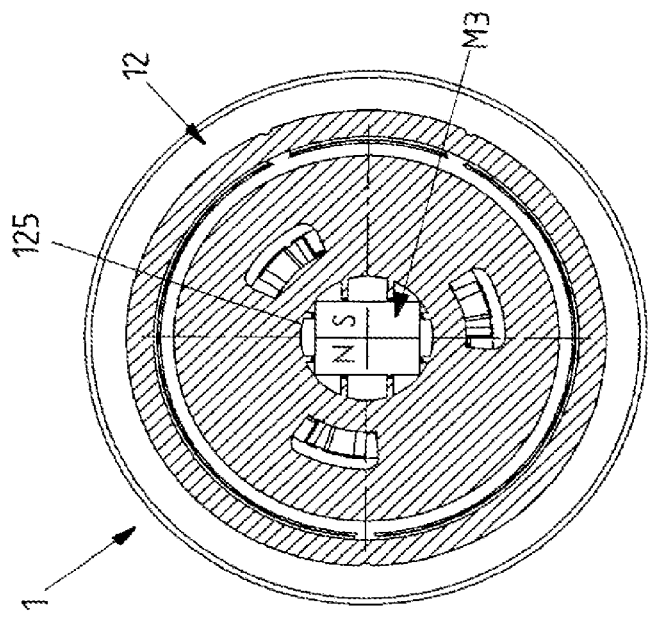
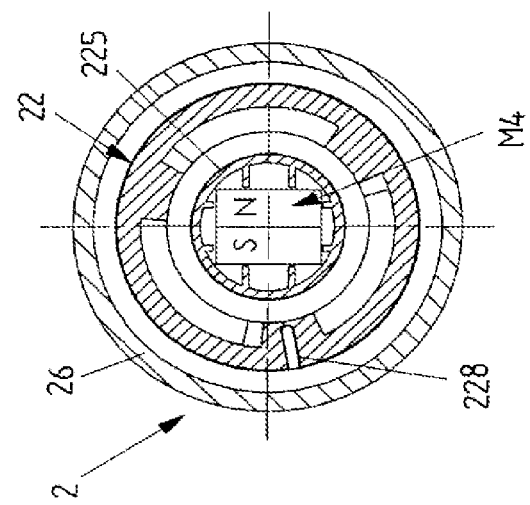
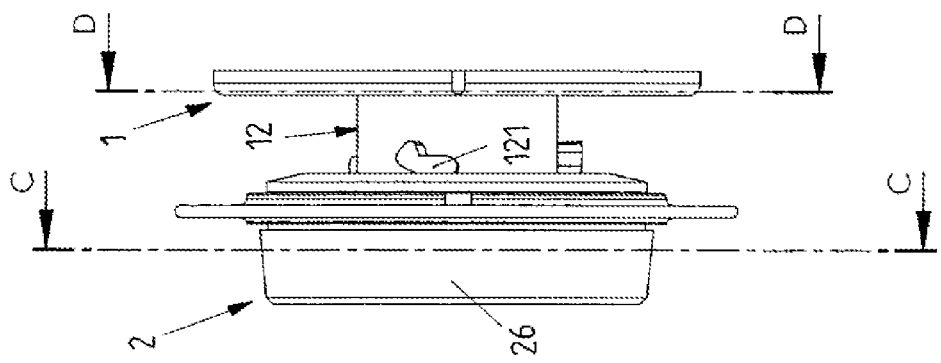

(B-B)

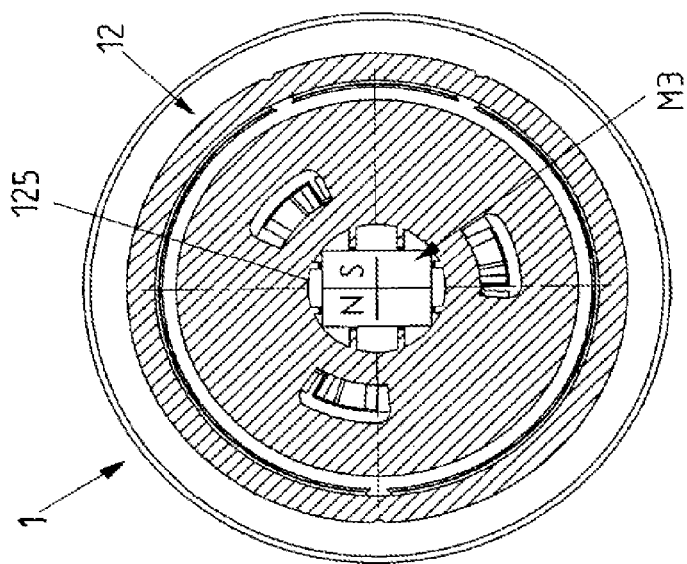
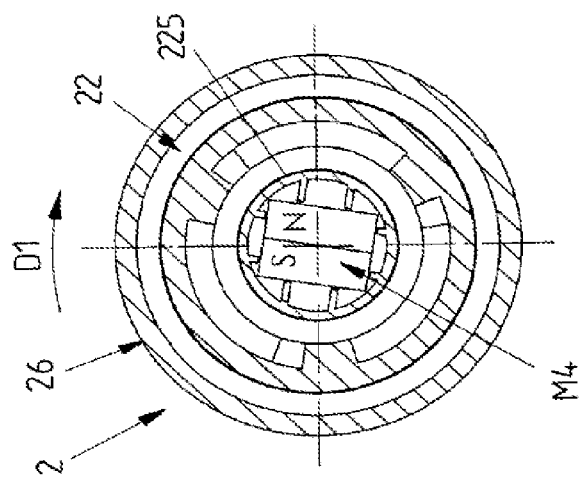
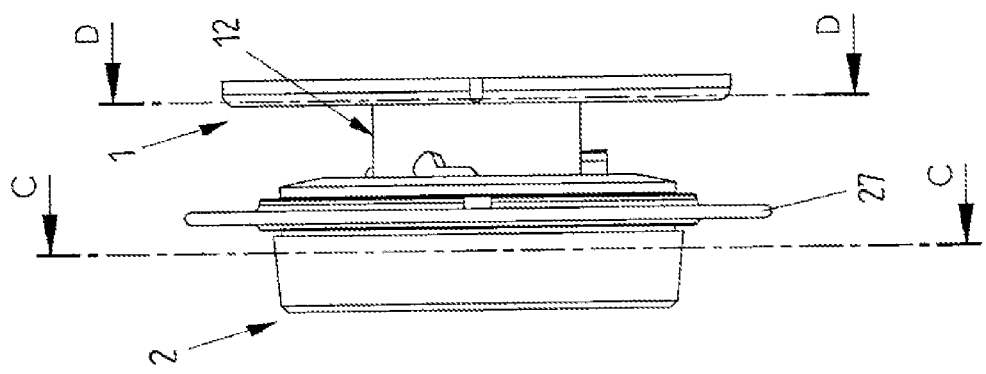

(B-B)

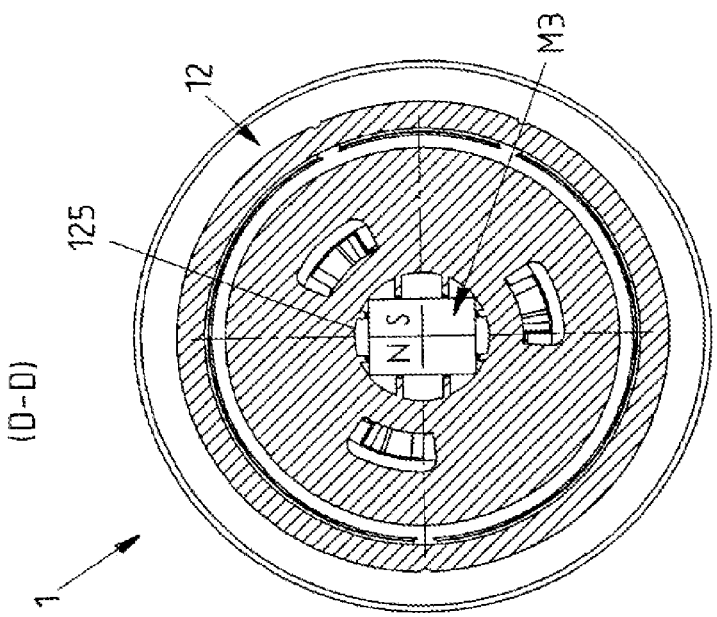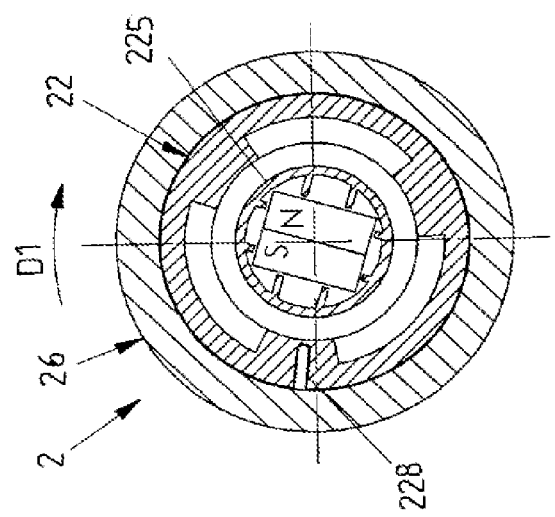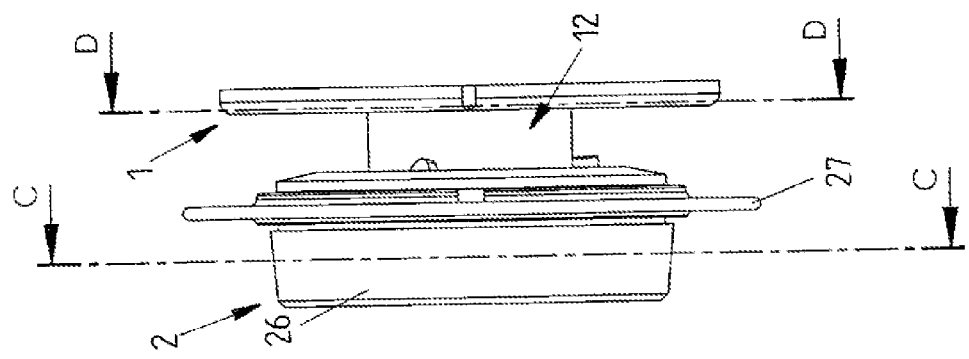

(B-B)

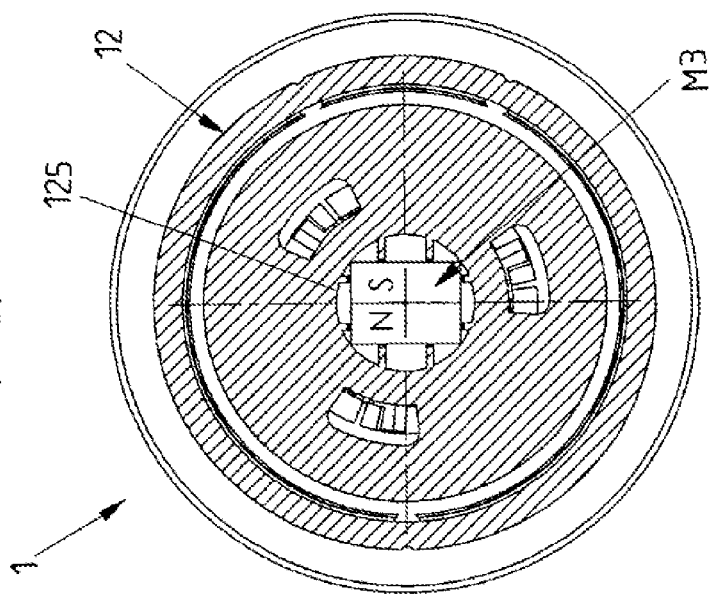
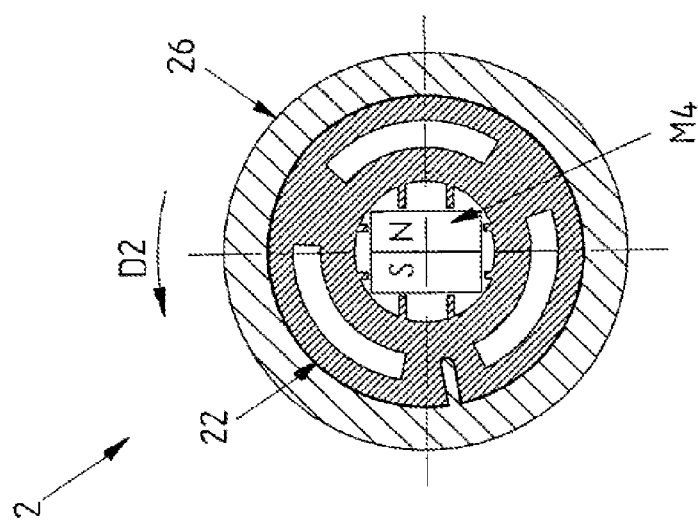
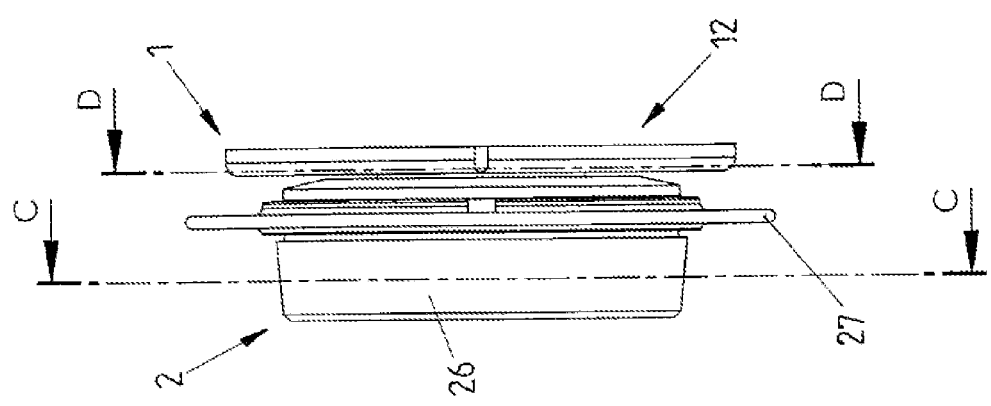

(B - B)

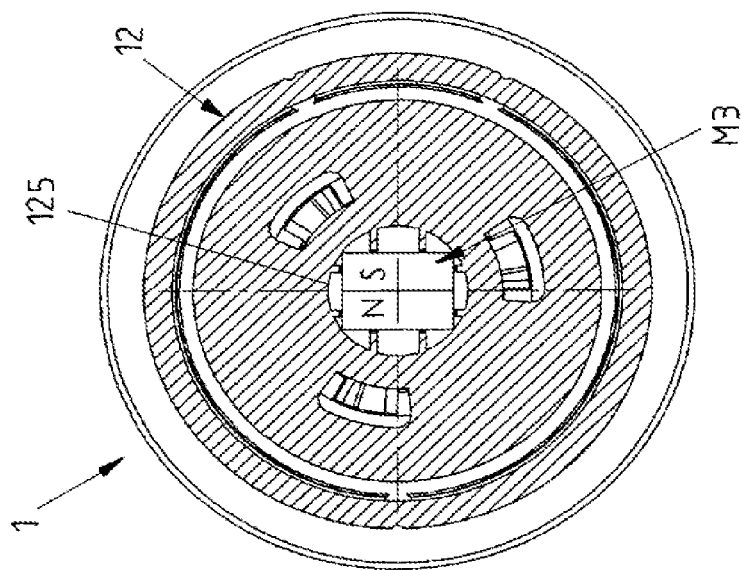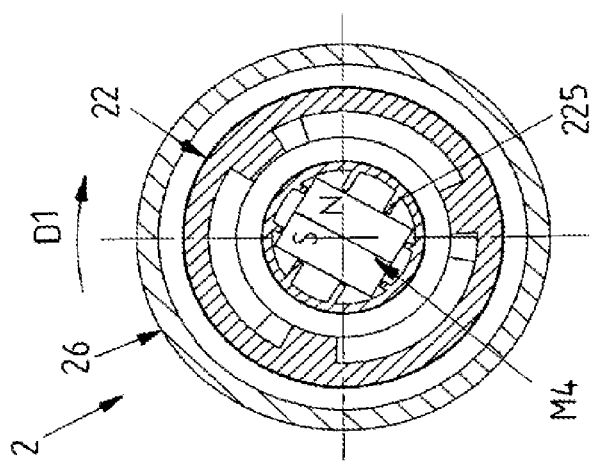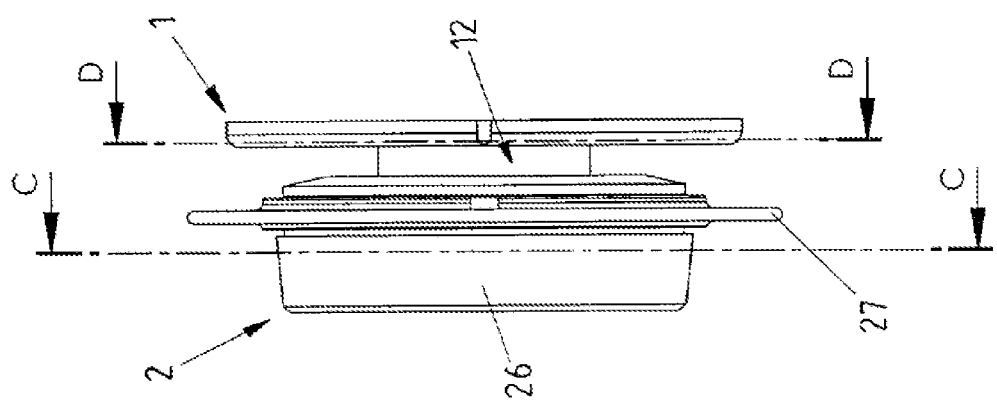

(B-B)

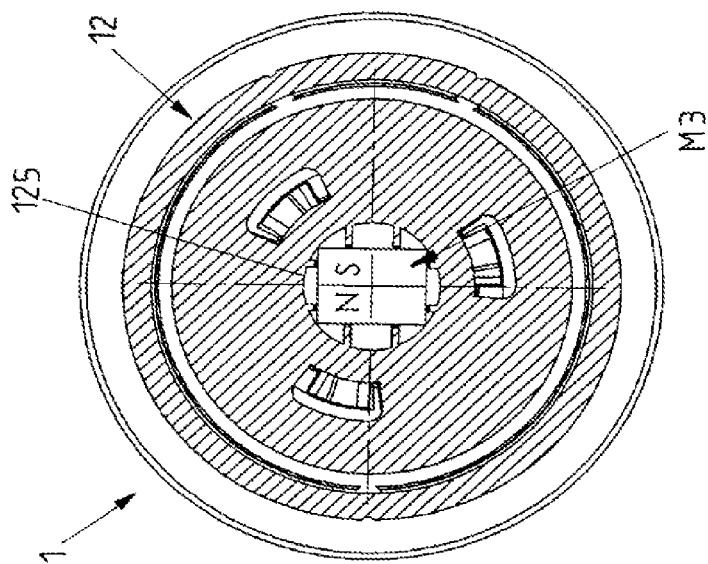
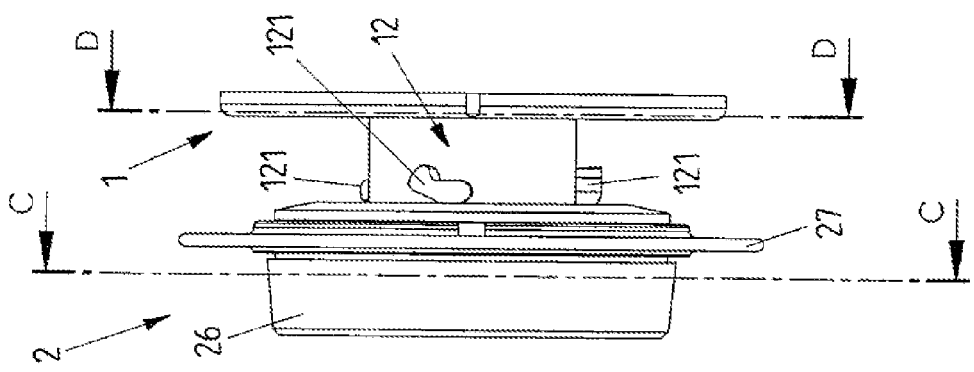

(B-B)

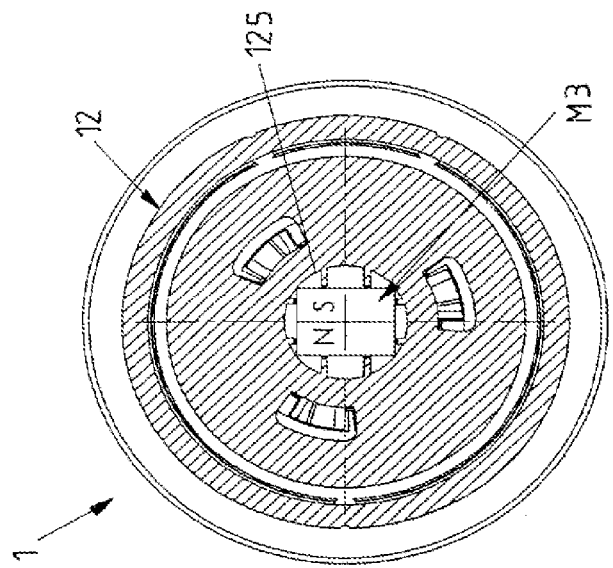
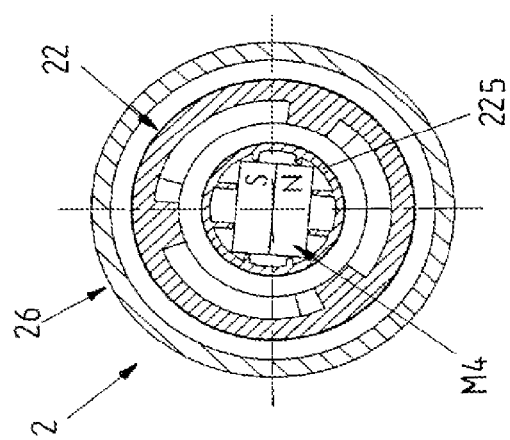
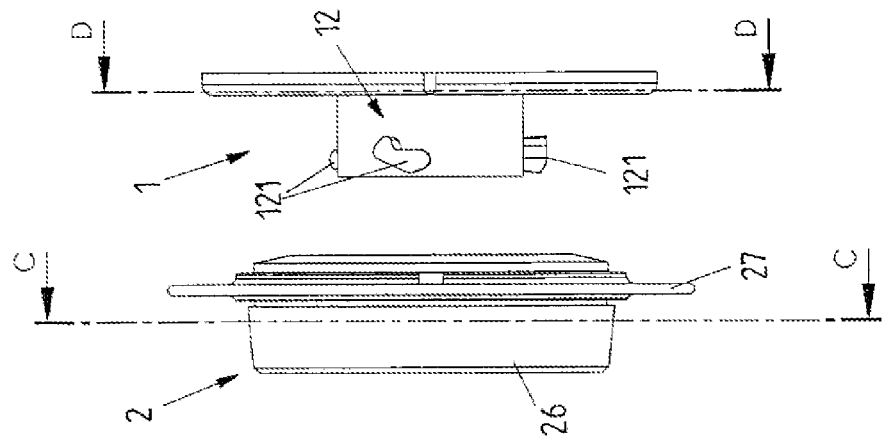

CLOSURE DEVICE WITH AN ADJUSTING DEVICE FOR AUTOMATICALLY ROTATING A CONNECTION ELEMENT OF A CLOSURE PART INTO A CLOSED POSITION

CROSS-REFERENCE TO RELATED APPLICATIONS

This application is the United States national phase of International Application No. PCT/EP2016/081060 filed Dec. 14, 2016, and claims priority to German Patent Application No. 10 2015 225 438.0 filed Dec. 16, 2015, the disclosures of which are hereby incorporated in their entirety by reference.

BACKGROUND OF THE INVENTION

Field of the Invention

The invention relates to a closure device

Description of Related Art

A generic closure device comprises, in this case, at least one first and one second closure part which are connectable together in order to close the closure device and which are releasable from one another in order to open the closure device. In this connection, the second closure part is movable in a closing direction along a connection axis toward the first closure part for closing the closure device. The first and the second closure parts additionally each comprise a connection element, the first and second closure parts being held together by means of the connection elements when the closure device is closed.

A generic closure device additionally comprises at least two magnetic elements which, when the closure parts are moved toward one another, cause magnetic attraction between the first closure part and the second closure part. The at least two magnetic elements support the moving closer together of the closure parts and consequently ensure that the closing of the closure device is easy and preferably automatic once the two closure parts have been moved toward one another.

WO 2015/004278 A1 discloses, for example, a closure device with two closure parts which are transferred automatically under the effect of at least two magnetic elements of the closure device into a relative position in relation to one another in which the closure device is closed in the intended manner. In this connection, the two closure parts are connected together in the manner of a screw connection such that, for example, a second closure part is screwed into the first closure part along a direction of rotation. Once the second closure part is fully screwed in, the two closure parts are held together in the axial direction via blocking surfaces. In this case, a closure device proposed in WO 2015/004278 A1 provides that, in a closed state, the two closure parts are axially displaceable relative to one another by a defined clearance in order to be able to screw the two closure parts together easily, i.e., almost without using any additional force, by the two closure parts being pressed toward one another in a first loading direction. The blocking surfaces, with the closure device in the closed position, then ensure, however, that the closure device is blocked from rotating open when a force in an opposite loading direction cooperates with the closure parts. If the closure parts are consequently simply pulled apart, for example with the closure device in the closed state, the screw connection cannot come undone.

The closure device disclosed in WO 2015/004278 A1 and designed in the manner of a screw closure is suitable for a plurality of application cases. In certain application cases, however, a closure device is preferred where a mechanical connection which is as clearance-free as possible is required.

SUMMARY OF THE INVENTION

An object underlying the invention, consequently, is to improve a closure device with two closure parts, the moving toward one another of which is supported by at least two magnetic elements, and in particular to provide an alternative to a closure device which is designed in the manner of a screw closure.

Said object is achieved with the closure device as described herein.

In the case of a closure device according to the invention, a first connection element of the first closure part comprises at least one guide portion and the second connection element of the second closure part comprises at least one closure portion, which enable the first and second closure parts to be held and locked together in the manner of a bayonet closure. It is provided in this connection that the guide portion comprises a guide surface which is angled toward the connection axis, is contacted by the closure portion when the second closure part is moved to the first closure part and which forces the second connection element to rotate about the connection axis relative to the connection element along a first direction of rotation when the first and second closure parts are moved closer together—under the effect of the at least two magnetic elements of the closure device, the guide portion comprises an end in the first direction of rotation such that the closure portion is guidable past the guide portion in the closing direction before the second connection element reaches an intermediate position relative to the first connection element, the closure device comprises an adjusting device, for example based on spring force and/or based on magnetic force, by means of which the second connection element in the intermediate position is acted upon with a force in a second direction of rotation opposite the first direction of rotation such that the second connection element is automatically rotated out of the intermediate position relative to the first connection element and about the connection axis along the second direction of rotation into a closed position, and in the closed position, (a) on the one hand the closure portion engages behind the guide portion at least in part in order to hold the first and second connection elements and consequently the first and second closure parts together, and (b) on the other hand for releasing the first and second closure parts, the second connection element is rotatable in the first direction of rotation in opposition to the force applied by the adjusting device—about the connection axis relative to the first connection element in order to open the closure device.

By means of the at least one guide portion of the first closure part, rotation of the second connection element of the second closure part is consequently first of all forced in a first direction of rotation before a rotation in the opposite second direction of rotation is automatically effected by means of the adjusting device as soon as the second connection element is no longer impeded from such rotation by the guide portion. As a result of the structurally forced change in the direction of rotation when closing the closure device, defined, secure engagement of the two connection elements in one another when the closure device is closed is ensured. Furthermore, the second connection element only has to be rotated just by a few degrees in the first direction of rotation in a first phase of the closing operation. Screwing in or out is not necessary. The second connection element is additionally transferred automatically into the closed position by means of the adjusting device for at least partially engaging behind the guide portion such that the closure device is able to be closed quickly and without any effort.

Underlying the same inventive concept, a closure device is additionally proposed where the first connection element comprises at least one guide portion and one holding portion and the second connection element comprises at least one first and one second closure portion, that is to say at least two closure portions, wherein the guide portion comprises a guide surface which is angled toward the connection axis, is contacted by the first closure portion when the second closure part is moved to the first closure part and which forces the second connection element to rotate about the connection axis relative to the connection element along a first direction of rotation when the first and second closure parts are moved closer together, the guide portion and the holding portion each comprise an end in the first direction of rotation such that the first closure portion is guidable past the guide portion in the closing direction and the other second closure portion is guidable past the holding portion before the second connection element reaches an intermediate position relative to the first connection element, the closure device comprises an adjusting device by means of which the second connection element in the intermediate position is acted upon with a force in the second direction of rotation opposite the first direction of rotation such that the second connection element is automatically rotated out of the intermediate position relative to the first connection element and about the connection axis along the second direction of rotation into a closed position, and in the closed position the second closure portion engages behind the holding portion at least in part in order to hold the first and second connection elements and consequently the first and second closure parts together, and for releasing the first and second closure parts from one another, the second connection element is rotatable in the first direction of rotation about the connection axis relative to the first connection element in order to open the closure device.

In the case of said closure device according to the invention, the portion which provides the guide surface and the portion which is engaged from behind by a connecting portion fall apart in order to hold the two closure parts together. If, for example, in a realization variant according to the first aspect of the invention, guide portions, which are simply spaced apart equidistantly from one another, are provided on a first connection element along a circumference for generating the rotation, guide portions and holding portions can alternate along a circumference of the first connection element according to the second aspect of the invention, the holding portions not comprising any guide surfaces for generating a rotational movement by the second connection element, however in the closed position the holding portions are engaged from behind in each case by a closure portion of the second connection element. For example, in a realization variant according to the first aspect of the invention, four identically realized guide surfaces are provided every 90° on a first connection element along a lateral surface which is circular in cross section, i.e., at 90° (3 o'clock), 180° (6 o'clock), 270° (9 o'clock) and 360° (12 o'clock). In a realization variant according to the second aspect of the invention, two guide portions and two holding portions are provided every 90° in an alternating manner on a first connection element along a lateral surface which is circular in cross section, i.e., at each of 90° (3 o'clock) and 270° (9 o'clock) a guide portion and at each of 180° (6 o'clock) and 360° (12 o'clock) a holding portion.

The adjusting device is, for example, based on spring force and/or based on magnetic force in order to act upon the second connection element in the intermediate position with a spring force and/or a magnetic force in the second direction of rotation.

In a realization variant, an adjusting device based on magnetic force includes the at least two magnetic elements which also cause magnetic attraction between the first closure part and the second closure part when the closure parts are moved together. In order then also to generate a magnetic force by means of said magnetic elements for rotating the second connection element into its closed position, at least one magnetic element is provided, for example, which comprises two different, i.e. unlike magnetic poles (north pole, south pole) in a plane which extends in a substantially perpendicular manner to the closing direction. For this purpose, said magnetic element is magnetized in an exemplary embodiment transversely to the closing direction such that a separation line between a north pole and a south pole of said magnetic element extends transversely to the closing direction. In the case of a magnetic element which is circular in cross section, for example, that is to say in the case of a disk-shaped magnetic element, said magnetic element is then magnetized diametrically, that is to say along its diameter. The separation line between north pole and south pole of said magnetic element extends here, when it is installed as intended in the closure device, transversely to the closing direction.

Instead of one single magnetic element with two different magnetic poles which are arranged in a plane which extends in a substantially perpendicular manner to the closing direction, two magnetic elements can also be provided on a closure part in such a manner that in this way two different magnetic poles are present in a plane which extends in a substantially perpendicular manner to the closing direction.

As a result of arranging two different magnetic poles in a plane which extends in a perpendicular manner to the closing direction, depending on the rotational position in which the closure parts are situated relative to one another about the connection axis, it is not only possible, when the closure parts are moved along the closing direction, to control whether the magnetic elements, which are provided in different closure parts, attract or repel. Rather, the generation of a torque is also possible in this way.

Against said background, a realization variant, for example, provides that for opening the closure device, rotation of the second connection element relative to the first connection element out of the closed position in the first direction of rotation beyond the intermediate position is permitted and each closure part comprises at least one magnetic element with two different magnetic poles or two magnetic poles in such a manner that there are two different magnetic poles in a plane which extends substantially perpendicularly to the closing direction. The magnetic elements of the first and second closure parts are then arranged, in this connection, on the closure parts in such a manner that the magnetic elements (a) magnetically attract when the closure device is closed and are arranged in such a manner with respect to one another in the intermediate position of the second connection element that the two connection elements, on account of the acting magnetic forces, strive to assume a relative position with respect to one another which corresponds to the closed position, and (b) magnetically repel when the closure device is opened when the second connection element is rotated out of the closed position relative to the first connection element in the first direction of rotation or in the second direction of rotation beyond the intermediate position.

In said variant, a magnetic element which is magnetized transversely to the closing direction can consequently be provided, for example, on each of the closure parts, the two magnetic elements of the two closure parts which are magnetized transversely to the closing direction then being part of the adjusting device and consequently not only supporting moving the two closure parts closer when closing the closure device but also rotating the second connection element in the second direction of rotation in order to assume the closed position. When opening the closure device, in turn, the at least two magnetic elements of the two closure parts are aligned to one another as a result of rotating the second connection element beyond the intermediate position such that they repel one another and consequently support the release of the two closure parts from one another.

In a realization variant, the guide portion of the first connection element comprises two different guide surfaces in such a manner that when closing the closure device, the second connection element is guided on the one guide surface, which is angled to the connection axis, by means of the closure portion abutting thereon for the rotation of the second connection element in the first direction of rotation and when opening the closure device, the second connection element is guided on the other guide surface for the rotation in the first direction of rotation.

Consequently, two guide surfaces, which, depending on whether the closure device is opened or closed, provide physical guiding for the second connection element, are provided on a single guide portion of the first connection element and are, for example, realized thereon.

Both guide surfaces, in this connection, are preferably realized at an angle to the closing direction in order to provide a certain guide path in this way on the one hand for moving the two closure parts closer together when closing the closure device and on the other hand for the defined release of the closure parts from one another when opening the closure device. The angles of the guide surfaces with reference to the closing direction and to the connection axis can be variable in this connection with respect to one another. For example, the (first) guide surface of the guide portion, by way of which guiding is provided in the first direction of rotation when the second closure part is moved toward the first closure part, is at a steeper angle than the other (second) guide surface of the guide portion by means of which guiding is provided when opening the closure device. The angles of the guide surfaces can, however, also be substantially identical.

In one exemplary embodiment, the different guide surfaces on a guide portion additionally extend at an angle of more than 90°.

In the case of multiple guide portions, which are spaced apart (equidistantly) from one another on the first connection element along a circumferential line about the connection axis or the closing direction, the individual guide portions are preferably realized identically to one another and consequently comprise, where applicable, in each case two different guide surfaces, which extend at an angle to one another, for the second connection element.

If multiple closure portions, which are spaced apart from one another (equidistantly) along a circumferential line about the closing direction or the connection axis, are provided on the second connection element, it can be provided in a realization variant that when closing the closure device, first of all the closure portion, which engages behind said guide portion at least in part in the closed position of the second connection element, on the first guide surface of a guide portion is guided for rotation in the first direction of rotation. Whereas when opening the closure device, a different adjacent closure portion abuts against the second guide surface of said guide portion. In this way, it is always possible to provide the second connection element with a defined rotational movement with a superimposed adjusting movement in the closing or opening direction by means of different closure portions by the different closure portions certainly abutting against the same guide portion and for rotation of the second connection element in the same (first) direction of rotation relative to the first connection element, however depending on whether the closure device is closed or open, abutting against different guide surfaces of said guide portion.

A closure portion of the second connection element comprises a sliding surface realized thereon, by means of which the closure portion moves into contact with a guide surface of the first connection element. In order to support, in this connection, automatic rotation of one of the connection elements relative to the other connection element as a result of the magnetic elements and also to enable smooth opening of the closure device for a user, a sliding surface is realized in one variant at an angle of more than 55° to the connection axis, for example at more than 60° and in particular by approximately 70°.

In a realization variant, the first closure part includes at least one first anti-rotation portion and the second closure part includes at least one second anti-rotation portion, wherein the second connection element is rotatable on the second closure part relative to the second anti-rotation portion and the at least one first anti-rotation portion and the at least one second anti-rotation portion are non-rotatably connectable together when closing the closure device. As a result of the non-rotatable connection, the anti-rotation portions and all parts rigidly connected thereto obtain a constant relative position with respect to one another during the connection of the connection elements (in particular with reference to rotation around the closing direction). This is advantageous, in particular, when two elements are to be secured together by means of the closure device, a first element being connected to the first closure part and a second element being connected to the second closure part. On account of the anti-rotation portions and of the rotatability of the second connection element relative to the second anti-rotation portion on the second closure part, the two elements to be secured together can remain in a desired or predetermined alignment relative to one another when the closure device is closed or opened. Thus, in this way, for example, the securing of an electronic device to a carrier element (for example to a bicycle) can be facilitated in a desired or predetermined alignment relative to the carrier element. The electronic device connected to the second closure part can remain, for example, during the closing of the closure device constantly in a position (with reference to the rotation around the closing direction) which it assumes when moving the closure parts toward one another.

Thus, for example, the first closure part can comprise a first securing element which is connected to the first connection element for securing the first closure part to a carrier element, the first securing element being connected to the at least one first anti-rotation portion non-rotatably with reference to a rotation in the closing direction. For example, in this case, the first securing element can be realized for securement of the first closure part to a tubular carrier element, in particular to bicycle handlebars. It is obviously also conceivable for the first securing element to be realized for securing the first closure part to a different carrier element, such as, for example, to motorbike handlebars. In principle, a closure device according to the invention can be realized and set up, in particular, for any type of holder for securing an object to a two-wheeler or three-wheeler. This includes, along with the use as part of a device holder on handlebars, among other things, the use for a bag holder on a bicycle, motorbike or trike.

In a possible realization variant, the second closure part comprises a second securing element for securing an object, for example an electronic device or a bag, to the second closure part. The second securing element, in this connection, can be non-rotatably connected to an anti-rotation element of the second closure part which comprises the at least one second anti-rotation portion. In principle, the second anti-rotation portion of the second closure part can be provided on a separate anti-rotation element, relative to which the second connection element is non-rotatably mounted. The second closure part, designed with multiple parts, consequently comprises, along with the connection element, at least one more component which is connected thereto. The anti-rotation element can be connected, in turn, non-rotatably to a securing element of the second closure part, by means of which the second closure part is connected to an element, such as, for example, an object which is to be secured to a carrier element.

For example, a connection between the anti-rotation element and a securing element is provided by means of a bayonet connection. In one variant, the anti-rotation element realizes, for example, closure hooks, which engage in assigned ballet openings in the securing element when said anti-rotation element is moved toward the securing element, and latch with said closure hooks by rotating the anti-rotation element relative to the securing element. For said latching, which is provided during the assembling of the closure part, the securing element realizes, for example at each of its bayonet openings, latching lugs which, once the securing element has been rotated relative to the anti-rotation element, each engage behind a closure hook which reaches through the associated bayonet opening, and are secured in a positive locking manner in the bayonet opening.

According to one embodiment, the at least one first anti-rotation portion and/or the at least one second anti-rotation portion comprises a hollow cylindrical basic form which extends axially along the closing direction. As a result of both anti-rotation portions having a hollow cylindrical basic form, they can comprise a high degree of mechanical stability and at the same time are able to be produced in a comparatively cost-efficient manner. The anti-rotation portions, in this connection, can be realized in such a manner that when the closure parts are moved toward one another, the at least one first anti-rotation portion surrounds the at least one second anti-rotation portion or the at least one second anti-rotation portion surrounds the at least one first anti-rotation portion at least in portions all around the closing direction. As a result of such an arrangement, it is possible to produce a positive locking closure of the anti-rotation portions together and, in this way, the closure parts radially overall with reference to the closing direction. A guide portion is realized, for example, on an outer lateral surface of the first connection element. A closure portion, in turn, is realized, for example, on an inner lateral surface of the second connection element which, with the closure device in the closed state, surrounds the outer lateral surface of the first connection element in a circumferential manner.

The at least one first anti-rotation portion and the at least one second anti-rotation portion engage one another in a positive locking manner in one realization variant when closing the closure device to produce a non-rotatable connection. In this connection, an anti-rotational portion of a closure part can comprise at least one elongated positive locking element along the closing direction, whilst an anti-rotation portion of the other closure part comprises at least one recess which is elongated along the closing direction for receiving the at least one elongated positive locking element. A non-rotatable connection between the anti-rotation portions is produced by means of the engagement of the positive locking element in a recess or the engagement of multiple positive locking elements in multiple recesses and a resultant locking of the respective positive locking element transversely to the closing direction (and to a connection axis of the closure device which coincides thereto).

A positive locking element and/or a recess can be formed at least in portions conically to the closing direction. In one exemplary embodiment, multiple positive locking elements and the associated recesses are each realized conically and tapering in the closing direction. The positive locking elements are consequently realized in a wedge-shaped manner and, once the closure device has been closed as intended, are preferably also held in a non-positive locking manner in the respective recess. In this way, once the closure device has been closed, an additional non-positive and positive locking component connection is provided for the interconnected, first and second closure parts by means of the positive locking elements and the recesses which receive them.

In one exemplary embodiment, multiple positive locking elements and/or multiple recesses are spaced apart from one another on the respectively associated anti-rotation portion along a circumferential line about the closing direction. For a uniform distribution of loads occurring and a positive locking, non-rotatable connection between the two anti-rotation portions in multiple relative positions about the closing direction, the positive locking elements and recesses are, in this connection, spaced apart from one another, for example equidistantly; for example, in the case of four positive locking elements, they are each offset to one another by 90°.

In one realization variant, an anti-rotation element of the second closure part, which comprises at least one second anti-rotation portion, is utilized additionally as support for a spring element of a spring force-based adjusting device. The spring element, which provided on the second closure part, is supported then, in this connection, at the one end on the anti-rotation element and at the other end on the second connection element in order to act upon the second connection element in the intermediate position with a spring force in the second direction of rotation. By means of the at least one spring element, a resetting force is consequently exerted on the second connection element in the second direction of rotation about the closing direction and about the axis once, when closing the closure device, the second connection element has been rotated on account of the at least one guide portion initially in the first direction of rotation relative to the first connection element and to the second anti-rotation element connected non-rotatably thereto by means of the anti-rotation portions and consequently the at least one spring element has been tensioned (more tightly). As soon as the second connection element reaches its intermediate position once a first phase of the closing operation has been completed, and rotation of the second connection element relative to the first connection element is no longer blocked by means of the guide portion or the guide portions of the first connection element, the second connection element, under the effect of the spring element, is rotated into its closed position in which the guide portion (in each case) is engaged from behind by the (assigned) closure portion at least in part—with reference to the connection axis.

In other words, the second connection element is consequently prestressed by means of the at least one spring element on the second closure part relative to the anti-rotation element. When moved toward the first closure part, the closure parts are pulled together under the effect of the at least two magnetic elements. As a result of the guide surface of the guide portion extending at an angle, the at least one closure portion of the second closure part is guided along the angled guide surface of the guide portion due to the attracting effect of the magnetic elements and, as a result, the second connection element is rotated in the first direction of rotation relative to the second anti-rotation portion of the second closure part, which is already connected non-rotatably to the first connection element of the first closure part. Said rotation in the first direction of rotation is effected in opposition to the resetting force of the spring element. The spring element is then stressed (more strongly) in the intermediate position and thereby presses or pulls the second connection element into the second direction of rotation and consequently into the closed position.

In one realization variant which builds on a closure device with anti-rotation portions, the second closure part (additionally) comprises an actuating element which is rotatable on the second closure part both relative to the second anti-rotation portion and relative to the second connection element. With the closure device closed as intended said actuating element is rotatable in the first direction of rotation about the connection axis in order to act upon the second connection element and to rotate the second connection element relative to the first connection element. The actuating element is consequently actuatable by a user and transmits an adjusting force for unlocking the closure device to the second connection element which is usually not directly accessible to a user in such a realization variant when the closure device is closed. The actuating element, in this connection, can interact, for example, with the second connection element in such a manner that the actuating element entrains the second connection element in the manner of an entrainment means for opening the closure device.

In a further development which is based thereon, the actuating element, with the closure device closed, is held in a relative position to the second connection element, from which the actuating element has to bridge a predefined void rotational path in the first direction of rotation before the actuating element acts on the second connection element and the closure device is able to be opened as intended. By the actuating element initially having to cover a predetermined void rotational path before it acts on the second connection element and consequently adjusting the one closure portion thereof or the multiple closure portions thereof such that, in this way, one guide portion or multiple guide portions of the first connection element are no longer engaged behind and it is possible to separate the closure parts from one another along the connection axis, the risk of unintentional opening of the closure device is reduced. A user must thus first of all rotate the actuating element about the predetermined void rotational path in the first direction of rotation until it is at all possible in this way to act upon the second connection element for releasing the connection between the two closure parts. In addition, a type of "polarity reversal" of the acting magnetic forces is possible in this way prior to opening the closure device. Thus, when using multiple magnetic elements, which are each arranged on a closure part in such a manner that in this way different (unlike) magnetic poles are present in a plane which extends transversely to the closing direction, the bridging of the void rotational path can include that the magnetic elements of a closure part are entrained and, as a result, are rotated into a relative position to the magnetic elements of the other closure part, in which the magnetic elements of both closure parts repel one another and consequently support the opening movement.

In a further development, the actuating element, with the closure device closed, is held by means of the at least two magnetic elements in the relative position to the second connection element, from which the actuating element has to bridge the predefined void rotational path in the first direction of rotation before the actuating element acts on the second connection element and entrains it. For example, it is possible to ensure by means of the action of the correspondingly arranged magnetic elements of the first and second closure parts that the actuating element, with the closure device closed as intended, is present in the desired relative position and consequently a void rotational path has to be bridged.

The actuating element and the second connection element can be realized and arranged in such a manner that the second connection element, when rotating into the intermediate position along the first direction of rotation, acts on the actuating element and rotates the actuating element in the first direction of rotation about the connection axis. The second connection element consequently entrains the actuating element in a first phase of the closing operation and rotates it in the first direction of rotation. In a further development, in the case of the connecting rotation of the second connection element in the opposite second direction of rotation, force transmission from the second connection element to the actuating element is not provided. For example, portions which simply project radially in an alternatingly local manner are provided in such a manner on the actuating element and on the second connection element that, as a result, when the closure device is closed, entrainment of the actuating element when the second connection element is rotated in the first direction of rotation is ensured, but in the case of the connecting rotation of the second connection element in the opposite second direction of rotation, it does not act on the actuating element.

A realization variant provides, where applicable in combination with the aforenamed features, that the closure device comprises an actuating element which is rotated automatically in the second direction of rotation. It is provided, for example, that the actuating element, with the second connection element in the intermediate or closed position, experiences torque in the second direction of rotation by means of at least two magnetic elements of the closure device. Thus, the actuating element, just as the first connection element of the first closure part, can comprise a magnetic element which is magnetized transversely to the closing direction in such a manner that, as a result, it is not only the two closure parts that are attracted when the closure device is closed but also the actuating element is aligned automatically into a certain relative position with reference to the first connection element when the second connection element is situated in the intermediate position or the closed position. The actuating element is rotated in the second direction of rotation in this manner in a second phase of the closing operation (adjustment of the second connection element out of the intermediate position into the closed position) on account of the acting magnetic forces. In such a variant, the second connection element can be pulled or pressed along the second direction of rotation about the connection axis into its closed position under the effect of at least one spring element such that in the intermediate position the second connection element is prestressed mechanically in the second direction of rotation by at least one spring element, but the actuating element is prestressed magnetically by at least two magnetic elements.

In one realization variant, the closure device comprises a travel limitation with at least one stop on the second connection element and at least one counter stop in such a manner that rotation of the second connection element when the opening and/or closing the closure device is limited to a predetermined maximum rotational angle as a result of contact between stop and counter stop. The provision of a travel limitation, in this connection, is viewed as advantageous in particular, on the one hand, when using individual magnetic elements which are magnetized transversely to the closing direction, as well as, on the other hand, when using multiple magnetic elements which are each arranged on a closure part in such a manner that, as a result, different (unlike) magnetic poles are present in a plane which extends transversely to the closing direction. It is possible to ensure by means of the travel limitation that the magnetic elements of the first and second closure parts provide the desired amount of magnetic repulsion and the desired amount of reverse torque in the respective alignment of the closure parts or of their connection elements with respect to one another when closing and opening the closure device. In this case, however, by means of the arrangement and alignment of the magnetic elements, magnetic repulsion and a reverse torque are excluded from being maximum at the same time.

In an exemplary embodiment, the second closure part comprises a securing element which is defined by a stop ring and is secured on an element which is provided with the second closure part, for example a closure lug. The second connection element is then mounted so as to be rotatable relative to said securing element and by means of a counter stops realized thereon is limited in its rotatability relative to the securing element both in the first direction of rotation and in the second direction of rotation. The counter stops of the securing element, in this connection, restrict the rotatability of the second connection element for example to a range of rotation below 270°, preferably below 180°, in particular below 150° and, for example, to a range of approximately 120°.

The restriction of the rotatability, in this case, is also sensible insofar as, in the case of an exemplary embodiment with a magnetic force-based adjusting device, the connection elements can be acted upon with a reverse torque by means of the adjusting device and the correspondingly arranged magnetic elements thereof in principle in both possible directions of rotation and rotatability in both directions is consequently not restricted by the adjusting device per se. Thus, for example in the case of diametrically magnetized magnetic elements which are assigned on the one hand to the first and on the other hand to the second connection elements, a reverse torque is generatable in the one or the other direction of rotation depending on the relative position of the magnetic element and consequently depending on the relative position of the connection elements. This allows for clearly greater flexibility in the design and method of operation of the closure device and also for a clearly smaller installation space requirement compared to a spring force-based adjusting device. The closure device can consequently be realized in a very compact manner and a choice of direction of rotation for closing and opening can be user-dependent.

In an exemplary embodiment, in the closed position, the guide portion of the first connection element and the closure portion of the second connection element are displaceable axially relative to one another by a defined clearance with reference to the connection axis of the first and second closure parts. The guide portion and the closure portion, in this connection, however, are then blocked at the same time—after bridging a clearance—against rotation relative to one another about the connection axis and against removal in opposition to the closing direction when, with the second connection element in the closed position, a force, which acts along the connection axis and loads the respective closure part in a direction pointing away from the other closure part, cooperates with the first and/or second closure part. Blocking parts of the first and second connection elements, which interact after bridging the clearance, are provided for blocking. As a result of the clearance provided, the closure portion is (or multiple closure portions are) consequently spaced in the axial direction—with reference to the connection axis—apart from the (respective) at least partially engaged-behind guide portion. In order then to prevent the closure device from being opened in an unwanted manner, for example as a result of pulling on the second closure part, without the second connection element having been rotated beforehand, the interacting blocking parts are provided on the two connection elements. If, for example, the second closure part is pulled relative to the first closure part in an opening direction that is opposite to the closing direction, the blocking parts of the first and second connection elements hook or latch with one another and prevent the two connection elements rotating relative to one another. It is consequently not possible to open the closure device with a correspondingly applied load. This is only possible with the closure device in a (largely) non-loaded state when the guide portion and the closure portion or the guide portions and the closure portions are spaced apart from one another in the axial direction and consequently the second connection element is able to be rotated in the first direction of rotation relative to the first connection element.

In a further development, a first blocking part is provided on the guide portion and a second blocking part is provided on the closure portion. For example, a first blocking part is realized by a hook-shaped region on the guide portion and a second blocking part is realized by a complementarily designed hook-shaped region on the closure portion.

As already mentioned beforehand, multiple guide portions which are spaced apart from one another can be provided on the first connection element, in particular can be realized thereon, just as multiple closure portions which are spaced apart from one another are provided on the second connection element, in particular can be realized thereon. On the one hand, the connection between the two closure parts in different relative positions with respect to one another with reference to the connection axis can be facilitated by means of multiple guide portions and closure portions. On the other hand, increased mechanical stability of the closed closure device is achieved in this way.

A holder for securing an object on a two-wheeler or three-wheeler, in particular in the form of a handlebar holder, can be provided with a closure device provided according to the invention.

A holder for an electronic device with a closure device according to the invention is additionally proposed. The electronic device can be, for example, a mobile phone, in particular a smart phone, a navigation device or a different communications device or mobile terminal. Via the holder, said electronic device is then securable to a carrier element by means of the closure device.

A holder for securing an object on a two-wheeler or three-wheeler, in particular in the form of a handlebar holder, with a closure device according to the invention is additionally proposed. The object to be secured can be, for example, an electronic device or a bag.

Furthermore, a closure device which is designed according to the invention is deemed to be advantageous in particular for a closure for clothes, shoes or prostheses on account of it being easy and rapid to close, the reliable locking together of the closure parts and the possibility of opening the closure device easily and rapidly. Thus, the first closure part can be assigned, for example, to a first part of an item of clothing, a shoe or a prosthesis and fixed thereon. The second closure part is then secured to a further part of the item of clothing, of the shoe or of the prosthesis, for example to a flap.

Multiple closure devices designed according to the invention can also obviously be provided in this connection on an item of clothing, a shoe or a prosthesis and multiple closures for clothes, shoes and prostheses can each be accordingly provided with a closure device provided according to the invention.

Against said background, the use of a closure device provided according to the invention as part of a closure for clothes, shoes or prostheses is also proposed.

BRIEF DESCRIPTION OF THE DRAWINGS

Further advantages and features of the invention will be made clear in the following description of exemplary embodiments by way of the figures, in which:

FIGS. 2A to 2C show various views of the closure device each in an exploded representation;

FIGS. 4A to 4G show sectioned representations in each case corresponding to the cutting line H-H in FIG. 3 of the closure device in various phases during closing and opening;

FIG. 4H shows a modification of the closure device according to the first realization variant, where a first closure element comprises guiding and holding portions;

FIGS. 6A to 6C show various views of the closure device of FIGS. 5A to 5C each in an exploded representation;

FIGS. 8A to 14D show consistent views in each case of the closure device of FIGS. 5A to 6C in various phases during closing and opening, four views having been chosen in each case to illustrate the various phases;

FIGS. 16A to 16C show various views of the closure device of FIGS. 15A to 15C each in an exploded representation;

FIG. 17 shows a top view of the closure device of FIGS. 15A to 16C with representation of a cutting line H-H;

FIGS. 18A to 25D show consistent views in each case of the closure device of FIGS. 15A to 16C in various phases during closing and opening, four views having been chosen in each case to illustrate the various phases;

FIGS. 27A to 27C show various views of a fourth realization variant of a closure device according to the invention in a closed state;

FIG. 27D shows a top view of the closure device of FIGS. 27A to 27C with representation of a cutting line A, A;

FIG. 27E shows a sectional representation of the closure device of FIG. 27D along the cutting line A-A;

FIGS. 28A to 28C show various views of the closure device of FIGS. 27A to 27E each in an exploded representation;

DESCRIPTION OF THE INVENTION

Figure 1C:
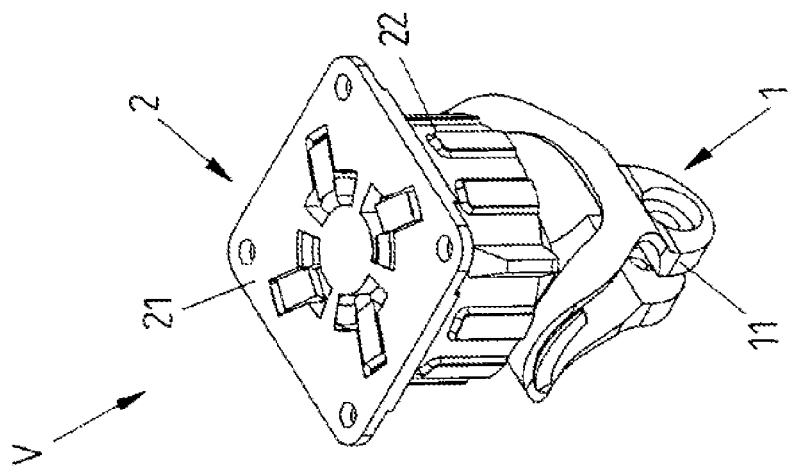
FIGS. 1A to 1C show various views of a first realization variant of a closure device according to the invention in a closed state.

FIGS. 1A to 4G show various views of a closure device V which includes a first closure part 1 and a second closure part 2. The closure parts 1 and 2 are connectable together and lockable together in order to close the closure device V, and are releasable from one another in order to open the closure device V. A securing element 11 or 21, by means of which the respective closure part 1 or 2 is securable to one of two elements which are to be releasably coupled together by means of the closure device V, is in each case part of the closure parts 1 and 2. In the present case, the first closure part 1 comprises a securing element 11 to secure the first closure part 1 to a carrier element, for example to bicycle or motorbike handlebars. The securing element 11 in the present case is realized as a clip for this reason. The second securing element 21 of the second closure part 2, in turn, is provided in the present case for securing an electronic device, for example a smart phone and for this reason is realized with a planar rectangular in this case top surface.

The first connection element 12, in this connection, is fixed to the first securing element 11 by means of two radially projecting fixing lugs 122a and 122b. The fixing lugs 122a and 122b extend diametrically opposed to each other and engage behind edge portions of the first securing element 11 which border a bearing opening 110 of the first securing element 11 in order to secure the first connection element 12 in a positive locking manner to the first securing element 11.

Figure 1B:
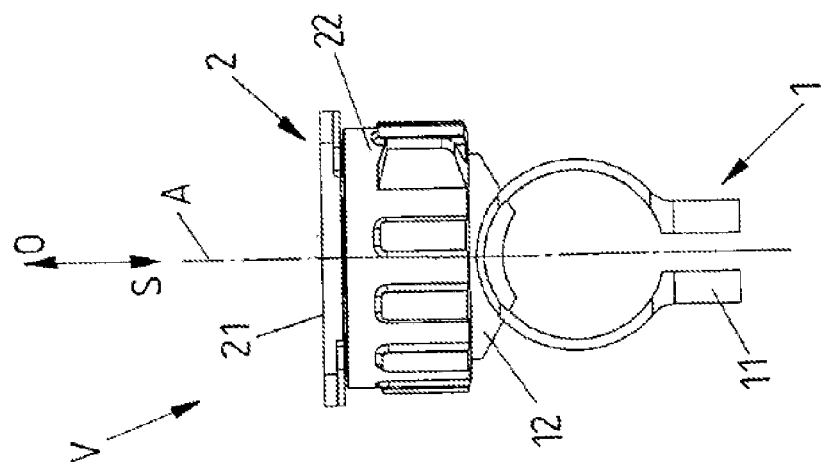
Figure 1A:
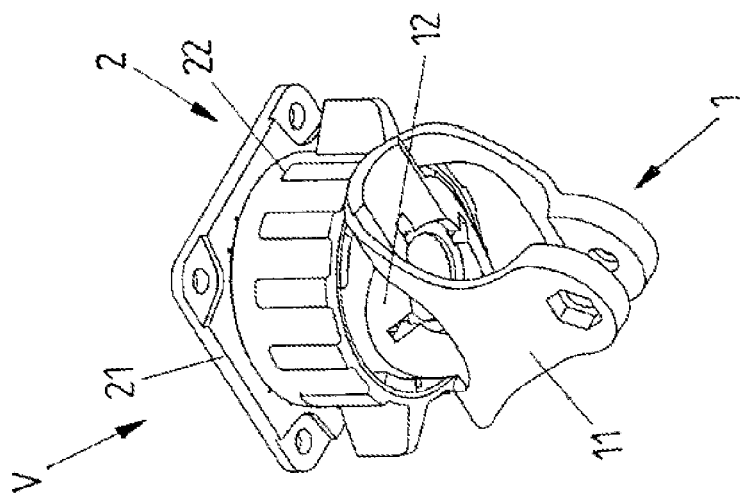
Figure 3:
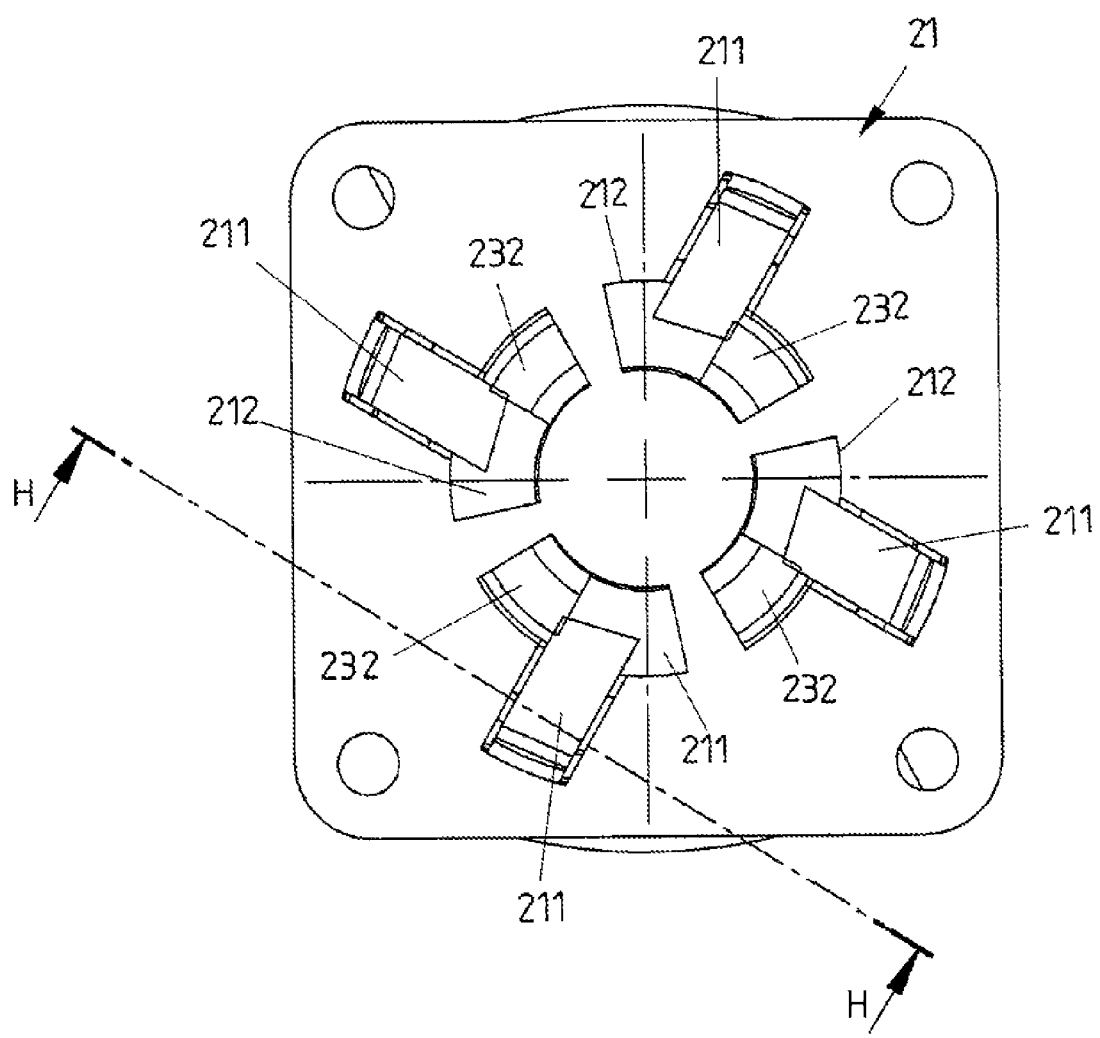
FIG. 3 shows a top view of the closure device with representation of a cutting line H-H.
Figure 5C:
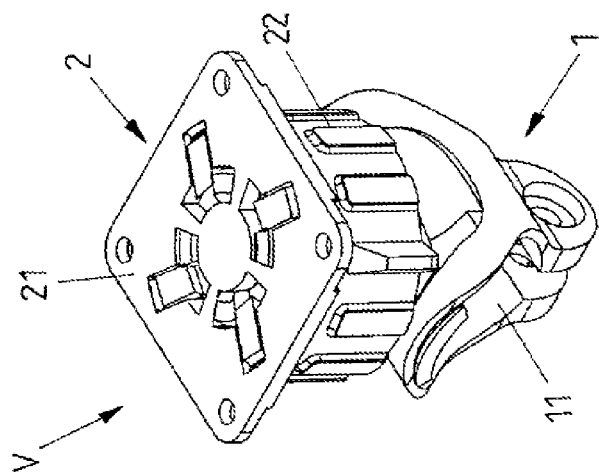
FIGS. 5A to 5C show various views of a second realization variant of a closure device according to the invention in a closed state.
Figure 5B:
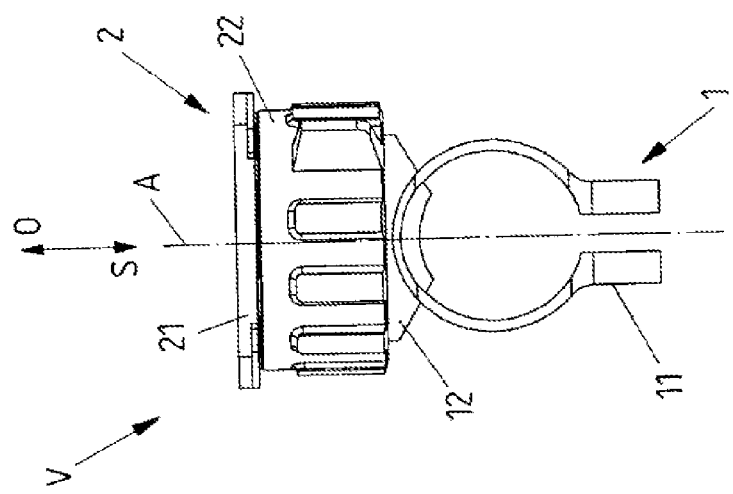
Figure 5A:
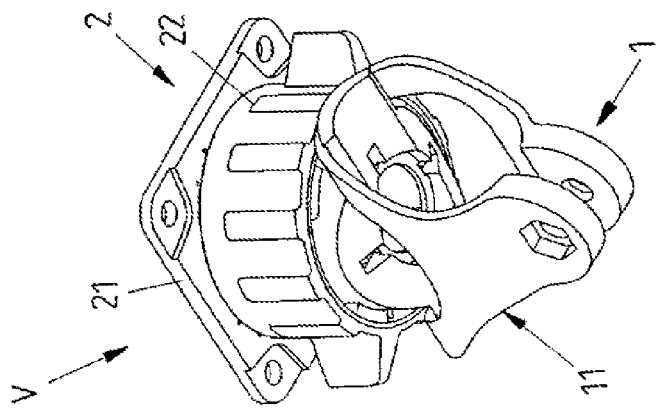

The two closure parts 1, 2 are held together in the closed state of the closure device V shown in FIGS. 1A, 1B and 1C in the manner of a bayonet connection and are releasable from one another along a connection axis A once locking between two connection elements 12 and 22 of the first and second closure parts 1, 2 has been released.

To close the closure device V, for example the second closure part 2 is moved along a connection axis A in a closing direction S toward the first closure part 1 and is locked to said first closure part. In this connection, the (second) connection element 22 of the second closure part 2 is rotated in consecutive phases of a closing operation in opposite directions of rotation D1 and D2 about the connection axis A relative to the (first) connection element of the first closure part 1, as is illustrated in detail by way of FIGS. 3 and 4A to 4G which are yet to be explained below.

First of all, the design of the closure parts 1 and 2 is to be explained in more detail by way of the exploded views of FIGS. 2A, 2B and 2C.

It can be seen from said exploded views in particular that each of the closure parts 1, 2 is constructed with multiple parts and, among other things, includes a magnetic element M1 or M2 in each case, the magnetic elements M1 and M2, when the closure parts 1 and 2 are moved toward one another, cause magnetic attraction between the closure parts 1 and 2. The first magnetic element M1 of the first closure part 1 is realized in a disk-shaped manner in the present case. The first magnetic element M1, in this case, is accommodated centrally in a bearing portion 125 of the first connection element 12.

The first connection element 12 realizes a hollow cylindrical connection body, at the lower end thereof the bearing portion 125 is provided and on the outer lateral surface thereof multiple guide portions 121, which are spaced apart from one another, are realized. The individual guide portions 121 of the first connection element 12, which are spaced apart from one another along a circumferential line about the connection axis A, are each triangular in cross section and project, with reference to the connection axis A, radially outward on the hollow cylindrical connecting body of the first connection element 12. The individual guide portions 121, in this connection, are designed in such a manner that they each realize a guide surface 1210 which is at an angle to the connection axis A in the closing direction S, by means of which guide surface the second connection element 22 of the second closure part 2, under the attraction of the magnetic elements M1 and M2 once the second closure part 2 has been moved toward the first closure part 1, is made to rotate about the connection axis A when it is moved closer to the first closure part 1.

On its inner lateral surface, the hollow cylindrical connecting body of the first connection element 12 realizes first anti-rotation portions in the form of multiple elongated recesses 123. Said recesses 123 extend along the connection axis A and taper along the closing direction S, in which the second closure part 2 is moved toward the first closure part 1 for closing the closure device V. The four recesses 123 in the present case are each offset to one another about the connection axis A by 90° and serve to receive second anti-rotation portions in the form of elongated, conical positive locking elements 231 of an anti-rotation element 23 of the second closure part 2. The anti-rotation element 23 of the second closure part 2 is moved into positive locking engagement with the recesses 123 of the first connection element 12 when the second closure part 2 is moved toward the first closure part 1. As a result of the engagement of the positive locking elements 231 in the recesses 123, which are realized complementarily to said recesses, the anti-rotation element 23 of the second closure part is connected non-rotatably to the first connection element 12 of the first closure part 1 during the closing operation. By the second securing element 21 of the second closure part 2 being connected, in turn, non-rotatably to the anti-rotation element 23, the securing element 21 and an object secured thereon can remain in a certain alignment to the first closure part 1 and does not have to be rotated relative to the connection axis A in order to connect the two closure parts 1 and 2 together as intended.

By means of the cone design of the web-like and radially projecting, elongated positive locking elements 231 of the anti-rotation element 23 and the cone design of the elongated recesses 123 corresponding thereto of the first connection element 12, the anti-rotation element 23 can engage in an almost tolerance-free manner in the first connection element 12, which, with the closure device V closed, surrounds the inserted part of the anti-rotation element 23 circumferentially all around the connection axis A.

To fix the anti-rotation element 23 to the securing element 21, multiple (in the present case four) closure hooks 232 are provided on the anti-rotation element 23 and bayonet openings 212, which are assigned to said closure hooks 232, with latching lugs 211 are provided on the securing element 21. The closure hooks 232 of the anti-rotation element 23 are inserted into the bayonet openings 212 of the second securing element 21 and are locked therein in a positive locking manner. The individual latching lugs 211 of the bayonet opening 212 are each mounted elastically and, once a closure hook 232 has been inserted into the respective bayonet opening 212, allow the associated closure hook 232 to be guided past a radially inner end of the respective latching lug 211 when the anti-rotation element 23 and the second securing element 21 are rotated relative to one another when the second closure part 2 is assembled. If, in this connection, the closure hooks 232 are pushed inside the respectively associated bayonet opening 212 into a region with smaller dimensions, the closure hooks 232 latch with the latching lugs 211 and are engaged from behind by said latching lugs. In this way, the anti-rotation element 23 is locked on the second securing element 21 by means of a bayonet connection and is non-rotatably connected thereto.

The closure hooks 232 protrude from the anti-rotation element 23 in the axial direction with reference to the connection axis A and are arranged above a securing collar 233 of the anti-rotation element 23. Once the anti-rotation element 23 has been fixed as intended on the second securing element 21, a circular ring-shaped gap remains between the securing collar 233 and an underside of the second securing element 21. Radially inwardly protruding bearing webs 222 of the equally hollow cylindrical second connection element 22 engage in said circular ring-shaped gap such that said bearing webs 222 are received in a positive locking manner between the securing collar 233 and the second securing element 21. In this way, the second connection element 22 is mounted on the second closure part 2 so as to be rotatable about the closing direction S and the connection axis A.

The anti-rotation element 23 additionally realizes a bearing portion 235 for receiving the second magnetic element M2. Furthermore, a spring bearing region 234, which is arranged between the positive locking elements 231 and the underside of the securing collar 233 in the axial direction, is provided on the anti-rotation element 23. A spring element 24, which is realized as a helical spring in the present case, is mounted in said spring bearing region 234. Said spring element 24 is supported at one end on the second connection element 22 of the second closure part 2 and at the other end on the anti-rotation element 23. For this purpose, in each case a spring end 240 of the spring element 24, for example, engages in a retaining opening provided for this purpose on the second connection element 22 or on the anti-rotation element 23. The rotatably mounted second connection element 22 is prestressed in such a manner via the spring element 24 in a direction of rotation with reference to the anti-rotation element 23 (and to the second securing element 21 non-rotatably connected hereto). In the present case, the spring element 24 consequently forms a loading device 24, by means of which the second connection element 22 is automatically transferred into a closed position when closing the closure device V.

For holding the two connection elements 12 and 22 and consequently also the closure parts 1 and 2 together, the hollow cylindrical second connection element 22 comprises on its inner lateral surface multiple (in the present case four) closure portions 221 which are spaced apart from one another equidistantly along a circumferential line about the connection axis A and, with the closure device V in the closed state, in each case engage behind one of the guide portions 121 at least in part. The closure portions 221, in this case, are each realized as radially projecting webs which are elongated along a circumferential line about the connection axis A. When the closure device V is closed, said closure portions 221 each move into contact initially with the angled guide surface 1210 of each guide portion 121 of the first connection element 12, by means of the angled guide surface 1210, the second connection element 22 being forced, when moving even closer toward the first connection element 12, to move rotationally about the connection axis A and relative to the first connection element 12 in a first closing direction D1. This is illustrated in more detail in particular by way of FIGS. 4A to 4C.

When the second closure part 2 is moved toward the first closure part 1, magnetic elements M1 and M2 cause magnetic attraction between the first closure part 1 and the second closure part 2. For this purpose, the magnetic elements M1 and M2 of the two closure parts 1 and 2, which are realized as permanent magnets, point toward one another with unlike magnetic poles when the second closure part 2 is moved as intended toward the first closure part 1 such that there is a magnetic attraction in the closing direction S between the magnetic elements M1 and M2. Under the effect of the magnetic elements M1 and M2, the two closure parts 1 and 2 are consequently moved closer to one another. As a result of the resultant magnetic force which acts in the closing direction S, each closure portion 221 of the rotatably mounted second connection element 22 is pressed against a guide surface 1210 of a guide portion 121 of the first connection element 12. A sliding surface 2210 of the respective closure portion 221 then slides here along the guide surface 1210 of the guide portion 121 which slopes away in the closing direction S such that, as a result, the second connection element 22 is forced to rotate about the connection axis A relative to the first connection element 12 along a first direction of rotation D1 when the two closure parts 1 and 2 are moved even closer toward one another under the effect of the magnetic elements M1 and M2.

As the anti-rotation portion 23 of the second closure part 2 is engaged, in this connection, with the first connection element 12 and is rigidly connected to said first connection element, the second connection element 22, in this connection, is also rotated relative to the anti-rotation element 23, as a result of which the spring element 24, which cooperates with the second connection element 22 and the anti-rotation element 23, is stressed (in a stronger manner) and a resetting force is exerted on the second connection element 22 in an opposite second direction of rotation D2.

When the two closure parts 1 and 2 are moved even closer toward one another, the second connection element 22 is then rotated in the first direction of rotation D1 until it reaches an end of the respective guide portion 121, which lies in said direction of rotation D1, and can consequently be guided past said guide portion 121 in each case in the axial direction, i.e. in the closing direction S. As a result of moving the second closure part 2 even closer to the first closure part 1, the second connection element 22, in this manner, reaches an intermediate position, in which the closure portions 221 thereof are each moved fully past the guide portions 121 of the first connection element 12 and the individual guide portions 121 no longer counter a rotation of the second connection element 22 in the opposite direction of rotation D2.

Under the effect of the spring element 24, in a connecting second phase of a closing operation, the second connection element 22 of the second closure part 2 is then rotated automatically into a closed position corresponding to FIG. 4D. In said closed position, each radially inwardly projecting closure portion 221 of the second connection element 22 engages behind a radially outwardly projecting guide portion 121 of the first connection element 12 at least in part. The two connection elements 121 and 122 are locked together and held together in this way such that they are locked together along the connection axis A and are not easily releasable from one another.

Each closure portion 221 comprises a convex curvature on its end lying in the second direction of rotation D2. By means of said curvature and the sliding surface 2210 provided thereon, the closure portion 221 slides along the surface 1210 of the guide portion 121 under the effect of the magnetic force of the two magnetic elements M1 and M2. In addition, by means of the curvature, the guiding of the closure portion 221 past the guide portion 121 in the second direction of rotation D2 is made easier when the second connection element 22 is transferred into its closed position.

For opening the closure device V, the second connection element 2 has to be rotated relative to the first connection element 12 in the first direction of rotation D1 about the connection axis A corresponding to FIGS. 4E to 4G. A gripping region 220 is provided for this purpose on the second connection element. Said gripping region 220 can be gripped and rotated comfortably with two fingers by a user. If the second connection element 22 is rotated in the first direction of rotation D1—in opposition to the resetting force of the spring element 24—until the individual closure portions 221 no longer engage behind the guide portions 121 of the first connection element 12, the second closure part 2 can be removed from the first closure part 1 along the connection axis A in an opening direction O.

In FIG. 4H, in a view consistent with FIG. 4G, another modified closure device V is illustrated where the portion which provides a guide surface 1210 and the portion which is engaged from behind by a closure portion 221 in order to hold the two closure parts 1, 2 together, come apart. If in the realization variant in FIGS. 1A to 4G, guide portions 121, which are simply spaced apart from one another equidistantly for generating the rotation of the second connection element 22, are provided on a first connection element 12 along its circumference, in the case of the closure device V of FIG. 4G, guide portions 121 and holding portions 124 alternate with one another along the circumference of the first connection element 12. The holding portions 124, in this case, do not realize a guide surface 1210 in each case for generating a rotational movement by the second connection element 22, but, in the closed position, are each engaged from behind by a closure portion 221 of the second connection element 22. In the realization variant shown, two guide portions 121 and two holding portions 124 are provided on the first connection element 12 alternating with one another every 90° along the lateral surface which is circular in cross section, i.e. at 90° (3 o'clock) and 270° (9 o'clock) a guide portion 121 in each case and at 180° (6 o'clock) and 360° (12 o'clock) a holding portion 124 in each case. Apart from this, however, the previously described functions and features remain identical.

It must be pointed out additionally that at least one guide portion can obviously also be replaced by a holding portion in the case of the realization variants explained below in order to perform a functional separation between the guiding and the holding of the second connection element 22 on the first connection element 12 as a result of differently designed portions of the first connection element 12. For example, it is also possible then here in a further development for guide portions with guide surface(s) and holding portion(s) to alternate in pairs along the circumference.

FIGS. 5A to 14D show various views of a second realization variant of a closure device V according to the invention, where identical components are characterized by consistent reference symbols.

Thus, a closure device V of FIGS. 6A to 14 D also comprises two closure parts 1 and 2 which are each designed with multiple parts. The first closure part 1, in this connection, includes, among other things, in conformity with the first realization variant of FIGS. 1A to 4G, a first securing element 11 and a first connection element 12 with guide portions 121 realized thereon. The second closure part 2 additionally comprises a second securing element 21 and an anti-rotation element 23 which is non-rotatably connected thereto and a second connection element 22 which is mounted so as to be rotatable relative to the second securing element 21 and the anti-rotation element 23.

In contrast to the first realization variant of FIGS. 1A to 4G, in the present case instead of an adjusting device based on spring force with a spring element 24, an adjusting device based on magnetic force with two magnetic elements M3 and M4 is provided for prestressing the second connection element 22. The magnetic elements M3 and M4, which are formed here by disk-shaped permanent magnets which are magnetized diametrically, i.e. along their diameter and consequently transversely to connection axis A, are, in this connection, arranged, on one side, on the bearing portion 125 of the first connection element 12 and, on the other side, on a bearing portion 225 of the second connection element 22.

The two magnetic elements M3 and M4 each comprise two magnetic segments M30, M31 or M40, M41 and, in this connection, are arranged in such a manner on the respective closure parts 1 and 2 that different, unlike magnetic poles are each present side by side in a plane which extends transversely to the connection axis A and therefore to the closing direction S. It consequently depends on a relative rotational position of the two closure parts 1 and 2 with respect to one another with reference to the connection axis A as to whether the two magnets M3 and M4 attract or repel. If, for example, the north pole of a magnetic segment M40 of the second closure part 2 and a south pole of the magnetic segment M31 of the first closure part 1 are opposite each other, the south pole of the magnetic segment M41 of the second closure part 2 and the north pole M31 of the first closure part 1 are also opposite each other and the two magnetic elements M3 and M4 attract one another. Where the two magnetic elements M3 and M4 are not aligned in a totally congruent manner with respect to one another with reference to the connection axis A, i.e. when the separation lines, which extend between the magnetic segments M30 and M31 and between M40 and M41, are not aligned in parallel with respect to one another, the magnetic elements M3 and M4 always attempt to align themselves correspondingly with respect to one another such that, in this connection, a torque is then generated in the one or other direction of rotation about the connection axis A.

Use is made of said circumstance in the present case in order to utilize the magnetic elements M3 and M4 as part of an adjusting device, by means of which, when closing the closure device V, the second connection element 22 is acted upon with a magnetic force in its intermediate position. By means of said magnetic force, the second closure element 22 is rotated into a closed position relative to the first connection element 12, in which the closure portions 221 of the second connection element 22 engage behind the guide portions 121 of the first connection element 12.

Figure 7:
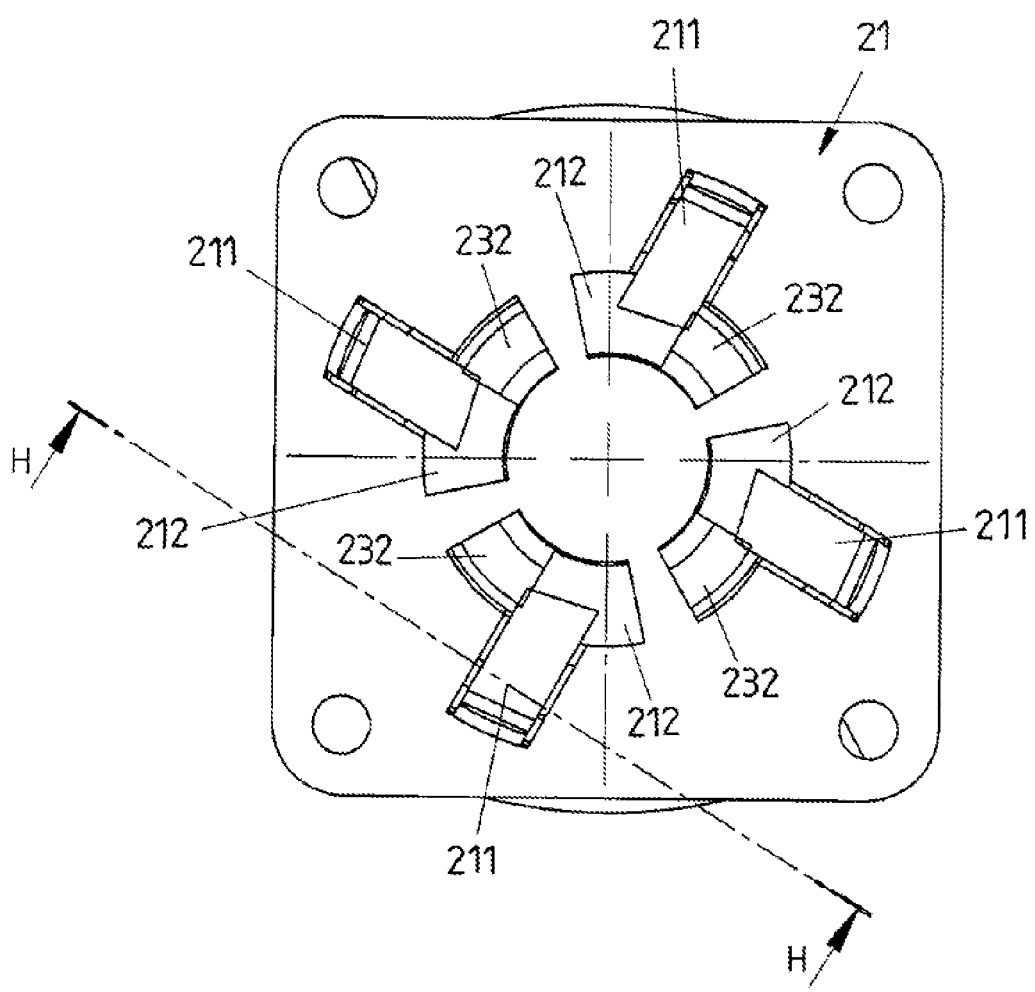
FIG. 7 shows a top view of the closure device of FIGS. 5A to 6C with representation of a cutting line H-H.
Figure 13A:
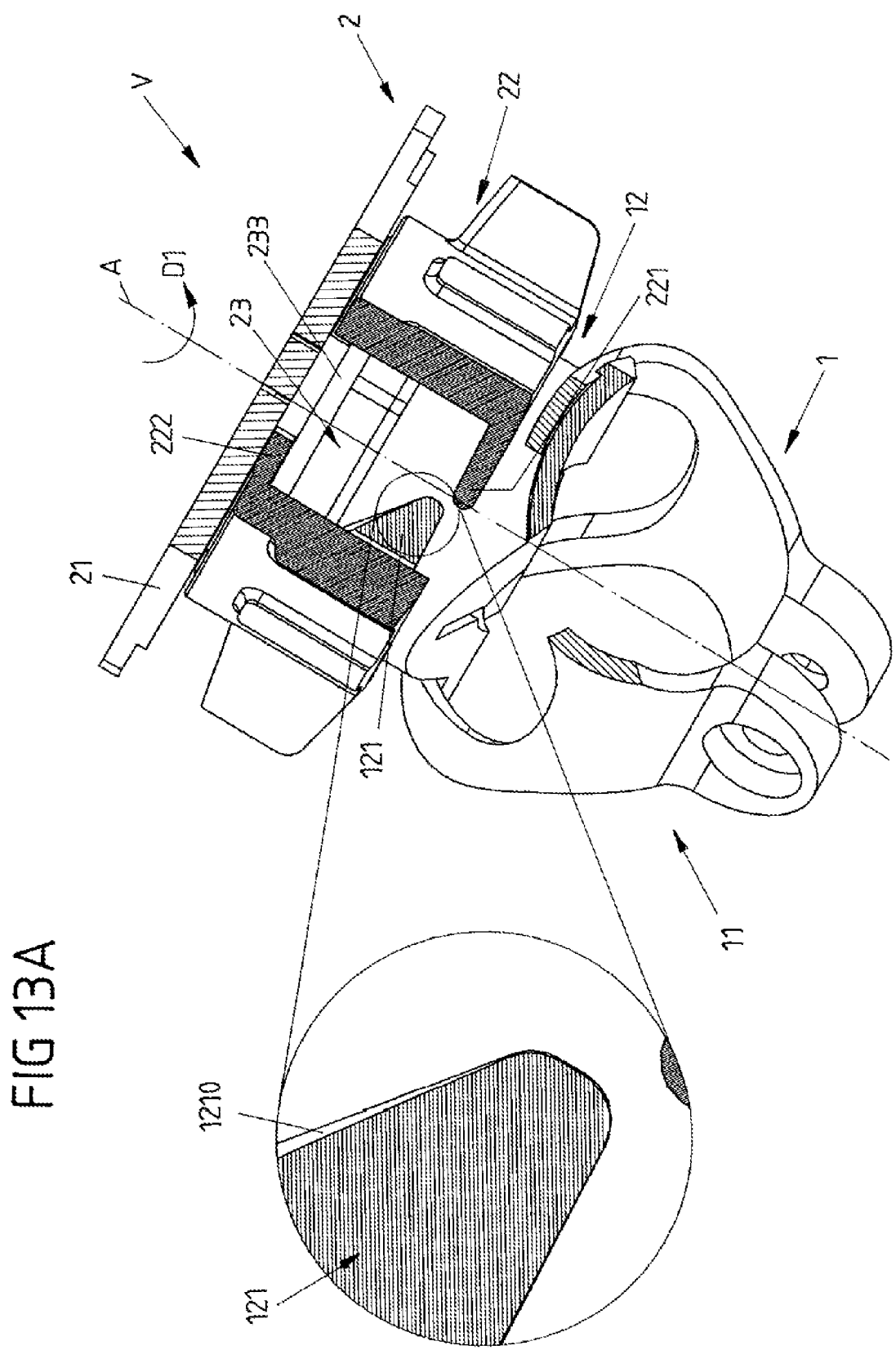
Figure 14A:
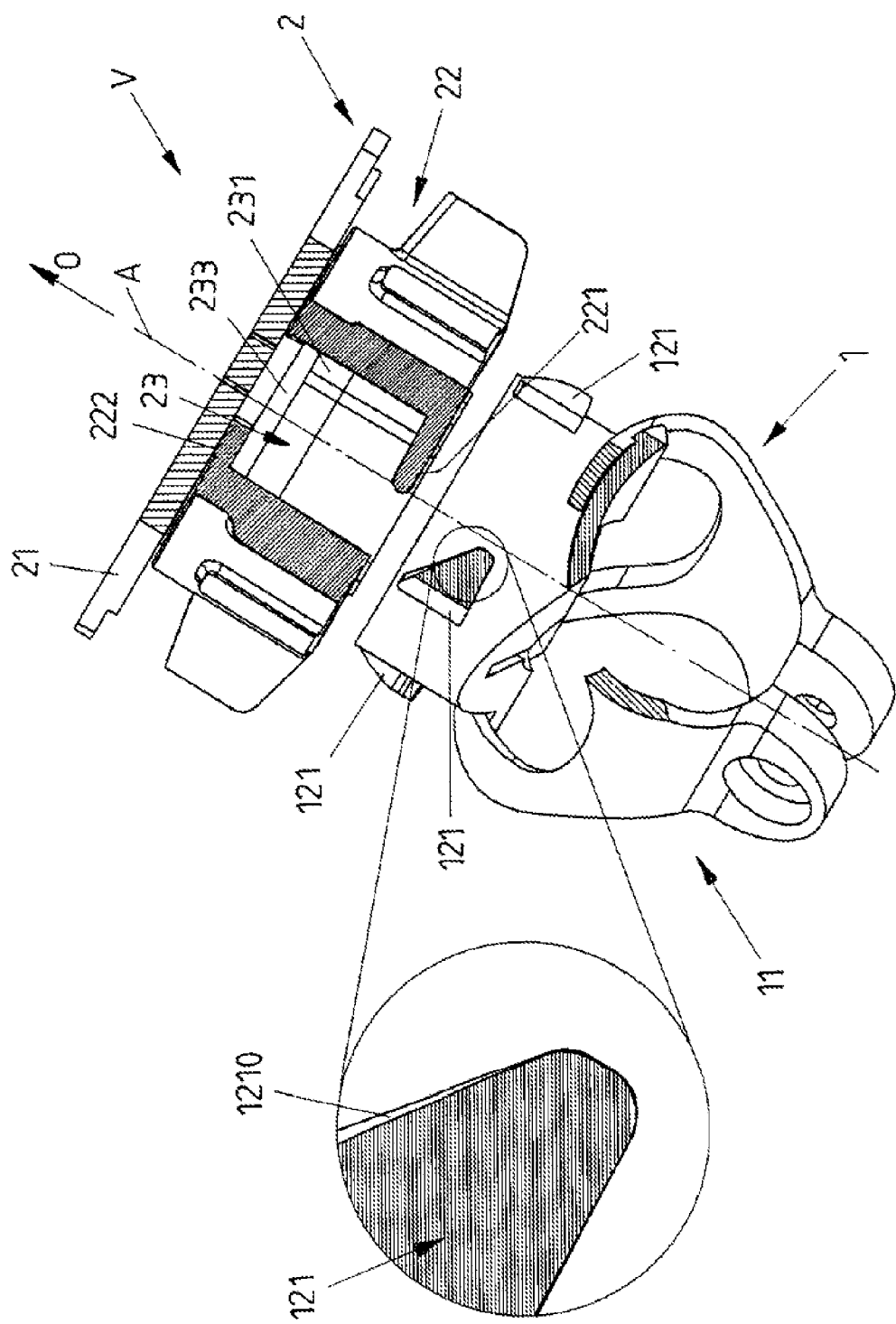
Figure 15C:
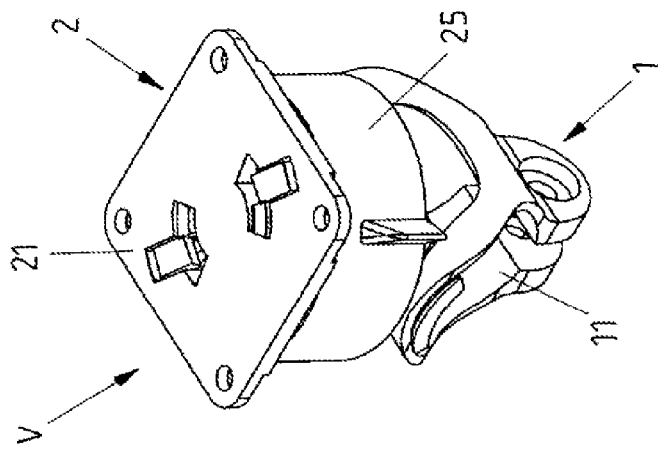
FIGS. 15A to 15C show various views of a third realization variant of a closure device according to the invention in a closed state.
Figure 15B:
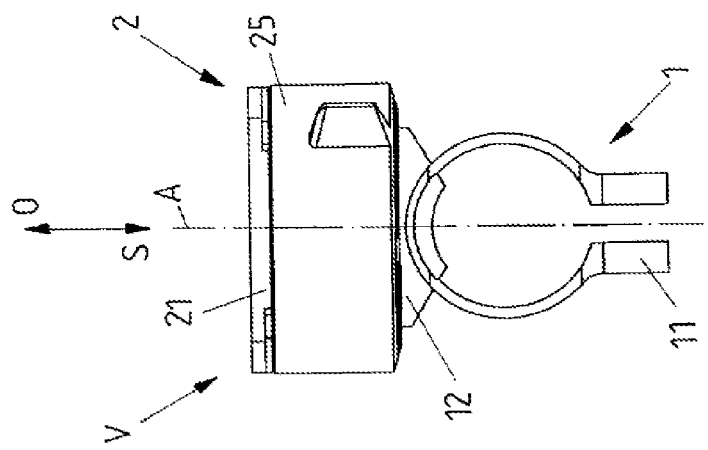
Figure 15A:
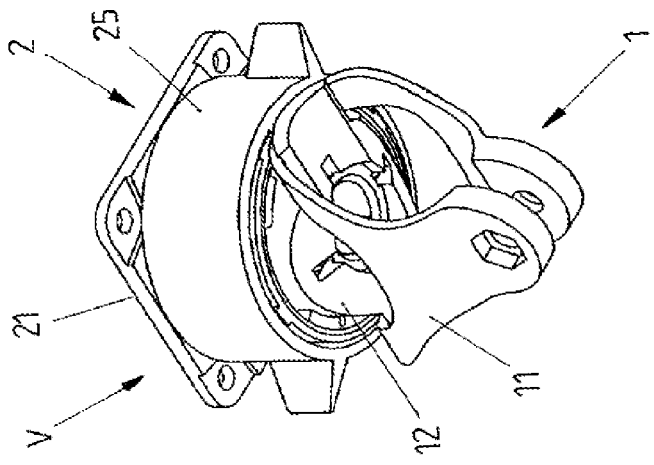
Figure 24A:
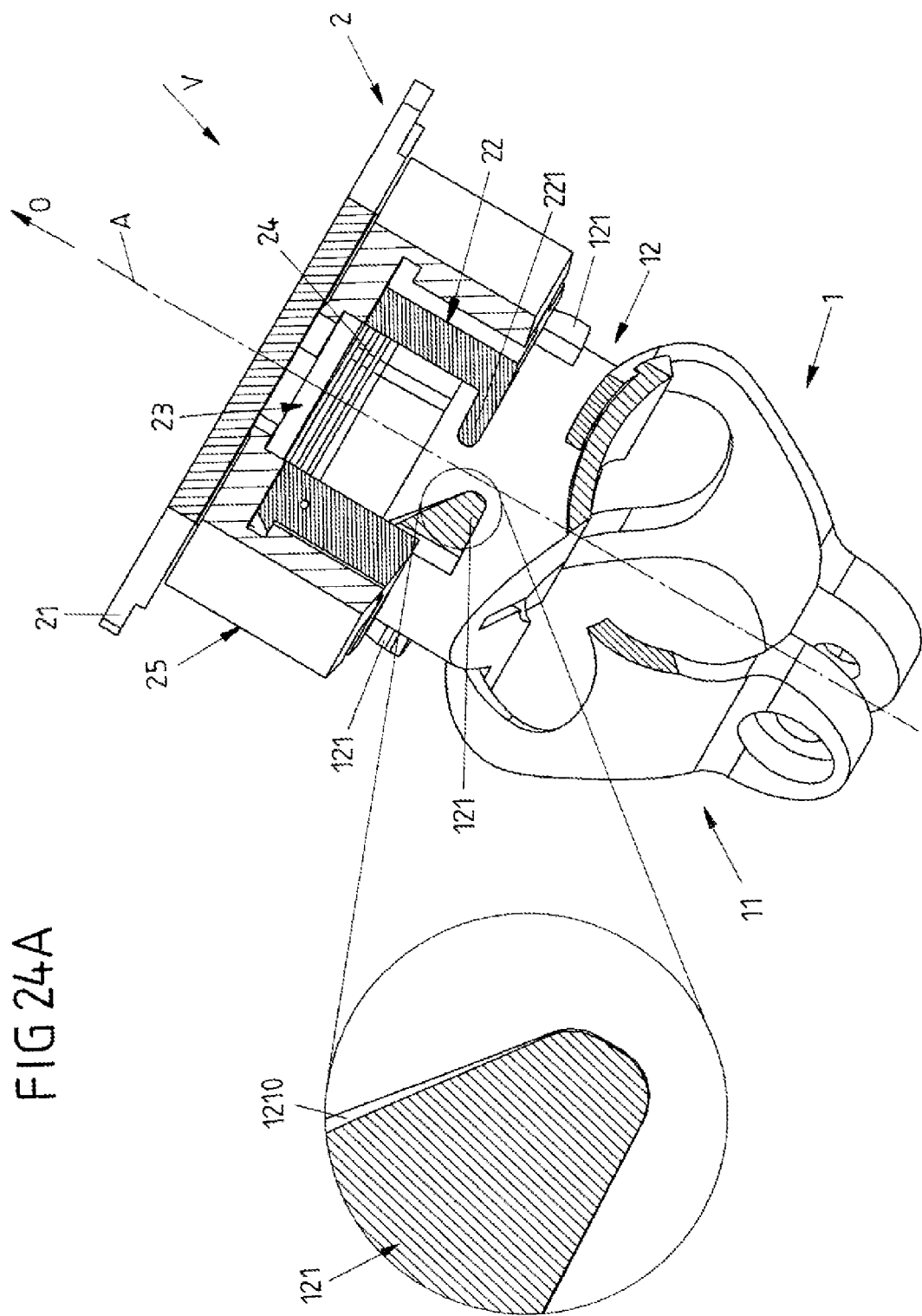

Whilst FIGS. 5A to 5C and 6A to 6C each illustrate the design of the closure device V according to the second realization variant, FIGS. 7 and 8A to 14D clarify the function of the closure device V during closing and opening. In this case, FIG. 7 shows a top view of a cutting line H-H, along which by way of each of the following FIGS. 8A to 14A characterized with an "A", the closure device V is shown in various phases during closing and opening. In FIGS. 8C/8D to 14C/14D, which are respectively designated with "C" and "D", cross sectional representations are shown in each case which are produced from cuts along cutting lines N-N and O-O in FIGS. 8B to 14B which are characterized with "B". The cross sectional representations, in this connection, in particular, illustrate the altering alignment of the diametrically magnetized magnetic elements M3 and M4 of the first and second closure parts 1, 2.

FIGS. 8A to 11D illustrate a first phase of a closing operation when closing the closure device V. In said first phase, the second closure part 2, which is moved toward the first closure part 1 along the closing direction S, is moved closer to the first closure part 1 under the attraction of the magnetic elements M3 and M4. In this connection, the second connection element 22 of the second closure part 2, which is mounted so as to be rotatable on the anti-rotation element 23, is forced to rotate about the connection axis A in the first direction of rotation D1, by the individual closure portions 221 of the second connection element 22 each sliding down the inclined extending guide surfaces 1210 of the individual guide portions 121 of the first connection element 12.

If the second closure part 2 has been moved sufficiently closer to the first closure part 1, such that the closure portions 221, which each extend in the circumferential direction, are each guided past their guide portions 121 in the closing direction S and so that the second connection element 22 is present in an intermediate position which is defined as a result, the two magnetic elements M3 and M4, with reference to their unlike magnetic poles of the two magnetic segments M30, M31 and M40, M41, do not lie exactly one above the other. A diametrically extending separation line of the one magnetic element M3 consequently does not extend parallel to the separation line of the other magnetic element M4. As a result of the efforts of both magnetic elements M3 and M4 to align themselves such that a north pole of the one magnetic element M4 lies directly axially opposite a south pole of the magnetic segment of the other magnetic pole M3, with the second connection 22 in the intermediate position, a torque is generated, by means of which the second connection element 22 is rotated into its closed position in the second direction of rotation D2.

In the closed position corresponding to FIGS. 12A to 12D, each closure portion 221 of the second connection element 22 engages behind an assigned guide portion 121 of the first connection element 12 and the two magnetic elements M3 and M4 are aligned precisely with respect to one another.

If the second connection element 22 is rotated in opposition to the applied magnetic force in the first direction of rotation D1 out of the closed state of the closure device V again, which is defined thereby, as is illustrated by way of FIGS. 13A to 13D, the engagement behind the closure portions 221 can be released. The closure portions 221 are then subsequently guidable past the guide portions 121 in the opening direction O, which is opposite to the closing direction S, and the second closure part 2 can consequently be removed from the first closure part 1, as is illustrated in FIGS. 14A to 14D.

In the case of a closure device V according to a third realization variant corresponding to FIGS. 15A to 26B, an actuating element 25 is also provided on the second closure part 2 in addition to a second connection element 22, an anti-rotation element 23 and a second securing element 21.

The actuating element 25 is realized in a hollow cylindrical manner here and comprises a central bearing portion 255 in which the second diametrically magnetized magnetic element M4 is arranged. The actuating element 25 is rotatably mounted on the securing collar 233 of the anti-rotation element 23 by means of radially inwardly projecting bearing webs 252. The second connection element 22 of the second closure part 2, in this connection, is, in turn, rotatably retained on the actuating element 25. For this purpose, the second connection element 22 realizes radially projecting projections 224, by means of which the second connection element 22 is rotatably retained on the actuating element 25. With the second closure part 2 in the assembled state, the second connection element 2 is then surrounded circumferentially about the connection axis A by the actuating element 25 and is arranged between the actuating element 25 and the anti-rotation element 23.

A spring element 24, which is realized here once again as a leg spring, is mounted on the anti-rotation element 23 on a spring bearing region 234. The spring element 24 is supported at one end on the anti-rotation element 23 and at the other end on the second connection element 22 such that the second connection element 22 is elastically prestressed by means of the spring element 24 relative to the anti-rotation element 23. The spring element 24 consequently here forms part of an adjusting device in the second closure part 2, by means of which the second connection element 22 is acted upon with a force in the closing direction when closing the closure device V in order to engage behind the guide portions 121 of the first connection element 12 of the first closure part 1 by means of its closure portions 221. The closure portions 221, in this connection, are realized in a lower region, with reference to the closing direction S, on an inner lateral surface of the second connection element 22. The multiple, here four, closure portions 221, which are arranged equidistantly to one another, consequently lie on an inside surface of the second connection element 22, whilst the projections 224 are provided on an outer lateral surface of the second connection element, and consequently on the outside surface thereof. Said projections are situated apart from this on an upper region of the second connecting portion 22.

Elongated counter stops 223a and 223b, which extend parallel to the closing direction S, are also additionally realized in the present case on the outer lateral surface of the second connection element 22. Rotatability of the actuating element 25 relative to the second connection element 22 is limited by means of said counter stops 223a and 223b interacting with a radially inwardly projecting stop 251 of the actuating element 25. For this purpose, the stop 251 of the actuating element 25 is arranged between the two counter stops 223a and 223b such that the actuating element 25 is not able to be adjusted beyond one of the counter stops 223a, 223b in either possible direction of rotation D1 and D2 about the connection axis A or the closing direction S. For example, via the counter stops 223a and 223b, the rotatability of the actuating element 25 relative to the second connection element 22 is limited to a range of rotational angle of less than 90°, in particular less than 80°, for example here 70°.

As a result of interaction between the one counter stop 223a of the second connection element 22 and the stop 251 of the actuating element 25, the actuating element 25 is entrained in the first direction of rotation D1 when the closure device V is closed. For opening the closure device V, the stop 251 additionally interacts with the other counter stop 223b in order to entrain the second connection element 22 when rotating the actuating element 25 in the first direction of rotation D1. This will be explained again below in more detail by way of FIGS. 18A to 25D.

Whereas each of FIGS. 15A to 15C and 16A to 16C illustrate the design of the closure device V according to the third realization variant, FIGS. 17 and 18A to 18D clarify the function of the closure device V during closing and opening. In this case, FIG. 17 shows a top view of a cutting line H-H, along which by way of each of the following FIGS. 18A to 25A characterized with an "A", the closure device V is shown in various phases during closing and opening. In FIGS. 18C/18D to 25C/25D, which are respectively designated with "C" and "D", cross sectional representations are shown in each case which are produced from cuts along cutting lines N-N and O-O in FIGS. 18B to 25B which are characterized with "B". The cross sectional representations, in this connection, in particular, illustrate the altering alignment of the diametrically magnetized magnetic elements M3 and M4 of the first and second closure parts 1, 2 as well as the interaction between the second connection element 22 and the actuating element 25.

When closing the closure device V, illustrated by way of FIGS. 18A to 21D, in an analogous manner to the realization variant of FIGS. 5A to 14D, the two diametrically magnetized, disk-shaped magnetic elements M3 and M4 attract one another in order to move the closure parts 1 and 2 even closer to one another once the second closure part 2 has been moved along the connection axis A in the closing direction S toward the first closure part 1. The effect of the magnetic elements M3 and M4 is, in this respect, functionally identical to the second realization variant, although the magnetic element M4 of the second closure part 2 is not arranged in the second connection element 22, but in the actuating element 25.

As a result of the two closure parts 1 and 2 being moved closer together, supported by means of the magnetic elements M3 and M4 or even proceeding fully automatically, and of the closure portions 221 sliding along the guide portions 121, the second connection element 22 is also forced, here too, to rotate in the first direction of rotation D1 about the connection axis V and the closing direction S. In this connection, the second connection element 22 presses against the stop 251 of the actuating element 25 by means of its one counter stop 223a and in this way entrains the actuating element 25 in the first direction of rotation D1 such that said actuating element is also rotated in the first direction of rotation D1 in the first phase of the closing operation (compare for example FIGS. 20A to 20D).

Once the second connection element 22 has reached its intermediate position relative to the first connection element 12 and the closure portions 221 are no longer impeded from rotating in the opposite direction of rotation D2 by the guide portions 121, the second connection element 22 is rotated automatically into the closed position under the effect of the spring force of the spring element 24. Said closed position is illustrated in more detail in FIGS. 21A to 21D. The spring element 24, in this connection, has been (more strongly) stressed in the preceding first phase of the closing operation as a result of rotating the second connection element 22 relative to the anti-rotation element 23, which is connected non-rotatably to the first connection element 12, such that, with the second connection element 22 in the intermediate position, a sufficiently high resetting force is available for rotating the second connection element 22 into its closed position.

For opening the closure device V, first of all, corresponding to FIGS. 22A to 22D, the actuating element 25 is rotated in the first direction of rotation D1 about the connection axis A. In this connection, the actuating element 25 has first of all to bridge a void rotational path which is defined by the distance between the two counter stops 223a and 223b, during which the actuating element 25 does not yet act on the second connection element 22. Not until the actuating element 25 has been rotated by a certain amount—in the present case by approximately 70°—does it interact with the second connection element 22 by means of its stop 251 by the stop 251 contacting the counter stop 223b. The actuating element 25, which can be gripped for this purpose at a gripping region 250 by a user, consequently does not entrain the second connection element 22 in the first direction of rotation D1 until the void rotational path has been bridged.

If the actuating element 25 is then rotated further in the first direction of rotation D1, said rotation is effected not only against a torque applied by means of the magnetic elements M3 and M4, but also against the resetting force of the spring element 24, when the second connection element 22 is entrained (compare in particular FIGS. 23A to 23D).

The first and second closure parts 1 and 2 are designed and matched to one another in the present case such that, when opening the closure device V, the second connection element 22 is permitted to rotate relative to the first connection element 12 beyond the intermediate position. In this way, the actuating element 25 can be rotated with reference to the first connection element 12 in the first direction of rotation D1 about the connection axis A by such an amount that the magnetic elements M3 and M4 of the two closure parts 1 and 2 are present in such a rotational position relative to one another that like magnetic poles of the two magnetic elements M3 and M4 are opposite one another with a greater overlap in such a manner that the two magnetic elements M3 and M4 repel one another. The releasing of the two closure parts 1 and 2 is consequently supported by the magnetic elements M3 and M4. Thus, as a result, the second closure element 2 is repelled in the opening direction O by the first closure element 1 when opening the closure device V, as is illustrated by way of FIGS. 24A to 24D and 25A to 25.

The two magnetic elements M3 and M4, which are arranged on one side on the first connection element 12 and on the other side on the actuating element 25, consequently support both the moving closer together of the two closure parts 1 and 2 when closing the closure device V and the releasing thereof from one another when opening the closure device V. The adjusting device, which is provided to generate a resetting force on the second connection element 22 in the direction of its closed position, is, in contrast, not based on magnetic force but works purely mechanically based on spring force by means of the spring element 24.

Figure 26A:
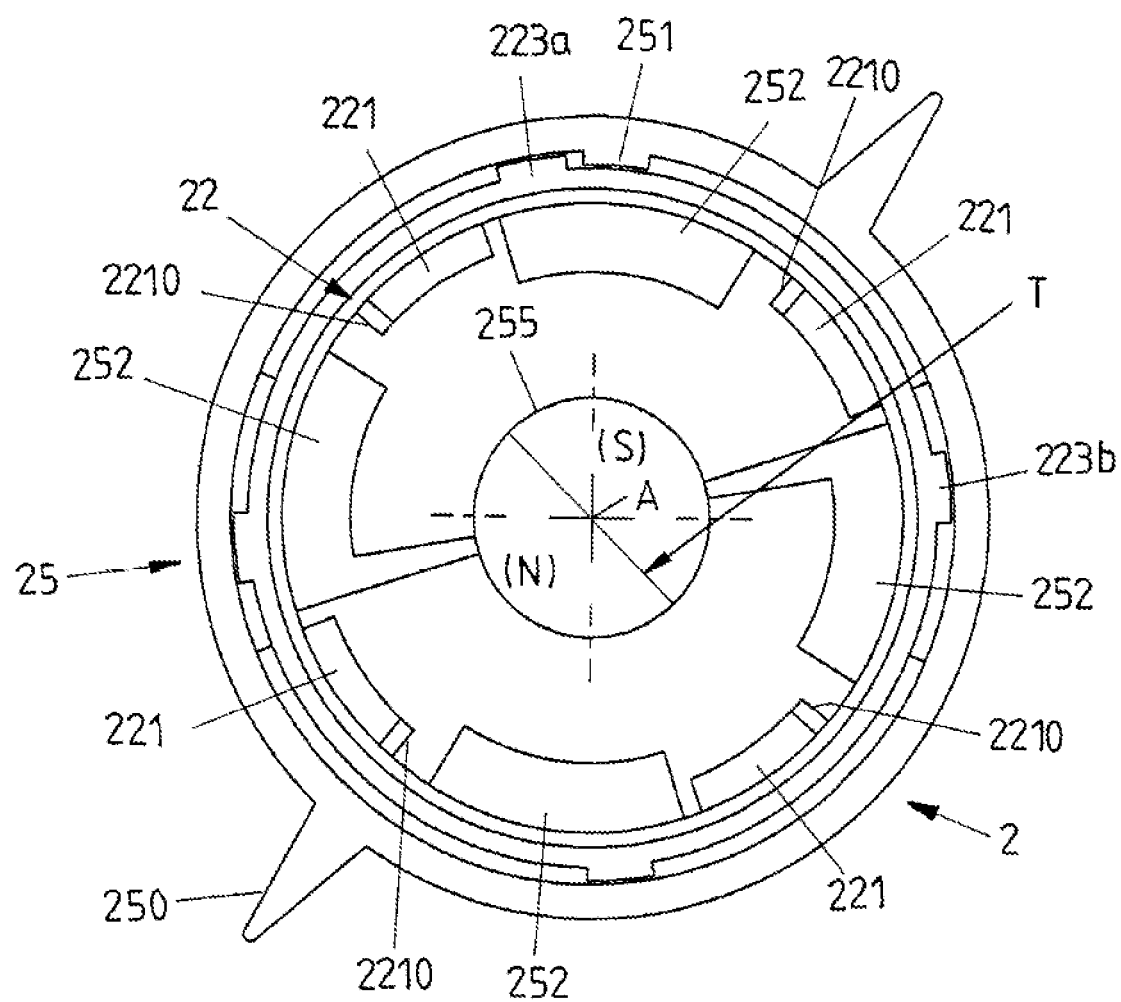
FIG. 26A shows a view of the underside of a second closure part of the closure device of FIGS. 15A to 16C with the closure device in a closed state.
Figure 26B:
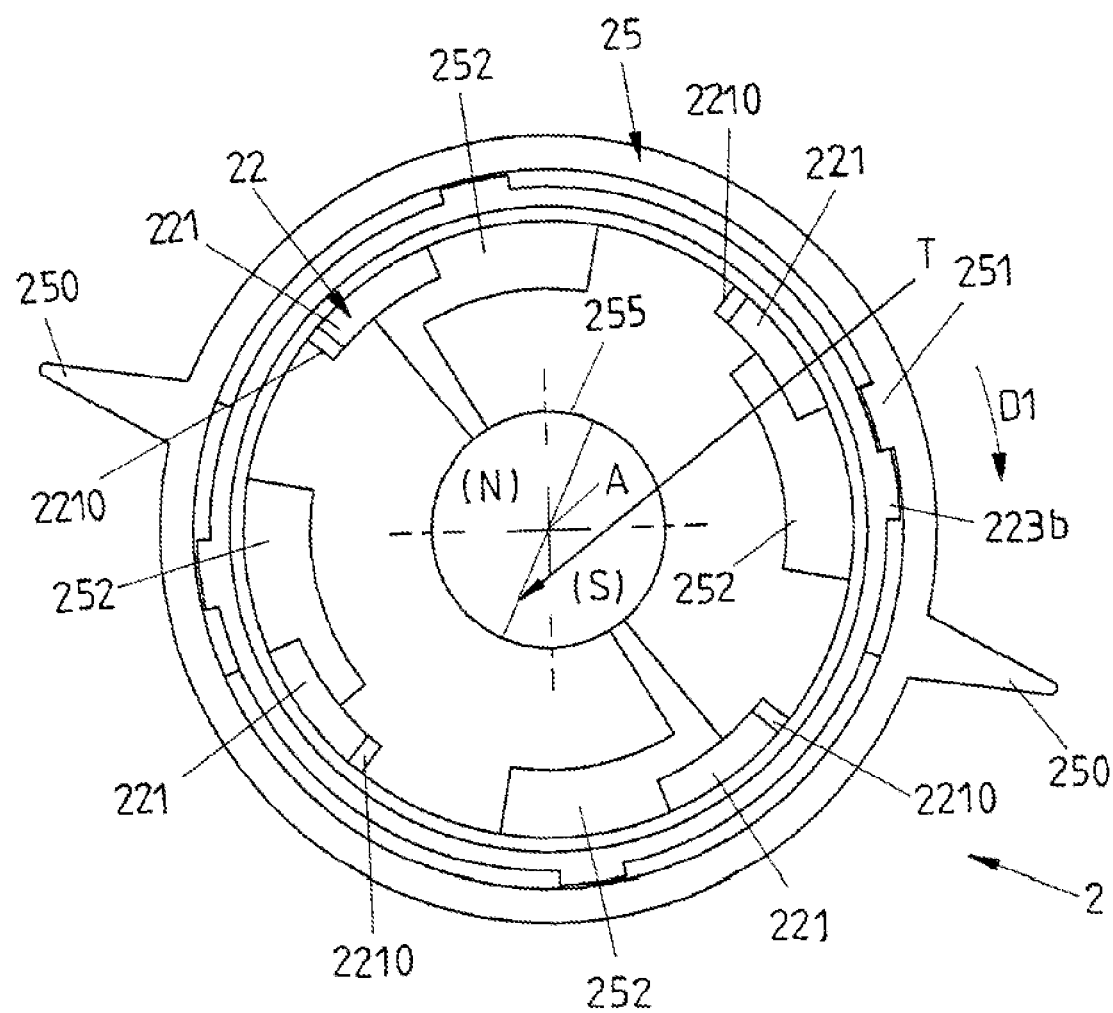
FIG. 26B shows a view from below of the second closure part, where to open the closure device, an outer actuating element has been rotated in a first direction of rotation (here clockwise)
Figure 29A:
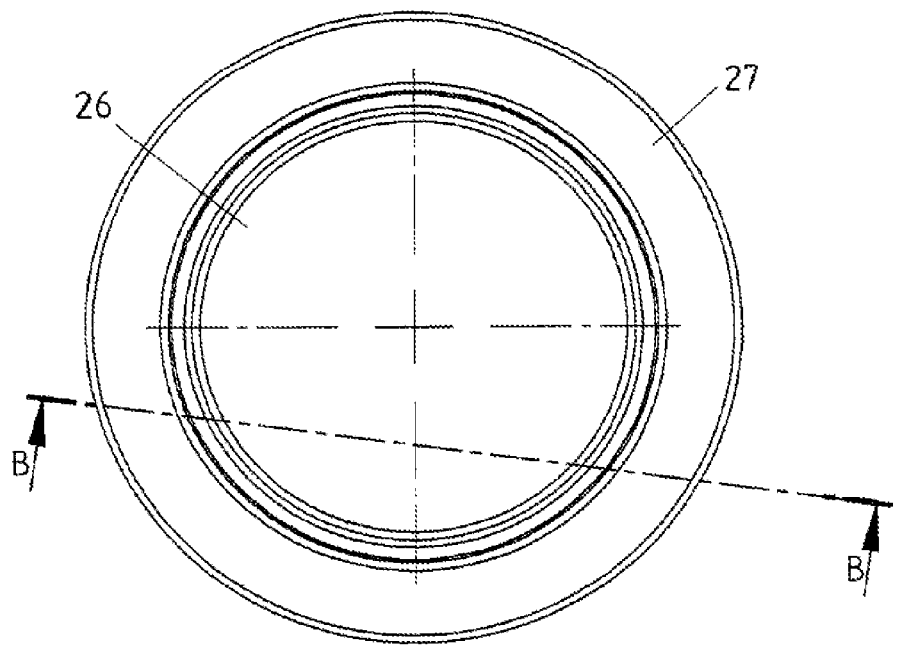
FIGS. 29A to 36E show consistent views in each case of the closure device of FIGS. 27A to 28C in various phases during closing and opening, five views having been chosen in each case to illustrate the various phases.
Figure 29B:
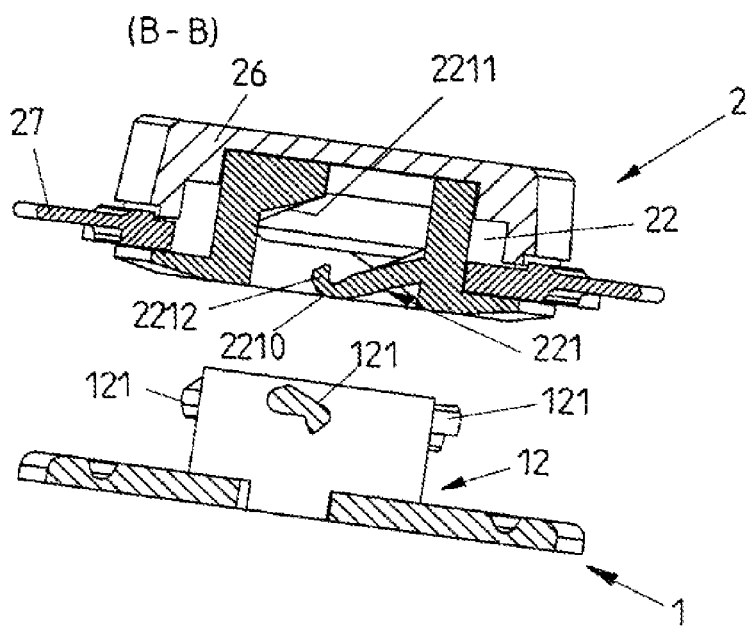
Figure 30A:
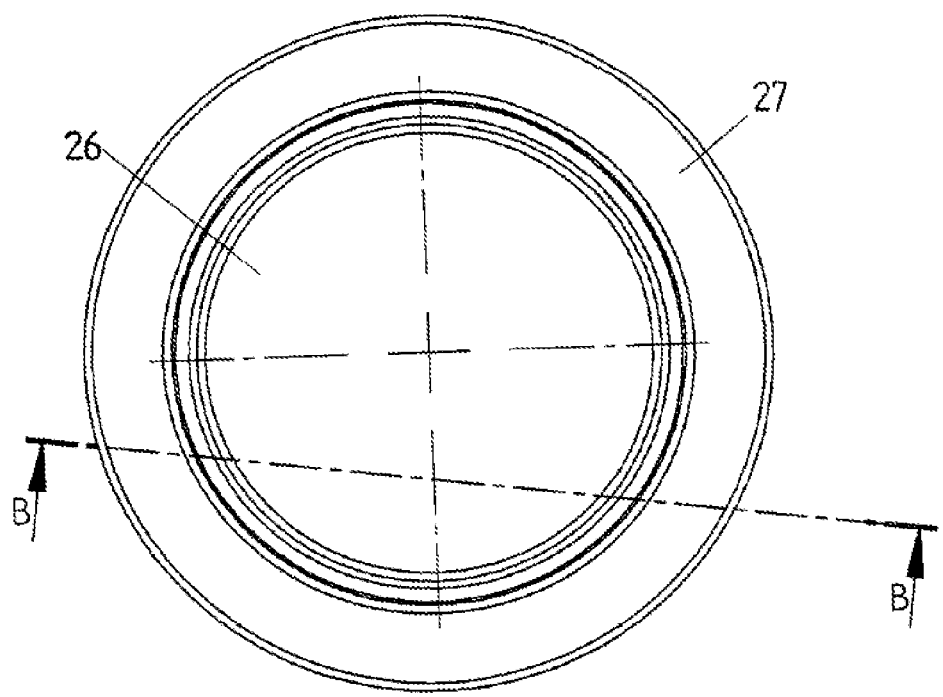
Figure 30B:
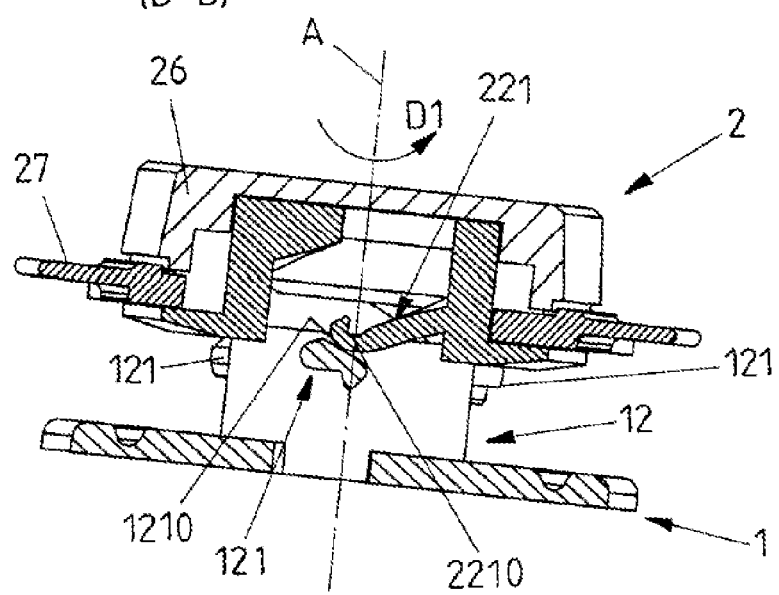
Figure 31A:
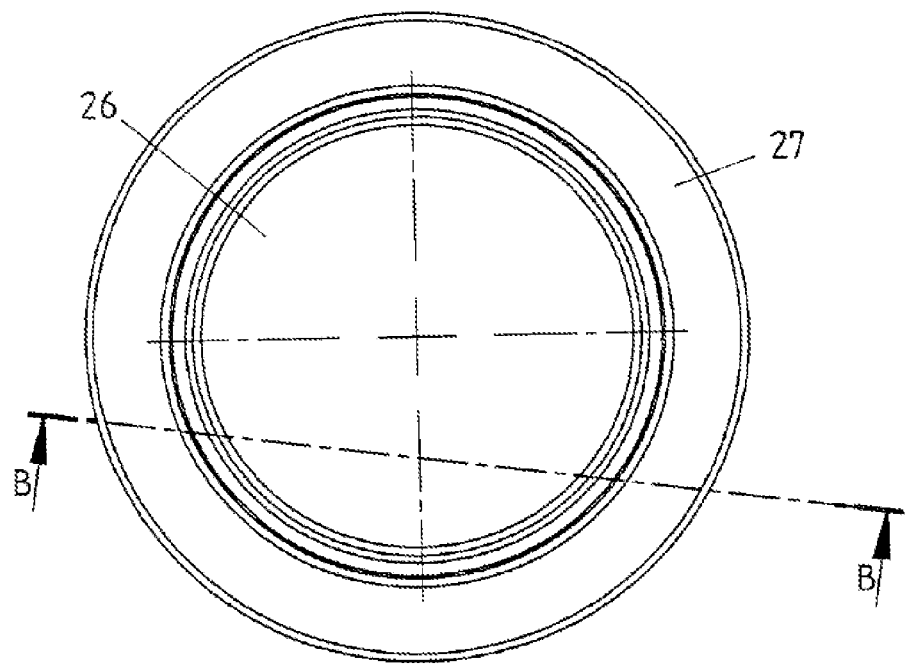
Figure 31B:
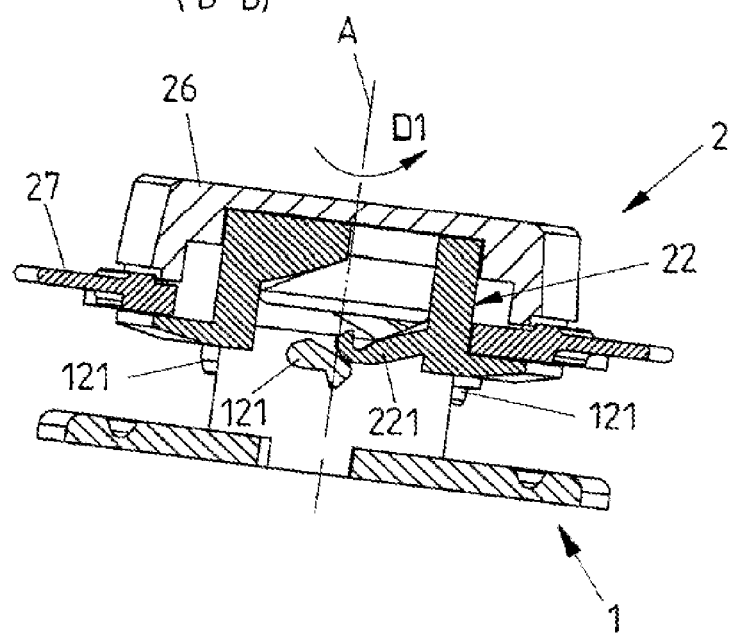
Figure 32A:
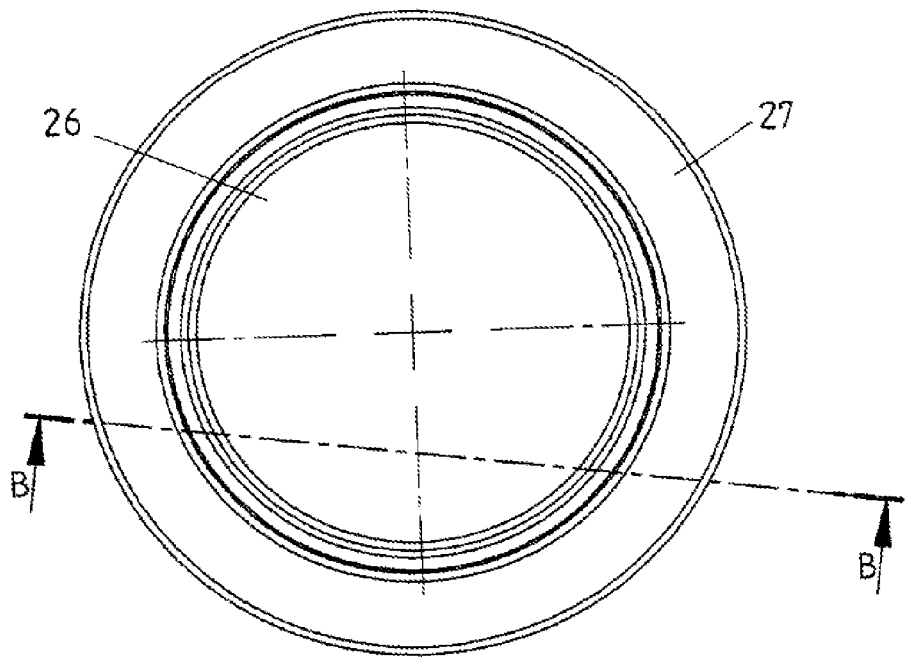
Figure 32B:
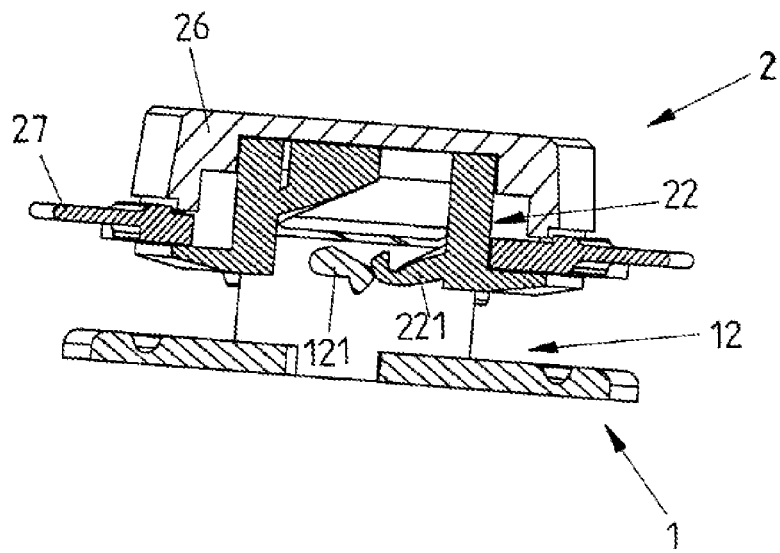
Figure 33A:
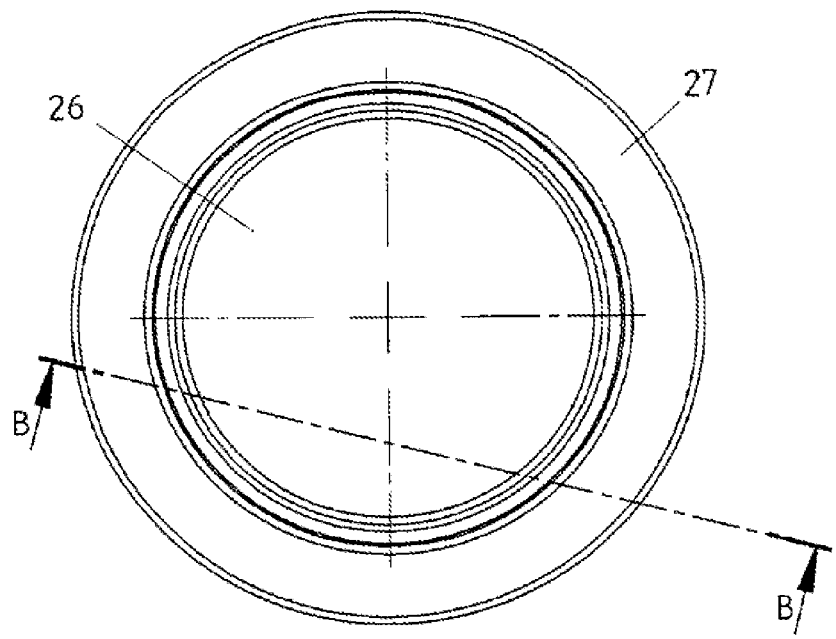
Figure 33B:
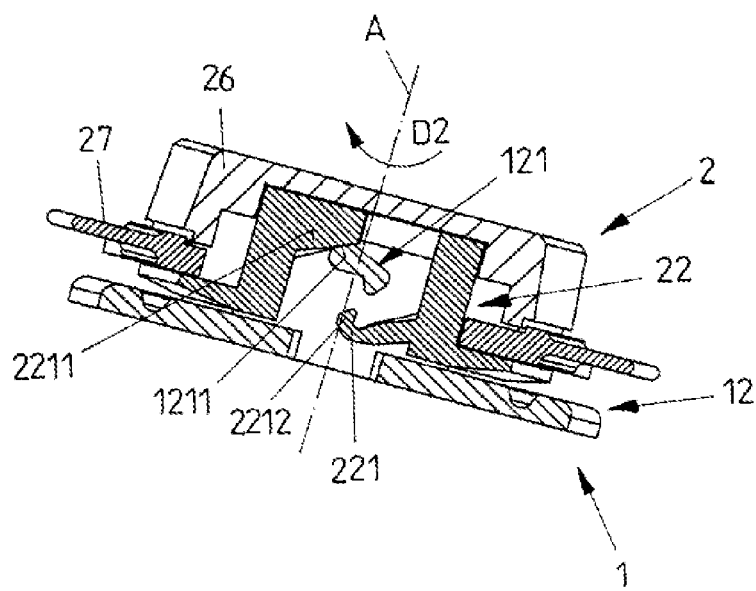

Looking at an underside of the second closure part 2, the relative movement of the actuating element 25 with reference to the second connection element 22 when opening the closure device V is illustrated in detail by way of FIGS. 26A and 26B. In this connection, FIG. 26A shows the relative position of the actuating element 25 with respect to the second connection element 22 with the closure device V closed as intended, whilst FIG. 26B shows the state in which the actuating element 25 has already been rotated by 70° in the first direction of rotation D1 in order to bridge the void rotational path. It can be seen in particular from the two named figures how the stop 251 of the actuating element 25, which is present initially in the region of the one counter stop 223a, can be moved into contact with the other counter stop 223b as a result of rotating the actuating element 25 in the first direction of rotation D1 in order to entrain the second connection element 22 when rotating the actuating element 25 further in said direction of rotation D1. In addition, as a result, the separation line T, which shifts in the first direction of rotation D1 (clockwise here) between the magnetic segments M40 and M41 of the magnetic element M4, which is mounted non-rotatably on the actuating element 25, is also illustrated in an enlarged scale.

Whereas the previously described closure devices V according to FIGS. 1A to 4G, 5A to 14D and 15A to 26B concentrate on realization variants where the closure parts 1 and 2 are provided with securing elements 11 and 21 by means of which a connection between an object and a tubular carrier element, for example an electronic device and handlebars, is possible, FIGS. 27 to 36D illustrate a variant of a closure device V which is suitable, in particular, for a closure for an item of clothing, a shoe and/or a prosthesis. Said closure device V, in this case, also comprises two closure parts 1 and 2 which can be moved toward one another, are releasably connectable to one another and are held together by means of two connection elements 12 and 22 with the closure device V in a closed state by closure portions 221, which are realized on a (second) connection element 22, engaging behind guide portions 121 which are realized on the other (first) connection element 12 of the first closure part 1.

The first connection element 12 of the first closure part 1 in said variant also comprises a hollow cylindrical connecting body which is surrounded by the hollow cylindrical second connection element 22 in the closed state. The radially outwardly projecting guide portions 121 are provided on an outer lateral surface of the connecting body of the first connection element 12. In the present case, said guide portions comprise, along with a (first) guide surface 1210 which extends at an angle to the connection axis A and to the closing direction S, an additional (second) guide surface 1211. The additional guide surface 1211 extends at an angle of greater than 90°—in the present case approximately 120°—with respect to the other guide surface 1210 also at an angle to the connection axis V and sloping away in the closing direction S. Depending on whether the closure device V is closed or opened, the second connection element 22 is supported on the one or the other guide surface 1210, 1211 and is guided thereby. This will be explained in more detail below.

To generate a magnetic force which attracts the two closure parts 1 and 2 together when closing the closure device V, once again magnetic elements M3 and M4 are provided with two magnetic segments which comprise unlike poles which are separated from one another by a separation line which extends transversely to the closing direction S. The magnetic elements M3 and M4, in this connection, are each realized in a cuboid manner and on one side are received in a positive locking manner in a bearing portion 125 of the first connection element 12 and on the other side in a bearing portion 225 of the second connection element 22. The bearing portion 225, which is realized centrally on the second connection element 22, for the magnetic element M4 is surrounded, in this case, all around by an inner lateral surface of the second connection element 22, on which are realized the closure portions 221 which extend longitudinally along a helical line in each case at least in part.

A stop 227 is realized on an outer lateral surface of the second connection element 22. Said radially outwardly protruding stop 227 is received, with the second closure part 2 in the assembled state, in a recess of a stop ring 27 of the second closure part 2, said recess extending in an arcuate manner between two counter stops 271a and 271b. The stop ring 27, in this case, serves as a securing element, by means of which the second closure part 2 is fixed to an object, for example to a closure flap of an item of clothing, of a shoe or a prosthesis. The second connection element 22 is mounted on said stop ring 27 so as to be rotatable about the connection axis A.

Travel limitation is realized on the stop ring 27, in this case, by means of the counter stops 271A and 271B such that the second connection element 22 is only rotatable within a defined range of rotational angle below 180°, in the present case below 150°, for example within the range of approximately 120°, relative to the stop ring 27. This ensures that the two magnetic elements M3 and M4 of the two closure parts 1 and 2 cannot be aligned with respect to one another in an unwanted relative position, in which, for example, the two magnetic elements M3 and M4 repel one another when closing the closure device V. As a result of the travel limitation on the stop ring 27, it is ensured, in contrast, that the second connection element 22, and consequently the magnetic element M4 thereof, is present when closing the closure device V in a relative position with reference to the connection axis A with respect to the first connection element 12 and the magnetic element M3 thereof, in which the two magnetic elements M3 and M4 attract one another. Thus, in particular in the case of said exemplary embodiment, with an adjusting device which is based on magnetic force, on the basis of the respectively diametrically magnetized magnetic elements M3 and M4, the connection elements 12 and 22 can be acted upon, in principle, in both possible directions of rotation D1 and D2 with a resetting torque in the direction of a closed position, depending on the relative position of the magnetic elements M3 and M4 and consequently depending on the relative position of the connection elements 12 and 22 with respect to one another. This allows, for example when compared with an adjusting device which is based on spring force, the closure device V to be designed in a very compact manner and the choice of the directions of rotation for closing and opening to be application-dependent, as rotatability in both directions is not limited by the adjusting device per se.

The second closure part 2 additionally includes another rotational element 26 which is provided for fixing the second connection element 22 to the stop ring 27 and with which a user is able to cooperate in order to open the closure device V by actuating the rotational element 26. For this purpose, the stop ring 27 is arranged between the cover-like rotational element 26 and the second connection element 22. The hollow cylindrical connecting body of the second connection element with the bearing portion 225 for the magnetic element M3, in this connection, extends right through the central opening of the stop ring 27 and is connected to the rotational element 26 in a positive locking manner.

An insertion slot 228 is provided on the connecting body of the second connection element 22 for the positive locking connection between the second connection element 22 and the rotational element 26. Said insertion slot protrudes at a radially outer region of the connecting body and extends into an outer wall of the connecting body both in the radial and the axial direction. A radially inwardly protruding connecting web 260, which is inserted in a positive locking manner into said insertion slot 228 of the second connection element in order to connect the rotational element 26 non-rotatably to the second connection element 22, is provided, in turn, on the rotational element 26.

Whilst the different views in FIGS. 27A to 27C and 28A to 28C clarify the previously depicted design of the closure device V, FIGS. 29A to 36E illustrate the function of the closure device V by way of representations at different phases during the closing and opening of the closure device V. In this connection, each FIG. 29A to 36A which is characterized with "A" shows a top view of the closure device V, thereby showing a representation of a cutting line B-B. The longitudinally cut sectional representation of FIGS. 29B to 36B which are characterized in each case with "B" is obtained along said cutting line B-B. FIGS. 29C/29D to 36C/36D which are characterized with "C" and "D" each show cross sectional representations along the cutting lines C-C and D-D of the respectively associated FIGS. 29E to 36E which are characterized with "E".

As is illustrated by way of FIGS. 29A to 32E, the second connection element 22, once the second closure part 2 has been moved closer to the first closure part 1, is forced to rotate in the first direction of rotation D1 about the connection axis A as a result of each of the closure portions 221 sliding on a guide portion 121 when the second closure part 2 is moved even closer to the first closure part 1 in the closing direction S. An end of the respective closure portion 221, which in the present case is hook-shaped, slides, in this case, with a sliding surface 2210 which is realized on an underside, along the (first) guide surface 1210, which extends at an angle, of a guide portion 121.

If the connection element 22 has been displaced by a sufficient amount relative to the first connection element 12 in the first direction of rotation D1 such that an end of the respective closure portion 221 can be guided past the assigned guide portion 121 in the closing direction S, the second connection element 22 assumes an intermediate position relative to the first connection element 12. On account of the separation lines of the two magnetic elements M3 and M4, which are magnetized transversely to the closing direction S, not being aligned parallel to one another, a magnetic force then acts, however, in said intermediate position, as a result of which the second connection element 22 attempts to assume a relative position to the first connection element 12, in which each guide portion 121 is engaged from behind at least in part by a closure portion 221. Consequently, an adjusting device is provided by the magnetic elements M3 and M4, by means of which the second connection element 22 is automatically rotated out of its intermediate position into a closed position about the connection axis A in the second direction of rotation D2, which is opposite to the first direction of rotation D1. In the two phases of a closing operation following one after the other when closing the closure device V, there is consequently a change in directions of rotation along which the second connection element 22 carries out a rotational movement relative to the first connection element 12 in order to be held as intended on the first connection element 12.

With the closure device V in a state which has been closed as intended and is illustrated by way of FIGS. 33A to 33D, the individual closure portions 221 of the second connection element each protrude in the axial direction (with reference to the connection axis A) at a spacing to a guide portion 121. In this way, the two connection elements 12 and 22, and consequently the closure parts 1 and 2, are displaceable by a defined axial clearance which is defined by the axial distance between a guide portion 121 and a closure portion 221.

In order, in this connection, nevertheless to ensure axial securement of the two closure parts 1, 2 together such that the two closure parts 1, 2 are able to be easily separated from one another along the connection axis A, each guide portion 121 comprises, on an end lying in the direction of rotation D1, a (first) hook-shaped blocking part 1212. Complementary to this, on an end of each closure portion 221 lying in the second direction of rotation D2 is realized a (second) hook-shaped blocking part 2212. If the closure device V, which has been closed as intended, is loaded along the connection axis A with a resultant force by means of which the two closure parts 1 and 2 are to be removed from one another, the two closure parts 1 and 2 can be displaced axially by the defined clearance. As a result, the two blocking parts 1212 and 2212 of the two connection elements 12 and 22 engage one another in a positive locking manner. As a result of said positive locking engagement, the two connection elements 12 and 22 are no longer rotatable relative to one another. Not until corresponding release and resultant renewed movement of the two closure parts 1 and 2 closer together do the two hook-shaped blocking parts 1212 and 2212 move out of engagement again and the second closure part 2 can be rotated in the first direction of rotation D1 about the connection axis A relative to the first connection element 12 such that the closure portions 221 no longer engage behind the guide portions 121 and the second closure part 2 is able to be removed from the first closure part 1 in the opening direction O along the connection axis A. This is illustrated in more detail by way of FIGS. 34A to 36E.

Figure 34A:
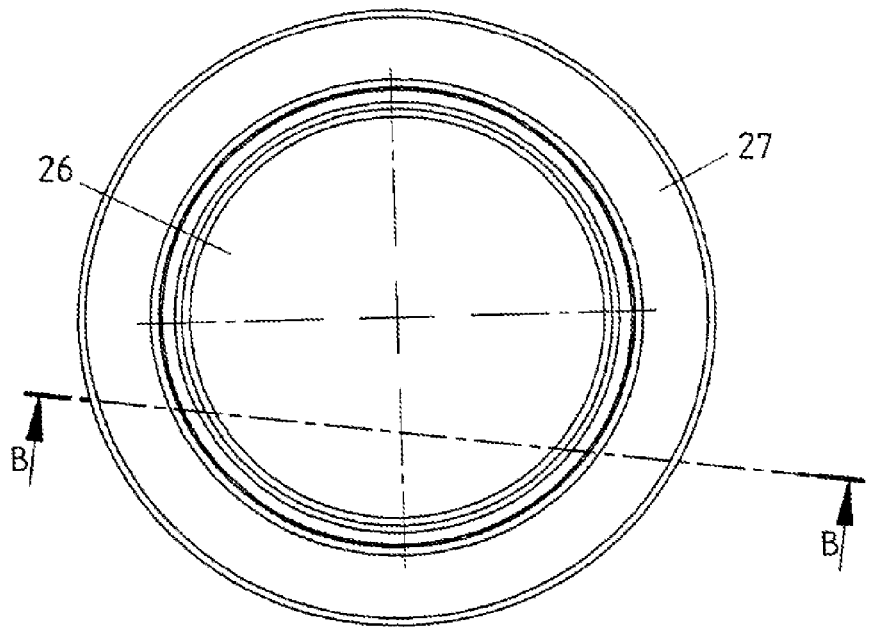
Figure 34B:
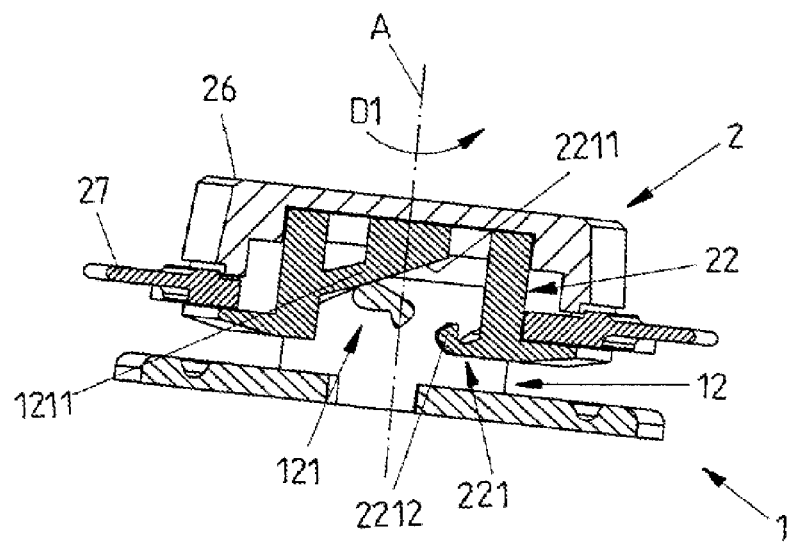
Figure 35A:
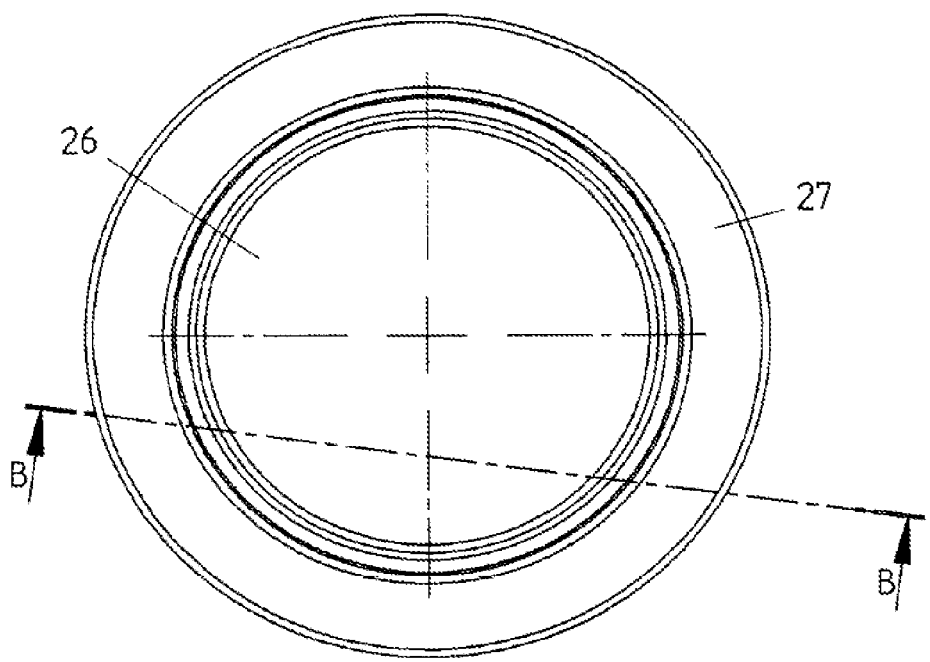
Figure 35B:
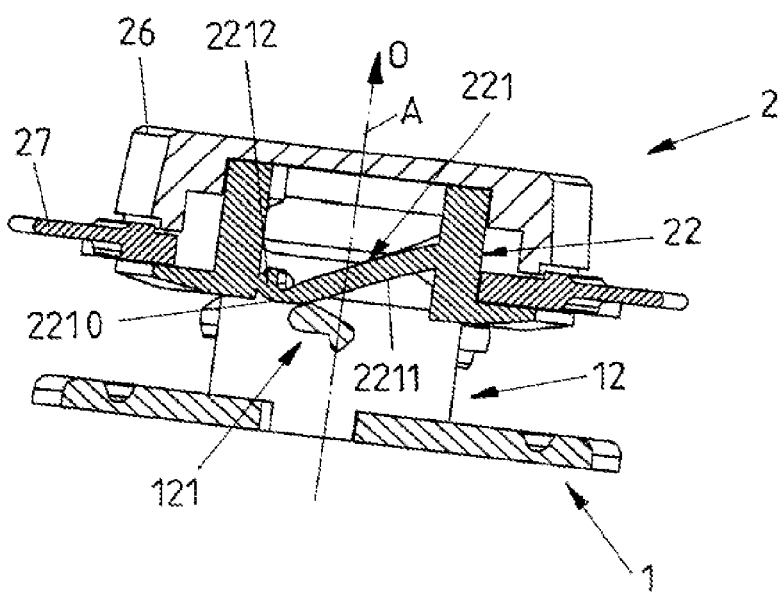
Figure 36A:
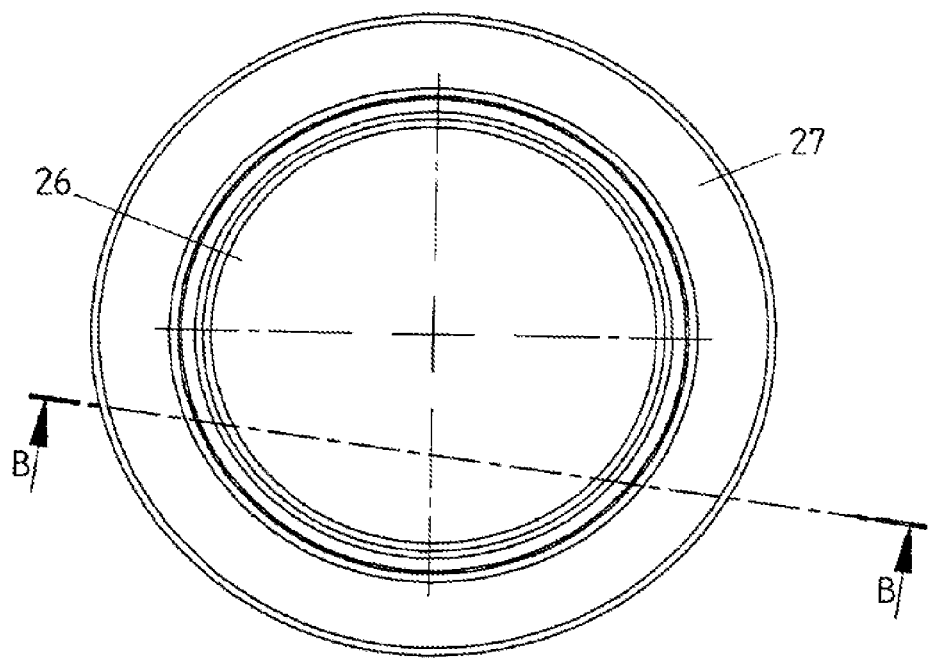
Figure 36B:
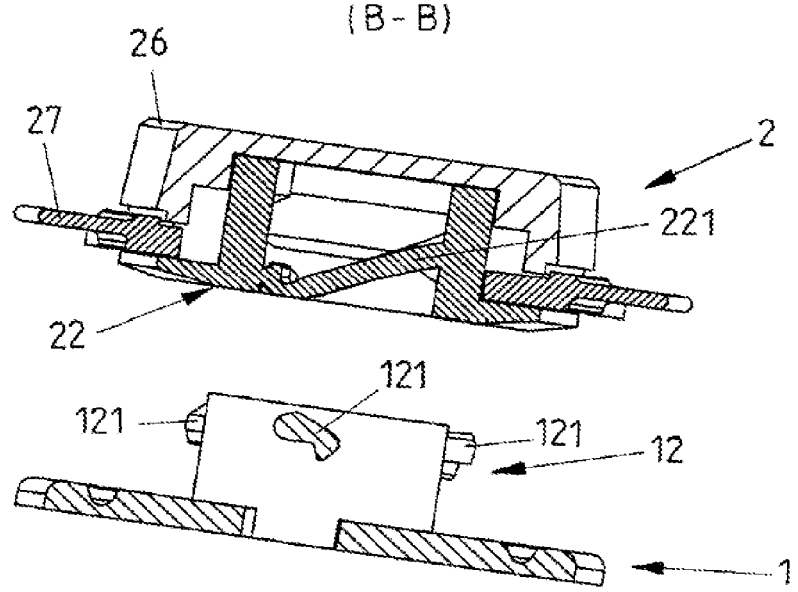

As is illustrated, in this connection, in particular by looking at FIG. 34B, during the opening of the closure device V when the second connection element 22 rotates in the first direction of rotation D1, a closure portion 221 slides along a sliding surface 2212 on the additional (second) guide surface 1212 of a guide portion 121. The guide portion 121 therefore comprises here two guide surfaces 1210 and 1211 which each extend at an angle and which, when the second connection element 22 is rotated in the same direction of rotation D1, provide physical guiding for the second connection element 22 with reference to the first connection element 12, however, depending on whether the closure device V is closed or opened, only the one or the other guide surface 1210 or 1211 providing the guiding. In this case, when closing the closure device V, the closure portion 221 abuts against the one (first) guide surface 1210 which, with the closure device V closed, engages behind the associated guide portion 121 in part. When opening the closure device V, it is not this closure portion 221 that abuts against the other (second) guide surface 1211 of the guide portion 121 but an adjacent closure portion 221 with a sliding surface 2211.

In order, when closing the closure device V, to support automatic rotating-in of the second connection element 22 relative to the first connection element 12 and, when opening the closure device V, to enable smooth rotating-open for a user, each sliding surface 2210, 2211 is realized at an angle of more than 60° to the connection axis A, in the present case by approximately 70°.

In the case of the closure device V in FIGS. 27A to 36E, when rotating the second connection element 22 out of its closed position in the first direction of rotation D1, adjustment beyond the intermediate position is additionally allowed. In this way, when opening the closure device V, the two magnetic elements M3 and M4 can be moved into a relative position with respect to one another in which they repel one another and consequently support the separation of the two closure parts 1 and 2 from one another.

LIST OF REFERENCES

1 First closure part
11 First securing element
110 Bearing opening
12 Connection element
121 Guide portion
1210 Guide surface
1211 Additional (second) guide surface
1212 First blocking part
122a, 122b Fixing lug
123 Recess (first anti-rotation portion)
124 Retaining portion
125 Bearing portion
2 Second closure part
21 Second securing element
211 Latching lug
212 Bayonet opening
22 Second connection element
220 Gripping region
221 Closure portion
2210 Sliding surface
2211 Sliding surface
2212 Second blocking part
222 Bearing web
223a, 223b Counter stop
224 Projection
225 Bearing portion
227 Stop
228 Insertion slot
23 Anti-rotation element
231 Positive locking element (second anti-rotation portion)
232 Closure hook
233 Securing collar
234 Spring bearing region
235 Bearing portion
24 Spring element
240 Spring end
25 Actuating element
250 Gripping region
251 Stop
252 Bearing web 255 Bearing portion
26 Rotational element
260 Connecting web
27 Stop ring/securing element
271a, 271b Counter stop
A Connection axis
D1, D2 Direction of rotation
M1, M2, M3, M4 Magnetic element
M30, M31, M40, M41 Magnetic segment
O Opening direction
S Closing direction
T Separation line
V Closure device

The invention claimed is:

1. A closure device with at least one first and one second closure part which are connectable together in order to close the closure device, and are releasable from one another in order to open the closure device, wherein
the second closure part movable toward the first closure part in a closing direction along a connection axis for closing the closure device,
the closure device comprises at least two magnetic elements which, when the closure parts are moved toward one another, cause magnetic attraction between the first closure part and the second closure part,
the first closure part comprises a first connection element and the second closure part comprises a second connection element, wherein, with the closure device closed, the first and second closure parts are held together by means of the first and second connection elements, and
the first connection element comprises at least one guide portion and the second connection element comprises at least one closure portion, wherein
the guide portion comprises a guide surface which is angled toward the connection axis, is contacted by the closure portion when the second closure part is moved toward the first closure part and which forces the second connection element to rotate about the connection axis relative to the connection element along a first direction of rotation when the first and second closure parts are moved closer together,
the guide portion comprises an end in the first direction of rotation such that the closure portion is guidable past the guide portion in the closing direction before the second connection element reaches an intermediate position relative to the first connection element,
the closure device comprises an adjusting device by means of which the second connection element in the intermediate position is acted upon with a force in a second direction of rotation opposite the first direction of rotation such that the second connection element is automatically rotated out of the intermediate position relative to the first connection element and about the connection axis along the second direction of rotation into a closed position, and
in the closed position the closure portion engages behind the guide portion at least in part in order to hold the first and second connection elements and consequently the first and second closure parts together, and for releasing the first and second closure parts from one another, the second connection element is rotatable in the first direction of rotation about the connection axis relative to the first connection element in order to open the closure device.

2. The closure device as claimed in claim 1, wherein the adjusting device is based on spring force and/or based on magnetic force in order to act upon the second connection element in the intermediate position with a spring force and/or a magnetic force in the second direction of rotation.

3. The closure device as claimed in claim 2, wherein an adjusting device based on magnetic force includes the at least two magnetic elements which cause magnetic attraction between the first closure part and the second closure part when the closure parts are moved toward one another.

4. The closure device as claimed in claim 2, wherein the first closure part includes at least one first anti-rotation portion and the second closure part includes at least one second anti-rotation portion, wherein the second connection element is rotatable on the second closure part relative to the second anti-rotation portion and the at least one first anti-rotation portion and the at least one second anti-rotation portion are non-rotatably connectable together when the closure device is closed, and the second closure part comprises at least one spring element as part of a spring force-based adjusting device, wherein the spring element is supported at the one end on the connection element and at the other end on an anti-rotation element of the second closure part comprising the second anti-rotation portion.

5. The closure device as claimed in claim 1, wherein at least one magnetic element comprises two different magnetic poles in a plane which extends substantially perpendicularly to the closing direction or at least two magnetic elements are provided on a closure part in such a manner that in this way two different magnetic poles are present in a plane which extends substantially perpendicularly to the closing direction.

6. The closure device as claimed in claim 5, wherein the at least one magnetic element, which comprises two different magnetic poles in a plane which extends substantially perpendicular to the closing direction, is magnetized transversely relative to the closing direction and consequently a dividing line between a north pole and a south pole of the magnetic element runs transversely to the closing direction.

7. The closure device as claimed in claim 5, wherein
rotation of the second connection element relative to the first connection element out of the closed position in the first direction of rotation is permitted beyond the intermediate position and
each closure part comprises at least one magnetic element with two different magnetic poles or at least two magnetic poles in such a manner that two different magnetic poles are present on the closure part in a plane which extends substantially perpendicularly to the closing direction, and
the magnetic elements of the first and second closure parts are arranged in such a manner on the first and second closure parts that the magnetic elements
(a) magnetically attract when the closure device is closed and, with the second connection element in the intermediate position, are arranged in such a manner with respect to one another that the two connection elements, on account of the acting magnetic forces, strive to assume a relative position with respect to one another which corresponds to the closed position, and
(b) magnetically repel when the closure device is opened when the second connection element is rotated out of the closed position relative to the first connection element in the first direction of rotation or is rotated in the second direction of rotation beyond the intermediate position.

8. The closure device as claimed in claim 1, wherein the guide portion comprises two different guide surfaces in such a manner that when the closure device is closed, the second connection element is guided on the one guide surface, which is angled toward the connection axis, for the rotation of the second connection element in the first direction of rotation and when the closure device is opened, guiding occurs on the other guide surface for the rotation in the first direction of rotation in such a manner that when the closure device is opened, the two closure parts are separated in a screwing manner in a direction opposite the closing direction.

9. The closure device as claimed in claim 8, wherein the two different guide surfaces extend with respect to one another at an angle of more than 90°.

10. The closure device as claimed in claim 1, wherein the first closure part includes at least one first anti-rotation portion and the second closure part includes at least one second anti-rotation portion, wherein the second connection element is rotatable on the second closure part relative to the second anti-rotation portion and the at least one first anti-rotation portion and the at least one second anti-rotation portion are non-rotatably connectable together when the closure device is closed.

11. The closure device as claimed in claim 10, wherein the second closure part comprises an actuating element which is rotatable relative to the second anti-rotation portion and relative to the second connection element and which, with the closure device closed, is rotatable in the first direction of rotation about the connection axis in order to act upon the second connection element and to rotate the second connection element relative to the first connection element.

12. The closure device as claimed in claim 11, wherein, with the closure device closed, the actuating element is held in a relative position to the second connection element, from which the actuating element has to bridge a predefined void rotational path in the first direction of rotation before the actuating element acts on the second connection element and the closure device is able to be opened as intended.

13. The closure device as claimed in claim wherein the actuating element, with the closure device closed, is held by means of the at least two magnetic elements in the relative position to the second connection element, from which the actuating element has to bridge the predefined void rotational path in the first direction of rotation before the actuating element acts on the second connection element.

14. The closure device as claimed in claim 11, wherein the actuating element and the second connection element are realized and arranged in such a manner that the second connection element, when rotating into the intermediate position along the first direction of rotation, acts on the actuating element and rotates the actuating element about the connection axis in the first direction of rotation.

15. The closure device as claimed in claim 1, wherein, in the closed position, the guide portion and the closure portion are displaceable axially relative to one another by a defined clearance with reference to the connection axis, the guide portion and the closure portion, however, are blocked against rotation relative to one another about the connection axis by blocking parts of the first and second connection elements which interact after bridging the clearance when, with the second connection element in the closed position, a force, which loads the respective closure part in a direction pointing away from the other closure part, cooperates with the first and/or second closure part along the connection axis.

16. The closure device as claimed in claim 15, wherein a first blocking part is provided on the guide portion and a second blocking part is provided on the closure portion.

17. A holder for securing an object on a two-wheeler or three-wheeler having a closure device as claimed in claim 1.

18. A holder for securing an electronic device on a carrier element, having a closure device as claimed in claim 1, wherein one of the closure parts is to be connected to the carrier element and the other of the closure parts to the electronic device.

19. A closure for clothes, shoes or prostheses having a closure device as claimed in claim 1.

20. A closure device, with at least one first and one second closure part which are connectable together in order to close the closure device, and are releasable from one another in order to open the closure device, wherein
  the second closure part is movable toward the first closure part in a closing direction along a connection axis for closing the closure device,
  the closure device comprises at least two magnetic elements which, when the closure parts are moved toward one another, cause magnetic attraction between the first closure part and the second closure part,
  the first closure part comprises a first connection element and the second closure part a second connection element, wherein, with the closure device closed, the first and second closure parts are held together by means of the first and second connection elements, and
  the first connection element comprises at least one guide portion and one holding portion and the second connection element at least one first and one second closure portion, wherein
  the guide portion comprises a guide surface which is angled toward the connection axis, is contacted by the closure portion when the second closure part is moved to the first closure part and which forces the second connection element to rotate about the connection axis relative to the connection element along a first direction of rotation when the first and second closure parts are moved closer together,
  the guide portion and the holding portion each comprise an end in the first direction of rotation such that the first closure portion is guidable past the guide portion in the closing direction and the other second closure portion past the holding portion before the second connection element reaches an intermediate position relative to the first connection element,
  the closure device comprises an adjusting device by means of which the second connection element in the intermediate position is acted upon with a force in a second direction of rotation opposite the first direction of rotation such that the second connection element is automatically rotated out of the intermediate position relative to the first connection element and about the connection axis along the second direction of rotation into a closed position, and
  in the closed position the second closure portion engages behind the holding portion at least in part in order to hold the first and second connection elements and consequently the first and second closure parts together, and for releasing the first and second closure parts from one another, the second connection element is rotatable in the first direction of rotation about the connection axis relative to the first connection element in order to open the closure device.

* * * * *